US010988500B2

(12) United States Patent
Jiang et al.

(10) Patent No.: US 10,988,500 B2
(45) Date of Patent: *Apr. 27, 2021

(54) LIPID A MIMICS, METHODS OF PREPARATION, AND USES THEREOF

(71) Applicant: Immunovaccine Technologies Inc., Dartmouth (CA)

(72) Inventors: Zi-hua Jiang, Thunder Bay (CA); Jordan David Lewicky, Thunder Bay (CA); Genevieve Mary Weir, Dartmouth (CA); Rajkannan Rajagopalan, Dartmouth (CA); Leeladhar Sammatur, Irvine, CA (US); Marianne Michelle Stanford, Upper Tantallon (CA); Marc Mansour, Halifax (CA)

(73) Assignee: Immunovaccine Technologies Inc., Dartmouth (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/715,843

(22) Filed: Dec. 16, 2019

(65) Prior Publication Data

US 2020/0109160 A1 Apr. 9, 2020

Related U.S. Application Data

(63) Continuation of application No. 15/541,774, filed as application No. PCT/CA2015/051309 on Dec. 11, 2015, now Pat. No. 10,533,033.

(60) Provisional application No. 62/100,233, filed on Jan. 6, 2015.

(51) Int. Cl.
| | | |
|---|---|---|
| C07H 11/04 | (2006.01) | |
| A61K 39/39 | (2006.01) | |
| A61K 39/12 | (2006.01) | |
| A61K 31/7028 | (2006.01) | |
| C07H 15/18 | (2006.01) | |
| A61K 39/00 | (2006.01) | |
| A61K 31/7088 | (2006.01) | |
| C12N 7/00 | (2006.01) | |

(52) U.S. Cl.
CPC .......... *C07H 11/04* (2013.01); *A61K 31/7028* (2013.01); *A61K 31/7088* (2013.01); *A61K 39/0011* (2013.01); *A61K 39/12* (2013.01); *A61K 39/39* (2013.01); *C07H 15/18* (2013.01); *C12N 7/00* (2013.01); *A61K 2039/55555* (2013.01); *A61K 2039/55572* (2013.01); *A61K 2039/585* (2013.01); *A61K 2039/605* (2013.01); *A61K 2039/6031* (2013.01); *A61K 2039/6037* (2013.01); *C12N 2710/20034* (2013.01); *C12N 2710/20071* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,029,762 A | 6/1977 | Galanos et al. | |
| 4,722,848 A | 2/1988 | Paoletti et al. | |
| 5,158,941 A | 10/1992 | Jadhav et al. | |
| 5,191,072 A | 3/1993 | Hasegawa et al. | |
| 5,220,009 A | 6/1993 | Mazur et al. | |
| 5,278,300 A | 1/1994 | Hasegawa et al. | |
| 5,554,372 A | 9/1996 | Hunter | |
| 5,580,859 A | 12/1996 | Felgner et al. | |
| 5,589,466 A | 12/1996 | Felgner et al. | |
| 5,648,343 A | 7/1997 | Carlson | |
| 5,679,647 A | 10/1997 | Carson et al. | |
| 5,736,524 A | 4/1998 | Content et al. | |
| 5,739,118 A | 4/1998 | Carrano et al. | |
| 5,804,566 A | 9/1998 | Carson et al. | |
| 5,922,687 A | 7/1999 | Mann et al. | |
| 6,113,918 A | 9/2000 | Johnson et al. | |
| 6,235,724 B1 | 5/2001 | Asai et al. | |
| 6,245,523 B1 | 6/2001 | Altieri | |
| 6,368,604 B1 | 4/2002 | Hone et al. | |
| 6,699,846 B2 | 3/2004 | Elliott et al. | |
| 6,764,840 B2 | 7/2004 | Johnson et al. | |
| 6,793,923 B2 | 9/2004 | Brown et al. | |
| 7,491,707 B1 | 2/2009 | Jiang et al. | |
| 7,510,698 B2 | 3/2009 | Momin et al. | |
| 7,541,020 B2 | 6/2009 | Johnson et al. | |

(Continued)

FOREIGN PATENT DOCUMENTS

| | | |
|---|---|---|
| CA | 2217164 A1 | 10/1996 |
| DE | 19512484 A1 | 10/1996 |

(Continued)

OTHER PUBLICATIONS

Extended European Search Report dated Sep. 18, 2018 issued in European International Application No. 15876412.6.

(Continued)

*Primary Examiner* — Layla D Berry
(74) *Attorney, Agent, or Firm* — Troutman Pepper Hamilton Sanders LLP

(57) ABSTRACT

The invention provides lipid A mimics in which one or both of the sugar residues of a natural lipid A disaccharide backbone has been replaced with an aromatic group. These lipid A mimics may further differ from a natural lipid A molecule with respect to other structural characteristics, such as, a different number of phosphate groups present, changes in the number, structure and location of lipid chains and/or changes in the spacing and linkage of the sugar residues (or their aromatic replacements). The lipid A mimics may be lipid A agonists and as such may be useful as immunostimulatory agents in inducing or patenting an antibody and/or cell-mediated immune response, or may be lipid A antagonists and as such may be useful in treating or preventing a lipopolysaccharide (LPS)/lipid A-mediated disease or disorder. Also provided are methods for preparing the lipid A mimics.

22 Claims, 8 Drawing Sheets

Specification includes a Sequence Listing.

(56) References Cited

U.S. PATENT DOCUMENTS

| | | | |
|---|---|---|---|
| 7,820,627 | B2 | 10/2010 | Jiang et al. |
| 7,824,686 | B2 | 11/2010 | Brown et al. |
| 8,097,593 | B1 | 1/2012 | Jiang et al. |
| 8,216,595 | B2 | 7/2012 | Moon et al. |
| 8,628,937 | B2 | 1/2014 | Brown et al. |
| 9,114,174 | B2 | 8/2015 | Brown et al. |
| 9,498,493 | B2 | 11/2016 | Mansour et al. |
| 2007/0196394 | A1 | 8/2007 | Cohen et al. |
| 2008/0233154 | A1 | 9/2008 | Berthet et al. |
| 2009/0149647 | A1 | 6/2009 | Tagami et al. |
| 2011/0070298 | A1 | 3/2011 | Mansour et al. |
| 2012/0190633 | A1 | 7/2012 | Guo et al. |
| 2014/0011987 | A1 | 1/2014 | Boons |
| 2014/0234404 | A1 | 8/2014 | Mansour et al. |
| 2015/0202152 | A1 | 7/2015 | Daftarian et al. |
| 2016/0067335 | A1 | 3/2016 | Mansour et al. |
| 2017/0028084 | A1 | 2/2017 | Mansour et al. |

FOREIGN PATENT DOCUMENTS

| | | |
|---|---|---|
| EP | 0 593 765 | 4/1994 |
| EP | 1 959 992 | 1/2012 |
| GB | 1324287 | 7/1973 |
| WO | WO 1992/016230 | 10/1992 |
| WO | WO 1998/004720 | 2/1998 |
| WO | 2001036433 A2 | 5/2001 |
| WO | WO 2002/038175 | 5/2002 |
| WO | 2003002072 A1 | 1/2003 |
| WO | WO 2003/094850 | 11/2003 |
| WO | WO 2004/062599 A2 | 7/2004 |
| WO | WO 2004/067023 | 8/2004 |
| WO | WO 2006/081826 | 8/2006 |
| WO | WO 2007/041832 | 4/2007 |
| WO | 2009035528 A2 | 3/2009 |
| WO | WO 2009/039628 | 4/2009 |
| WO | WO 2009/043165 | 4/2009 |
| WO | WO 2009/146523 | 12/2009 |
| WO | 2013049941 A1 | 4/2013 |
| WO | WO 2013/049941 | 4/2013 |
| WO | WO 2014/032737 A1 | 3/2014 |
| WO | WO 2014/141127 A1 | 9/2014 |
| WO | WO 2014/153636 | 10/2014 |
| WO | 2015035337 A1 | 3/2015 |
| WO | WO 2016/176761 | 11/2016 |
| WO | WO 2017/083963 | 5/2017 |

OTHER PUBLICATIONS

Adanitsch et al., "Development of αGlcN(1-1)αMan-Based Lipid A Mimetics as a Novel Class of Potent Toll-like Receptor 4 Agonists", Journal of Medical Chemistry, vol. 57, No. 19 pp. 8056-8073 (Sep. 25, 2014).
Reichert C M et al., "Synthesis of conjugates containing N-acetylmuramyl-l-alanyl-d-isoglutaminyl (MDP). Their use as hapten-carrier systems", Molecular Immunology, vol. 17, No. 3., pp. 357-363 (Mar. 1, 1980).
Lewicky, J.D. et al., "Synthesis of a dimeric monosaccharide lipid A mimic and its synergistic effect on the immunostimulatory activity of lipopolysaccharide" (2011), Carbohydr. Res., 346(13): 1705-1713.
Mansour et al., "Therapy of established B16-F10 melanoma tumors by a single vaccination of CTL/T helper peptides in VacciMax®" (2007), J Transl Med, 5: 20.
Merrifield, B., "Concept and Early Development of Solid-Phase Peptide Synthesis" (1997), Methods Enzymol. 289: 3-13.
Moyle et al., "Self-Adjuvanting Lipopeptide Vaccines" (2008), Curr Med Chem, 15: 506-516.
Needleman & Wunsch, "A General Method Applicable to the Search for Similarities in the Amino Acid Sequence of Two Proteins" (1970), J. Mol. Biol., 48: 443-453.
Park, B.S. et al., "The structural basis of lipopolysaccharide recognition by the TLR4-MD-2 complex" (2009), Nature, 458: 1191-1196.
Pearson, W.R. & Lipman, D.J., "Improved tools for biological sequence comparison" (1988), Proc. Natl. Acad. Sci. USA, 85: 2444-2448.
Pomerantz et al., "Lipopolysaccharide is a potent monocyte/macrophage-specific stimulator of human immunodeficiency virus type 1 expression" (1990), J. Exp. Med., 172(1): 253-261.
Reddy, R. et al., "In Vivo Cytotoxic T Lymphocyte Induction with Soluble Proteins Administered in Liposomes" (1992), J. Immunol., 148: 1585.
Roberge, J.Y. et al., "A Strategy for a Convergent Synthesis of N-Linked Glycopeptides on a Solid Support" (1995), Science, 269: 202-204.
Robinson, H. L., Hunt, L. A., & Webster, R. G., "Protection against a lethal influenza virus challenge by immunization with a haemagglutinin-expressing plasmid DNA" (1993), Vaccine, 11: 957.
Rock, K. L., "A new foreign policy: MHC class I molecules monitor the outside world" (1996), Immunol. Today, 17: 131.
Slingluff et al., "Phase I Trial of a Melanoma Vaccine with gp100(280-288) Peptide and Tetanus Helper Peptide in Adjuvant" (2001), Clin Cancer Res., 7(10): 3012-3024.
Smith, T.F. & Waterman, M.S., "Comparison of Biosequences" (1981), Adv. Appl. Math, 2: 482-489.
So, "Vigorous Response of Human Innate Functionning IgM Memory B Cells upon Infection by Neisseria Gonorrhoeae" (2012), J Immunol, 188(8):4008-4022.
Stöver, A.G. et al., "Structure-Activity Relationship of Synthetic Toll-Like Receptor 4 Agonists" (2004), Journal of Biological Chemistry, 279(6): 4440-4449.
Stover et al., "New use of BCG for recombinant vaccines" (1991), Nature, 351: 456-460.
Takahashi et al., "Induction of CD8+ cytotoxic T cells by immunization with purified HIV-1 envelope protein in ISCOMs" (1990), Nature, 344: 873-875.
Tam, J. P., "Recent advances in multiple antigen peptides" (1996), J. Immunol. Methods, 196: 17-32.
Tam, J. P., "Synthetic peptide vaccine design: synthesis and properties of a high-density multiple antigenic peptide system" (1988), Proc. Natl. Acad. Sci. U.S.A., 85: 5409-5413.
Top, F. H. et al., "Immunization with Live Types 7 and 4 Adenovirus Vaccines. I. Safety, Infectivity, Antigenicity, and Potency of Adenovirus" (1971), J. Infect. Dis., 124: 148.
Ulmer, J. B. et al., "Heterologous Protection Against Influenza by Injection of DNA Encoding a Viral protein" (1993), Science, 259: 1745.
Vitiello, A. et al.,"Development of a lipopeptide-based therapeutic vaccine to treat chronic HBV infection. I. Induction of a primary cytotoxic T lymphocyte response in humans" (1995), J. Clin. Invest., 95(1): 341-349.
Warren, H. S., Vogel, F.R., & Chedid, L.A., "Current Status of Immunological Adjuvants" (1986), Annu. Rev. Immunol., 4: 369-388.
Webster et al., "Antigenic variation among type A influenza viruses," (1983), In: P. Palese and D. W. Kingsbury (ed.), Genetics of influenza viruses, 127-168, Springer-Verlag, New York.
Zhao et al., "Binding of Spin-Labeled Galactosides to the Lactose Permease of Escherichia coli" (2000), Biochemistry, 39(37): 11381-11388.
International Search Report (ISR) in respect of PCT/CA2015/051309, dated Mar. 10, 2016.
International Preliminary Report on Patentability (IPRP) in respect of PCT/CA2015/051309, dated Jul. 11, 2017.
Akira, S. M. et al., "Lipid A Receptor TLR4-Mediated Signaling Pathways" (2009), Adv. Exp. Med. Biol., 667: 59-68.
Alexander et al., "Chemical Structure of Lipid A—The Primary Immunomodulatory Center of Bacterial Lipopolysacchrides" (2002), Trends in Glycoscience and Glycotechnology, 14: 69-86.
Alonso et al., "Biodegradable microspheres as controlled-release tetanus toxoid delivery systems" (1994), Vaccine 12:299-306.
Altieri et al., "Survivin Apoptosis: An Interloper Between Cell Death and Cell Proliferation in Cancer" (1999), Lab Invest, 79: 1327-1333.
Altschul et al. "Basic Local Alignment Search Tool" (1990), J. Mol. Biol., 215:403-410.

(56) References Cited

OTHER PUBLICATIONS

Bagga et al., "Synthesis of glycosides in which the aglycon is an N-(hydroxymethyl)amino-1,3,5-triazine derivative" (Jun. 1, 1997), Glycoconjugate Journal, 14(4): 519-521.
Banga, A. K., Therapeutic Peptides and Proteins, Formulation, Processing and Delivery Systems (1995) Technomic Publishing Co., Lancaster, Pa.
Basith, S. et al., "Toll-like receptor modulators: a patent review (2006-2010)" (2011), Expert Opin. Ther. Patents, 21 (6):927-944.
Bazin, H.G. et al., "The 'Ethereal' nature of TLR4 agonism and antagonism in the AGP class of lipid A mimetics" (2008), Bioorg. Med. Chem. Lett., 18:5350-5354.
Berinstein et al., "First-in-man application of a novel therapeutic cancer vaccine formulation with the capacity to induce multifunctional T cell responses in ovarian, breat and prostate cancer patients" (2012), J Transl Med, 10(1): 156.
Bone, R.C., Gram-Negative Sepsis: a Dilemma of Modern Medicine (1993), Clin. Microbiol. Rev., 6: 57-68.
Bulusu, M.A.R.C et al., "Acyclic Analogues of Lipid A: Synthesis and Biological Activities" (1992), J. Med. Chem., 35: 3463-3469.
Caruthers, M.H. et al., "New Chemical methods for synthesizing polynucleotides" (1980), Nucleic Acids Res. Symp. Ser. No. 7, 215-223.
Cease, K. B., and Berzofsky, J. A., "Toward a Vaccine for AIDS: The Emergence of Immunobiology-Based Vaccine Development" (1994), Annu. Rev. Immunol. 12: 923-89.
Celis et al., "Recognition of Hepatitis B Surface Antigen by Human T Lymphocytes: Proliferation and Cytotoxic Responses to a Major Antigenic Determinant Defined by Synthetic Peptides" (1988), J. Immunol. 140: 1808-1815.
Chakrabarti, S. et al., "Expression of the HTLV-III envelope gene by a recombinant vaccinia virus" (1986), Nature, 320: 535.
Chanda, P. K. et al., "High Level Expression of the Envelope Glycoproteins of the Human Immunodeficiency Virus Type I in Presence of rev Gene Using Helper-Independent Adenovirus Type 7 Recombinants" (1990), Virology, 175: 535-547.
Chong et al., "Identification of T- and B-Cell Epitopes of the S2 and S3 Subunits of Pertussis Toxin by Use of Synthetic Peptides" (1992), Infect. Immun., 60: 4640-4647.
Coler, R.N. et al., "Development and Characterization of Synthetic Glucopyranosyl Lipid Adjuvant System as a Vaccine Adjuvant" (2011), PLoS One, 6(1): e16333.
Daftarian et al., "Rejection of large HPV-16 expressing tumors in aged mice by a single immunization of VacciMax® encapsulated CTL/T helper peptides" (2007), J Transl Med, 5: 26.
Demotz et al., "Delineation of Several Re-restricted Tetanus Toxin T Cell Epitopes" (1989), J. Immunol., 142: 394-402.
Diethelm-Okita, B.M. et al., "Universal Epitopes for Human CD4 Cells on Tetanus and Diphtheria Toxins" (2000), J. Infect. Diseases, 181: 1001-1009.
Eldridge, et al. "Biodegradable Microspheres as a Vaccine Delivery System" (1991), Molec. Immunol., 28: 287-294.
Eldridge, J. H. et al., "New Advances in Vaccine Delivery Systems" (1993), Sem. Hematol., 30: 16-25.
Falo, L. D., Jr. et al., "Targeting antigen into the phagocytic pathway in vivo induces protective tumour immunity" (1995), Nature Med., 7: 649.
Fitzgerald, K.A. & Golenbock, D.T., "The Shape of Things to Come" (2007), Science, 316: 1574-1576.
Fox C.B. et al., "Synthetic and Natural TLR4 Agonists as Safe and Effective Vaccine Adjuvants." (2010), In: Wang X., Quinn P. (eds) Endotoxins: Structure, Function and Recognition. Subcellular Biochemistry, 53: 303-21, Springer, Dordrecht.
Frezard, F., "Liposomes: from biophysics to the design of peptide vaccines" (1999), Braz. J. Med. Bio. Res., 32: 181-189.
Fujimoto, Y. et al., "Synthesis of lipid A and its analogues for investigation of the structural basis for their bioactivity" (2005), Journal of Endotoxin Research, 11(6): 341-347.

Garcon et al., "GlaxoSmithKline Adjuvant Systems in vaccines: concepts, achievements and perspectives" (2007), Expert Rev. Vaccines, 6: 723-739.
Goedert & Spillantini, "A Century of Alzheimer's Disease" (2006), Science, 314: 777-781.
Gregoriadis, G., "Immunological adjuvants: a role for liposomes" (1990), Immunol. Today, 11: 89-97.
Gupta, R. K. et al., "Adjuvants—a balance between toxicity and adjuvanticity" (1993), Vaccine, 11: 293-306.
Hattori et al., "Lipid A and the Lipid A Analogue Anti-Tumour Compound ONO-4007 Induce Nitric Oxide Synthase In Vitro and in Vivo" (1995), European Journal of Pharmacology, 291: 83-90.
Hawkins, L.D. et al., "A Novel Class of Endotoxin Receptor Agonists with Simplified Structure, Toll-Like Receptor 4-Dependent Immunostimulatory Action, and Adjuvant Activity" (2002), J. Pharmacol. Exp. Therap., 300: 655-661.
Hu et al., "The immunostimulating complex (ISCOM) is an efficient mucosal delivery system for respiratory syncytial virus (RSV) envelope antigens inducing high local and systemic antibody responses" (1998), Clin Exp Immunol., 113: 235-243.
Hu, S. L. et al., "Expression of AIDS virus envelope gene in recombinant vaccinia viruses" (1986), Nature 320:537.
Itzhaki & Wozniak, "Herpes Simplex Virus Type 1 in Alzheimer's Disease: The Enemy Within" (2008), J Alzheimers Dis, 13: 393-405.
Jiang, Z. et al., "Synthetic Vaccines: The Role of Adjuvants in Immune Targeting" (2003), Curr. Med. Chem., 10: 1423-1439.
Jiang, Z. et al., "Monophosphoryl lipid A analogues with varying 3-O-substitution: synthesis and potent adjuvant activity" (2007), Carbohydrate Research, 342: 784-796.
Jiang, Z. et al., "Novel lipid A mimetics derived from pentaerythritol: synthesis and their potent agonistic activity" (2002), Tetrahedron, 58: 8833-8842.
Johnson et al., Synthesis and biological evaluation of a new class of vaccine adjuvants: Aminoalkyl Glucosaminide 4-phosphates (AGPs) (1999), Bioorganic & Medicinal Chemistry Letters, 9: 2273-2278.
Johnson, A. G., "Adjuvant action of bacterial endotoxins on the primary antibody response" (1964), in Landy, M. and Braun, W. (eds.), Bacterial Endotoxins, Rutgers University Press, New Brunswick, CT, 252-262.
Jones et al., "Protection of mice from Bordetella pertussis respiratory infection using microencapsulated pertussis fimbriae" (1995), Vaccine, 13: 675-681.
Karkada et al., "A Novel Breast/Ovarian Cancer Peptide Vaccine Platform That Promotes Specific Type-1 but not Treg/Tr1-type Responses" (2010), J Immunother, 33(3): 250-261.
Kawaoka et al., "Molecular Characterization of New Hemagglutinin, Subtype H14, of Influenza A virus" (1990), Virology, 179: 759-767.
Kieny, M.-P. et al., "Aids Virus ENV Protein Expressed from a Recombinant Vaccinia Virus" (1986), AIDS Bio/Technology, 4: 790-795.
Kofler, N. et al., "Preparation and characterization of poly-(D,L-lactide-co-glycolide) and poly-(L-lactic acid) microspheres with entrapped pneumotropic bacterial antigens" (1996), J. Immunol. Methods., 192: 25.
Lewicky, J.D. et al., "Improving the immunostimulatory potency of diethanolamine containing lipid A mimics" (2013), Bioorg. Med. Chem., 21(8): 2199-2209.
Lewicky, J.D. et al., "Synthesis and immunostimulatory activity of diethanolamine-containing lipid A mimics" (2012), RSC Advances, 2(5): 1917-1926.
M. Alajarin, Science of Synthesis, Product Class 31.44: P-Heteroatom-Substituted Arylphosphines, (2007) pp. 2105-2153.
Pengyuan Liu et al., "Ion-Neutral Complexes Resulting from Dissociative Protonation: Fragmentation of α-Furanylmethyl Benzyl Ethers and 4-N,N-dimethylbenzyl Benzyl Ethers", J. Am Soc Mass Spectrom, (2010) 21, pp. 626-634.
K. Lohith et al., "Glycosides and amino acyl esters of carbohydrates as potent inhibitors of angiotensin converting enzyme", European Journal of Medicinal Chemistry 41 (2006) pp. 1059-1073.

(56) References Cited

OTHER PUBLICATIONS

Arvind S. More et al., "Synthesis and Characterization of polyamides containing pendant pentadecyl chains", European Polymer Journal 46 (2010) pp. 557-567.
European Office Action issued in EP Application No. 15876412.6 dated Feb. 27, 2020.

*E. coli* lipid A

JL-265

JL-266

A

B

SEQUENCE LISTING

```
<160> NUMBER OF SEQ ID NOS: 24

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide - HPV16E7 (H-2Db) peptide
      49-67

<400> SEQUENCE: 1

Arg Ala His Tyr Asn Ile Val Thr Phe
1               5

<210> SEQ ID NO 2
<211> LENGTH: 429
<212> TYPE: DNA
<213> ORGANISM: Homo sapiens

<400> SEQUENCE: 2
atgggtgccc cgacgttgcc ccctgcctgg cagcccttc tcaaggacca ccgcatctct     60
acattcaaga actggcccct cttggagggc tgcgcctgca ccccggagcg gatggccgag    120
gctggcttca tccactgccc cactgagaac gagccagact tggcccagtg tttcttctgc    180
ttcaaggagc tggaaggctg ggagccagat gacgacccca tagaggaaca taaaaagcat    240
tcgtccggtt gcgctttcct ttctgtcaag aagcagtttg aagaattaac ccttggtgaa    300
tttttgaaac tggacagaga aagagccaag aacaaaattg caaaggaaac caacaataag    360
aagaaagaat tgaggaaac tgcgaagaaa gtgcgccgtg ccatcgagca gctggctgcc    420
atggattga                                                            429

<210> SEQ ID NO 3
<211> LENGTH: 142
<212> TYPE: PRT
<213> ORGANISM: Homo sapiens

<400> SEQUENCE: 3

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
                20                  25                  30

Cys Thr Pro Glu Arg Met Ala Glu Ala Gly Phe Ile His Cys Pro Thr
            35                  40                  45

Glu Asn Glu Pro Asp Leu Ala Gln Cys Phe Phe Cys Phe Lys Glu Leu
        50                  55                  60

Glu Gly Trp Glu Pro Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110
```

Ile Ala Lys Glu Thr Asn Asn Lys Lys Glu Phe Glu Glu Thr Ala
            115                 120                 125
Lys Lys Val Arg Arg Ala Ile Glu Gln Leu Ala Ala Met Asp
    130                 135                 140

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide - Survivin peptide SurA1
<220> FEATURE:
<221> NAME/KEY: MISC_FEATURE
<222> LOCATION: (1)..(9)
<223> OTHER INFORMATION: survivin93-101

<400> SEQUENCE: 4

Phe Glu Glu Leu Thr Leu Gly Glu Phe
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide - Modified survivin peptide
      SurA1.T

<400> SEQUENCE: 5

Phe Thr Glu Leu Thr Leu Gly Glu Phe
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide - Survivin peptide SurA2
<220> FEATURE:
<221> NAME/KEY: MISC_FEATURE
<222> LOCATION: (1)..(9)
<223> OTHER INFORMATION: survivin96-104

<400> SEQUENCE: 6

Leu Thr Leu Gly Glu Phe Leu Lys Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide - Modified survivin peptide
      SurA2.M

<400> SEQUENCE: 7

Leu Met Leu Gly Glu Phe Leu Lys Leu
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide - Survivin peptide SurA3
<220> FEATURE:
<221> NAME/KEY: MISC_FEATURE
<222> LOCATION: (1)..(10)
<223> OTHER INFORMATION: survivin18-27

```
<400> SEQUENCE: 8

Arg Ile Ser Thr Phe Lys Asn Trp Pro Phe
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide - Modified survivin peptide
      SurA3.K

<400> SEQUENCE: 9

Arg Ile Ser Thr Phe Lys Asn Trp Pro Lys
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide - Survivin peptide SurA24

<400> SEQUENCE: 10

Ser Thr Phe Lys Asn Trp Pro Phe Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide - Survivin peptide SurB7

<400> SEQUENCE: 11

Leu Pro Pro Ala Trp Gln Pro Phe Leu
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide

<400> SEQUENCE: 12

Thr Ile His Asp Ile Ile Leu Glu Cys Val
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13

Tyr Met Leu Asp Leu Gln Pro Glu Thr Thr
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 14

Leu Leu Met Gly Thr Leu Gly Ile Val
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic peptide

<400> SEQUENCE: 15

Thr Leu Gly Ile Val Cys Pro Ile
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Ser Val Tyr Asp Phe Phe Val Trp Leu
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

Val Tyr Asp Phe Phe Val Trp Leu
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide

<400> SEQUENCE: 18

Lys Tyr Met Cys Asn Ser Ser Cys Met
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

Lys Tyr Ile Cys Asn Ser Ser Cys Met
1               5

<210> SEQ ID NO 20
<211> LENGTH: 22
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa may be cyclohexylalanyl

<400> SEQUENCE: 20

Ala Lys Xaa Val Ala Ala Trp Thr Leu Lys Ala Ala Ala Lys Tyr Ile
1               5                   10                  15

Cys Asn Ser Ser Cys Met
            20

<210> SEQ ID NO 21
<211> LENGTH: 16
<212> TYPE: PRT
<213> ORGANISM: Artificial Sequence
<220> FEATURE:
<223> OTHER INFORMATION: Synthetic peptide - Modified Tetanus toxoid
      peptide A16L

<400> SEQUENCE: 21

Ala Gln Tyr Ile Lys Ala Asn Ser Lys Phe Ile Gly Ile Thr Glu Leu
1               5                   10                  15

<210> SEQ ID NO 22
<211> LENGTH: 13
<212> TYPE: PRT
<213> ORGANISM: Artificial Sequence
<220> FEATURE:
<223> OTHER INFORMATION: Synthetic peptide - PADRE (pan-DR epitope)
<220> FEATURE:
<221> NAME/KEY: MISC_FEATURE
<222> LOCATION: (3)..(3)
<223> OTHER INFORMATION: Xaa may be cyclohexylalanyl

<400> SEQUENCE: 22

Ala Lys Xaa Val Ala Ala Trp Thr Leu Lys Ala Ala Ala
1               5                   10

<210> SEQ ID NO 23
<211> LENGTH: 21
<212> TYPE: PRT
<213> ORGANISM: Artificial Sequence
<220> FEATURE:
<223> OTHER INFORMATION: Synthetic peptide - Modified Tetanus toxoid
      peptide F21E

<400> SEQUENCE: 23

Phe Asn Asn Phe Thr Val Ser Phe Trp Leu Arg Val Pro Lys Val Ser
1               5                   10                  15

Ala Ser His Leu Glu
            20

<210> SEQ ID NO 24
<211> LENGTH: 20
<212> TYPE: DNA
<213> ORGANISM: Artificial Sequence
<220> FEATURE:
<223> OTHER INFORMATION: Synthetic polynucleotide - CpG ODN

<400> SEQUENCE: 24
tccatgacgt tcctgacgtt                                                   20
```

LIPID A MIMICS, METHODS OF PREPARATION, AND USES THEREOF

CROSS-REFERENCE TO RELATED APPLICATIONS

This application is a continuation of U.S. application Ser. No. 15/541,774, filed on Jul. 6, 2017, which issued as U.S. Pat. No. 10,533,033 on Jan. 14, 2020 and is a national phase of International Application No. PCT/CA2015/051309, titled "LIPID A MIMICS, METHODS OF PREPARATION, AND USES THEREOF", filed on Dec. 11, 2015, which claims priority to U.S. Provisional Application Ser. No. 62/100,233, filed on Jan. 6, 2015. The entire contents of these applications are incorporated herein by reference in their entirety.

SEQUENCE LISTING

This application contains a Sequence Listing which has been submitted in ASCII format via EFS-Web and is hereby incorporated by reference herein in its entirety. The ASCII text file created on Dec. 16, 2019, is named 249979_0000058SEQLIST.txt and is 7,568 bytes in size.

FIELD

The present invention relates to lipid A mimics characterized by the replacement of one or both of the sugar residues of a lipid A disaccharide backbone with an aromatic group, methods for their preparation, and uses thereof.

BACKGROUND

Vaccine strategy has been proven effective in providing protection against a host of maladies. Yet there are many pathogens and infections for which this strategy is not effective. Presently, there is an increasing need for more effective vaccines to combat acute and chronic infections and diseases. While traditional vaccine strategy employs live, attenuated pathogens as immunogens, contemporary vaccine development employs recombinant or synthetic subunit vaccines which usually offer improved safety and more precise targeting. However, subunit vaccines are characterized by poor immunogenicity and often must be co-administered with an adjuvant to enhance the immune response.

A vaccine adjuvant is a substance that is able to enhance the immune responses to the accompanying antigen of the vaccine formulation. While numerous classes of compounds have been explored as vaccine adjuvants, Alum, a mixture of aluminum salts, is still the most popular adjuvant for human vaccine use. In fact Alum was the only approved adjuvant for human vaccines for more than 70 years. It was not until late 2009 that the FDA approved GlaxoSmithKline's AS04 adjuvant (a proprietary combination of Alum and monophosphoryl lipid A, MPL®) (Garcon et al., Expert Rev. Vaccines, 6: 723-739, 2007) which was used for the Cervarix vaccine to immunize against human papillomavirus (HPV). There however remains a great need to develop and characterize new adjuvants for vaccine therapies. Discovery of novel adjuvants has emerged as a critical frontline effort in the development of modern vaccine formulations.

Lipopolysaccharide (LPS), also known as endotoxin, is the outer membrane component of Gram-negative bacteria. LPS was long ago described as a potent stimulus of antibody responses, and extensive studies led to the conclusion that the adjuvant activity of LPS was systemic (Johnson, A. G., "Adjuvant action of bacterial endotoxins on the primary antibody response", in Landy, M. and Braun, W. (eds.), Bacterial Endotoxins, Rutgers University Press, New Brunswick, Conn., pp. 252-262, 1964), rather than local, unlike aluminum or oil-based adjuvants which only worked if co-administered with the antigen. The active component of LPS for its immunostimulatory activity was later determined to be the lipophilic anchor of the molecule, known as lipid A. Both LPS and lipid A are too toxic to be used as an adjuvant for human vaccines. As such, much research has been conducted to separate the adjuvant activity from the pyrogenicity and toxicity of the parent LPS and lipid A molecules. As a result of many years' study and development, MPL® was approved by the FDA for human vaccine use in the Cervarix HPV vaccine developed by GlaxoSmithKline. MPL® is a product purified from cultured bacteria, which contains a mixture of structurally modified lipid A molecules. Through structural modification, the toxicity of lipid A has been reduced while the immunostimulatory activity of these molecules largely remains.

The molecular target and mechanisms of action for LPS/lipid A in regard to their immunostimulatory activity have been identified, thanks to the discovery of a group of proteins known as Toll-like receptors (TLRs) about 20 years ago. TLRs play important roles in innate immunity and the development of adaptive immune response. LPS/lipid A is recognized by Toll-like receptor 4 (TLR4), a member of TLR protein family, which is associated with another protein MD-2. The activation of the TLR4/MD-2 receptor complex leads to downstream signalling pathways that ultimately regulate innate immunity as well as the development of adaptive immune response. The crystal structure of TLR4/MD-2 with the bound ligand LPS has recently been determined (Park et al., Nature, 458: 1191-1196, 2009), which provides direct evidence for the molecular basis of recognition of LPS/lipid A by TLR4/MD-2. The recently approved adjuvant MPL® has also been shown to exert its activity through the mediation of TLR4/MD-2. It is now well recognized that TLR4 agonists are an important class of immunostimulatory vaccine adjuvants.

In the present disclosure, we report a group of novel lipid A mimics. These compounds are potentially useful as immune stimulants and/or modulators to treat various diseases.

SUMMARY

In one aspect, there is provided a lipid A mimic that is a compound of formula:

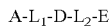

A-L$_1$-D-L$_2$-E wherein:
A is a cyclic monosaccharide residue with one or more of the hydroxyl groups optionally substituted or absent, or A is a substituted or unsubstituted aromatic group;
L$_1$ and L$_2$ independently are present or absent, and if present is independently a substituted or unsubstituted, branched or linear, saturated or unsaturated, carbon chain optionally comprising one or more of O, S or N;
D is —O—, —S— or —NH—; and
E is a cyclic monosaccharide residue with one or more of the hydroxyl groups optionally substituted or absent, or E is a substituted or unsubstituted aromatic group;
wherein at least one of A or E is a substituted or unsubstituted aromatic group and at least one of A, L$_1$, L$_2$ or E comprises one or more lipid chain substituents;
or a pharmaceutically acceptable salt thereof.

In some embodiments of the lipid A mimics of formula A-L$_1$-D-L$_2$-E, at least one of A or E is a substituted or unsubstituted benzene ring.

In an embodiment of the lipid A mimics of formula A-L$_1$-D-L$_2$-E, at least one of A or E is:

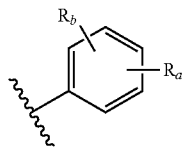

wherein:
R$_a$ is placed at any position on the benzene ring and is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6; and
R$_b$ is placed at any remaining position on the benzene ring and is —H, —OH, —NH$_2$, —Cl, —Br, —F, —COOH, —CN, —SO$_3$H, —OCH$_3$, —NO$_2$ or any substituted or unsubstituted C$_{1-6}$ alkyl.

More particularly, in some embodiments, at least one of A or E is:

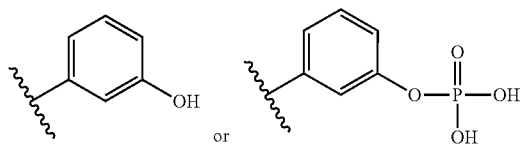 [SMILES: *c1cccc(O)c1 ; *c1cccc(OP(=O)(O)O)c1]

In another embodiment of the lipid A mimics of formula A-L$_1$-D-L$_2$-E, at least one of A or E is:

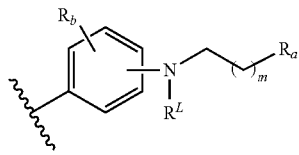

wherein:

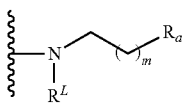

is placed at any position on the benzene ring;
R$_a$ is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6; m is 0-6;
R$^L$ is a lipid chain substituent; and
R$_b$ is placed at any remaining position on the benzene ring and is —H, —OH, —Cl, —Br, —F, —COOH, —CN, —SO$_3$H, —OCH$_3$, —NO$_2$ or any substituted or unsubstituted C$_{1-6}$ alkyl.

In some embodiments of the lipid A mimics of formula A-L$_1$-D-L$_2$-E, E is an aromatic group and A is:

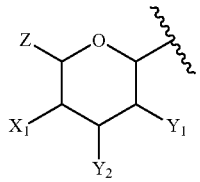

wherein:
Z is —CH$_2$G or —CH$_2$MQ, wherein G is —H, -halogen, —OH, —NH$_2$, —COOH, —OSO$_3$H, —SO$_3$H, —P(O)(OH)$_2$, or —OP(O)(OH)$_2$; M is —O—, —S—, —NH—, —OC(=O)—, —SC(=O)—, —OC(=S)—, or —NHC(=O)—; and Q is —H or a substituted or unsubstituted, branched or linear, saturated or unsaturated C$_{1-20}$ aliphatic hydrocarbon;
X$_1$ is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6; and
Y$_1$ and Y$_2$ are independently —H, —OH, —O—R$^L$, —NH—R$^L$, or —S—R$^L$, wherein R$^L$ is a lipid chain substituent.

More particularly, in some embodiments where A is as defined immediately above, X$_1$ is —OP(O)(OH)$_2$; Y$_1$ is —NH—R$^L$; and Y$_2$ is —O—R$^L$.

In other embodiments of the lipid A mimics of formula A-L$_1$-D-L$_2$-E, A is an aromatic group and E is:

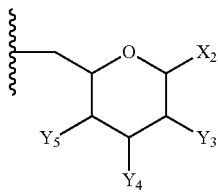

wherein:
X$_2$ is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6; and
Y$_3$, Y$_4$ and Y$_5$ are independently —H, —OH, —O—R$^L$, —NH—R$^L$, or —S—R$^L$, wherein R$^L$ is a lipid chain substituent.

More particularly, in some embodiments where E is as defined immediately above, X$_2$ is —OP(O)(OH)$_2$; Y$_3$ is —NH—R$^L$; Y$_4$ is —O—R$^L$; Y$_4$ is —O—R$^L$; and Y$_5$ is —OH.

In some embodiments, L$_1$ is present as defined by II below, and may be incorporated into formula A-L$_1$-D-L$_2$-E as follows:

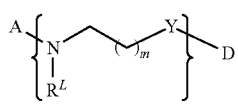

II wherein m is 0-6, Y is —(CO)$_f$—, wherein f is 0 or 1, and R$^L$ is a lipid chain substituent.

In some embodiments, $L_2$ is present as defined by I below, and may be incorporated into formula $A-L_1-D-L_2-E$ as follows:

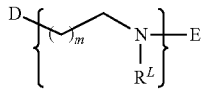

I wherein m is 0-6 and $R^L$ is a lipid chain substituent.

In an embodiment, there is provided a lipid A mimic that is a compound of formula:

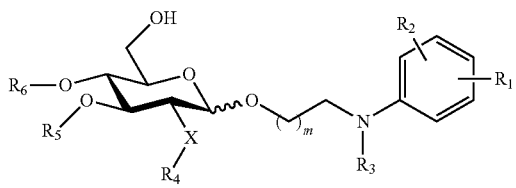

wherein:
the glycosidic linkage is α or β;
X is O or NH;
m is 0-6;
$R_1$ is placed in ortho-, meta-, or para-position to the N-substituent on the benzene ring and is —H, —OH, —OP(O)(OH)$_2$, —COOH, —SO$_3$H, —(O)$_k$(CH$_2$)$_n$COOH or —(O)$_k$(CH$_2$)$_q$OP(O)(OH)$_2$; wherein k is 0 or 1, n is 0-4, and q is 2-6;
$R_2$ is placed at any remaining position of the benzene ring and is —H, —OH, —Cl, —Br, —F, —COOH, —CN, —SO$_3$H, —OCH$_3$, —NO$_2$, or a $C_{1-6}$ alkyl optionally substituted or unsubstituted;
$R_3$, $R_4$, and $R_5$ are each independently a lipid chain substituent; and
$R_6$ is —H, —P(O)(OH)$_2$, or —CH$_2$COOH,
or a pharmaceutically acceptable salt thereof.

In another embodiment, there is provided a lipid A mimic that is a compound of formula:

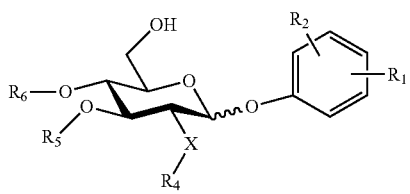

wherein:
the glycosidic linkage is α or β;
X is O or NH;
$R_1$ is placed in ortho-, meta-, or para-position to the N-substituent on the benzene ring and is:

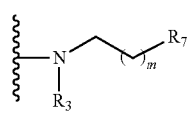

$R_7$ is —H, —OH, —OP(O)(OH)$_2$, —COOH, —SO$_3$H, —(O)$_k$(CH$_2$)$_n$COOH, or —(O)$_k$(CH$_2$)$_q$OP(O)(OH)$_2$; wherein k is 0 or 1, n is 0-4, and q is 2-6;
m is 0-6;
$R_2$ is placed at any remaining position of the benzene ring and is —H, —OH, —Cl, —Br, —F, —COOH, —CN, —SO$_3$H, —OCH$_3$, —NO$_2$, or a $C_{1-6}$ alkyl optionally substituted or unsubstituted;

$R_3$, $R_4$, and $R_5$ are each independently a lipid chain substituent; and
$R_6$ is —H, —P(O)(OH)$_2$, or —CH$_2$COOH,
or a pharmaceutically acceptable salt thereof.

In another embodiment, there is provided a lipid A mimic that is a compound of formula:

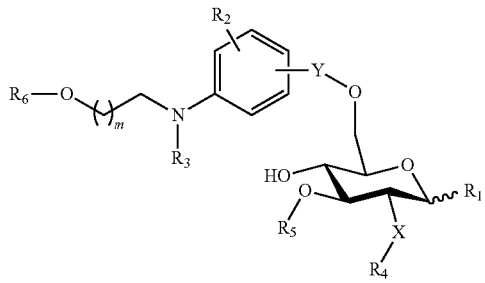

wherein:
the glycosidic linkage is α or β;
X is O or NH;
m is 0-6;
Y is placed in ortho-, meta-, or para-position to the N-substituent on the benzene ring and is —(O)$_g$(CH$_2$)$_h$(CO)$_j$—, wherein g is 0 or 1, h is 0-6, and j is 0 or 1;
$R_2$ is placed at any remaining position of the benzene ring and is —H, —OH, —Cl, —Br, —F, —COOH, —CN, —SO$_3$H, —OCH$_3$, —NO$_2$, or a $C_{1-6}$ alkyl optionally substituted or unsubstituted;
$R_1$ is —H, —OH, —OP(O)(OH)$_2$, —COOH, —SO$_3$H, —(O)$_k$(CH$_2$)$_n$COOH, or —(O)$_k$(CH$_2$)$_q$OP(O)(OH)$_2$; wherein k is 0 or 1, n is 0-4, and q is 2-6;
$R_3$, $R_4$, and $R_5$ are each independently a lipid chain substituent; and
$R_6$ is —H, —P(O)(OH)$_2$, or —CH$_2$COOH,
or a pharmaceutically acceptable salt thereof.

In another embodiment, there is provided a lipid A mimic that is a compound of formula:

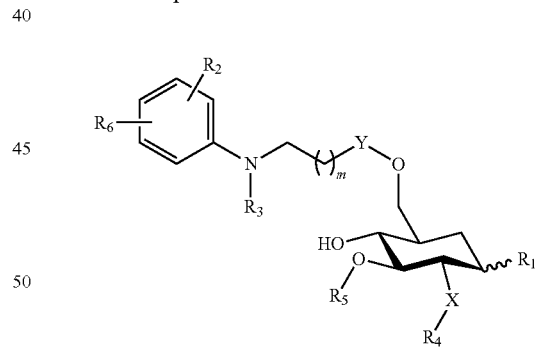

wherein:
the glycosidic linkage is α or β;
X is O or NH;
m is 0-6;
$R_6$ is placed in ortho-, meta-, or para-position to the N-substituent on the benzene ring and is —H, —OH, —OP(O)(OH)$_2$, —COOH, —SO$_3$H, —(O)$_k$(CH$_2$)$_n$COOH, or —(O)$_k$(CH$_2$)$_q$OP(O)(OH)$_2$; wherein k is 0 or 1, n is 0-4, and q is 2-6;
$R_2$ is placed at any remaining position of the benzene ring and is —H, —OH, —Cl, —Br, —F, —COOH, —CN, —SO$_3$H, —OCH$_3$, —NO$_2$, or a $C_{1-6}$ alkyl optionally substituted or unsubstituted; Y is —(CO)$_f$—, wherein f is 0 or 1;

$R_1$ is —H, —OH, —OP(O)(OH)$_2$, —COOH, —SO$_3$H, —(O)$_k$(CH$_2$)$_n$COOH, or —(O)$_k$(CH$_2$)$_q$OP(O)(OH)$_2$; wherein k is 0 or 1, n is 0-4, and q is 2-6; and $R_3$, $R_4$, and $R_5$ are each independently a lipid chain substituent, or a pharmaceutically acceptable salt thereof.

In an embodiment, there is provided a lipid A mimic designated JL-265 having a structure as shown below:

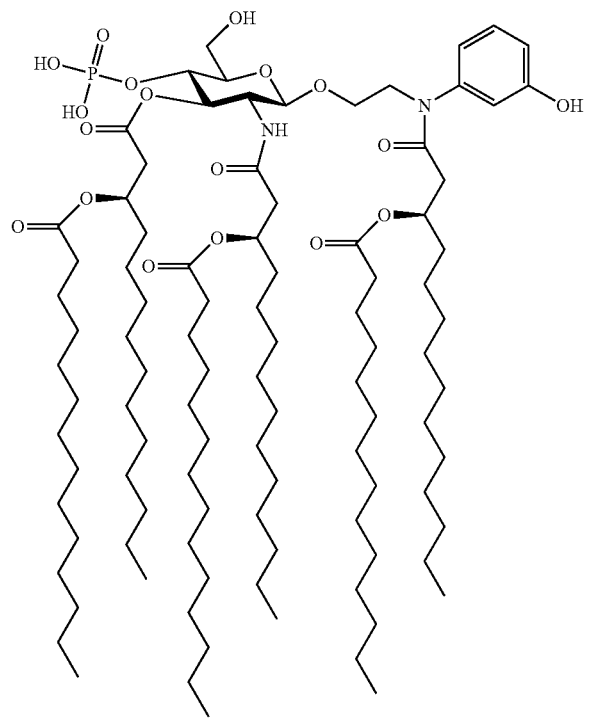

or a pharmaceutically acceptable salt thereof.

In an embodiment, there is provided a lipid A mimic designated JL-266 having a structure as shown below:

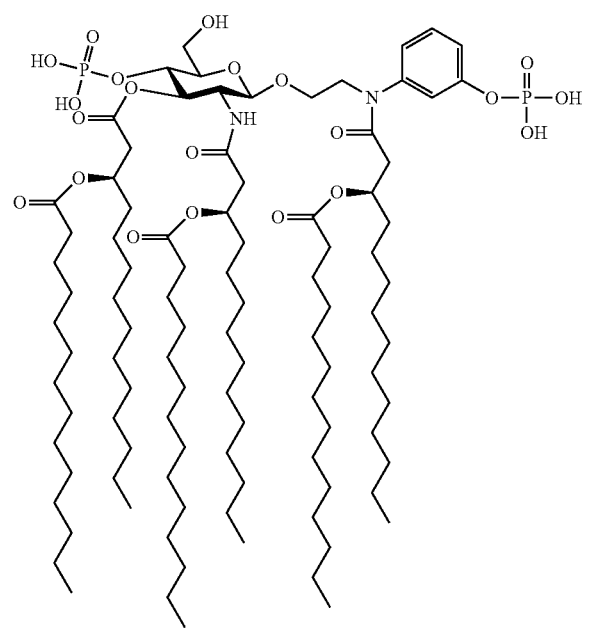

or a pharmaceutically acceptable salt thereof.

In some embodiments, the lipid A mimics as disclosed herein may have lipid A or lipopolysaccharide (LPS) antagonist activity.

In some embodiments, the lipid A mimics as disclosed herein may have immunostimulatory activity.

In some embodiments, the lipid A mimics as disclosed herein may be capable of binding to toll-like receptor 4 (TLR4).

In another aspect, a lipid A mimic as disclosed herein may be formulated as a pharmaceutical composition comprising the lipid A mimic, or pharmaceutically acceptable salt thereof, and a pharmaceutically acceptable carrier, diluent or excipient.

In another aspect, a lipid A mimic as disclosed herein may be formulated as a vaccine composition comprising the lipid A mimic, or pharmaceutically acceptable salt thereof, and an antigen.

In an embodiment, the vaccine composition may further comprise liposomes; a carrier comprising a continuous phase of a hydrophobic substance; and T-helper epitope.

In an embodiment, the vaccine composition is formulated in DepoVax™.

In an embodiment, the lipid A mimic included in the pharmaceutical or vaccine composition as described herein is JL-265 or JL-266.

In another aspect, the pharmaceutical composition as described herein may be useful in a method for treating or preventing a lipopolysaccharide (LPS)/lipid A-mediated disease or disorder in a subject, said method comprising administering to the subject the pharmaceutical composition.

In another aspect, the vaccine composition as described herein may be useful in a method for inducing or potentiating an antibody and/or cell-mediated immune response against an antigen in a subject, said method comprising administering to the subject the vaccine composition.

In another aspect, the vaccine composition as described herein may be useful in a method for treating or preventing cancer, said method comprising administering to the subject the vaccine composition.

In another aspect, the vaccine composition as described herein may be useful in a method for treating or preventing an infectious disease, said method comprising administering to the subject the vaccine composition.

In another aspect, the vaccine composition as described herein may be useful in a method for treating or preventing an addiction disease, said method comprising administering to the subject the vaccine composition.

In another aspect, the pharmaceutical composition as described herein may be for use in the treatment or prevention of a lipopolysaccharide (LPS)/lipid A-mediated disease or disorder in a subject.

In another aspect, the vaccine composition as described herein may be for use in inducing or potentiating an antibody and/or cell-mediated immune response against an antigen in a subject; or for treating or preventing cancer, an infectious disease, or an addiction disease in a subject.

In an embodiment, the subject referred to herein is a mammal. In a more particular embodiment, the subject is a human, According to another aspect, there is provided a method of preparing the lipid A mimics as disclosed herein.

Other aspects and features of the present invention will become apparent to those of ordinary skill in the art upon review of the following description in conjunction with the accompanying figures.

BRIEF DESCRIPTION OF THE FIGURES

In the figures, which illustrate embodiments of the invention by way of example only.

DETAILED DESCRIPTION

Lipopolysaccharide (LPS), also known as endotoxin, is the outer membrane component of Gram-negative bacteria. LPS has been described as a potent immunostimulant. The active component of LPS for its immunostimulatory activity has been determined to be the lipophilic anchor of the molecule, known as lipid A.

Figure 1:
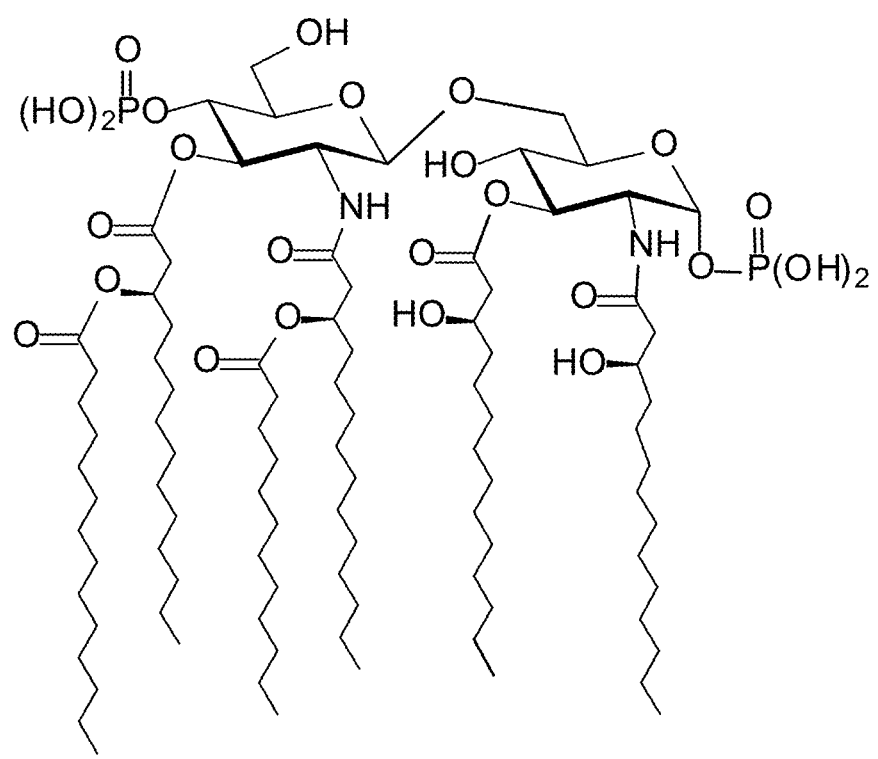
FIG. 1 illustrates the structure of E. coli lipid A.

The core structure of lipid A is conserved regardless of bacterial species, and consists of a β-(1-6) glycosidically linked di-D-glucosamine backbone bisphosphorylated at the 1-O- and 4'-O-position, for example, Escherichia coli lipid A (FIG. 1). This disaccharide core is acylated with up to seven lipid chains through both ester and amide linkages, with differences in the number, length, and composition of said chains.

Lipid A preparations purified from bacterial cultures are structurally heterogeneous; thus, they suffer from lack of consistency both in composition and performance. Its heterogeneity is the cause of large batch-to-batch variations both in composition and activity, which makes regulatory approval difficult. In contrast, synthetic lipid A analogues or mimics are structurally defined pure single molecules, which may potentially be advantageous in achieving reproducibility and consistency with respect to product manufacturing and performance. Chemical synthesis may also allow for fine-tuning of the activity/toxicity profile of adjuvant candidates. In fact, significant effort has been directed towards synthetic lipid A analogues or mimics in order to develop new vaccine adjuvants.

Currently, there are a few lipid A-based structures that are in clinical evaluations as adjuvants (Fox et al., Subcellular Biochemistry, 53: 303-321, 2010). Also, monosaccharide lipid A analogues wherein the reducing end glucosamine residue is replaced by a non-sugar structural element have been reported to show potent immunostimulatory activity. In particular, Johnson et al. have reported a group of aminoalkylglucosaminyl glycoside lipid A analogues (Johnson et al., Bioorganic & Medicinal Chemistry Letters, 9: 2273-2278, 1999). Jiang et al. have reported a group of lipid A analogues derived from pentaerythritol (Jiang et al., Tetrahedron, 58: 8833-8842, 2002) and diethanolamine (Lewicky et al., RSC Adv., 2: 1917-1926, 2012; Lewicky et al., Bioorg. Med. Chem., 21: 2199-2209, 2013). Moreover, lipid A analogues are known in which the entire disaccharide unit has been replaced with an acyclic backbone (Hawkins, J. Pharmacol. Exp. Therap. 300: 655-61, 2002).

The present invention relates to novel synthetic structural mimics of lipid A, including for example *E. coli* lipid A, methods of synthesizing such mimics, and uses thereof. The lipid A mimics of the present invention replace one or both of the sugar residues of a natural lipid A with an aromatic group. The lipid A mimics disclosed herein may be agonists or antagonists of native bacterial lipid A.

Definitions

The terms "aliphatic hydrocarbon" or "aliphatic group" (used interchangeably) refer to a hydrocarbon compound containing carbon and hydrogen joined together in straight chains, branched chains or non-aromatic rings.

The term "alkyl", by itself or as part of another substituent, refers to, unless otherwise stated, a straight or branched chain, saturated or unsaturated, substituted or unsubstituted, aliphatic group having any number of carbons, such as for example 1 to 20 carbon atoms, and more particularly having the number of carbon atoms as designated (e.g. $C_{1-6}$ meaning 1 to 6 carbon atoms).

The term "alkoxy" refers to an aliphatic hydrocarbon singular bonded to oxygen (R—O). An alkoxy group bonded to an alkyl (R—O—R) forms an ether. If bonded to hydrogen, it forms an alcohol (R—OH).

The term "alkene" refers to an unsaturated aliphatic hydrocarbon containing at least one carbon-carbon double bond. As a functional group it may be referred to herein also as "alkenyl". The term "dialkenyl" is used herein to represent an unsaturated aliphatic hydrocarbon group containing at least two carbon-carbon double bonds.

The term "alkyne" refers to an unsaturated aliphatic hydrocarbon containing at least one carbon-carbon triple bond. As a functional group it may be referred to herein also as "alkynyl".

Unless specifically stated otherwise, for any of the alkyl, alkoxy, alkene, or alkyne substituent groups described herein, it is possible that one or more of the carbon atoms in the carbon chain may be replaced with a heteroatom (e.g. nitrogen, oxygen or sulfur).

The terms "carbonyl" and "oxo", as used herein, refer to a (C=O) moiety. A carbonyl group may also be represented as —C(O)—.

The expression "one or more" is used interchangeably herein with the expression "at least one". These expressions, unless explicitly stated otherwise herein, refer to the number of different entities (e.g. number of different lipid A mimics; number of different antigens, etc.), and not to the quantity of any particular entity, in accordance with the ordinary meaning of "at least one" or "one or more".

The expression "a subject in need thereof", as used herein, is meant to encompass not only a subject who has a particular disease, disorder or condition, but also a subject who may potentially contract the disease, disorder or condition or who may potentially be exposed to a substance that may cause the disease, disorder or condition. This is particularly relevant to vaccine compositions as disclosed herein since treatment with a vaccine is often prophylactic (e.g. given to prevent or ameliorate the effects of a potential future infection, possibly irrespective of whether the subject is or is not at risk of being infected).

Lipid A Mimics

The lipid A mimics of the present invention replace one or both of the sugar residues of a natural lipid A with an aromatic group. These lipid A mimics may also be characterized by additional differences from the natural lipid A, such as a different number of phosphate groups present, changes in the number, structure and location of lipid chains, changes in the spacing and linkage of the sugar residues (or their aromatic replacements), as well as the replacement of one or both phosphate groups with its bioisosteres or other substituents (e.g., a carboxylic, a sulphate group, a hydroxyl group, or a hydrogen).

In an embodiment, the lipid A mimics of the present invention are compounds described generally by the following formula:

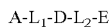

wherein:

A is a cyclic monosaccharide residue with one or more of the hydroxyl groups optionally substituted or absent, or A is a substituted or unsubstituted aromatic group;

$L_1$ and $L_2$ independently are present or absent, and if present is independently a substituted or unsubstituted, branched or linear, saturated or unsaturated, carbon chain optionally comprising one or more of O, S or N;

D is —O—, —S— or —NH—; and

E is a cyclic monosaccharide residue with one or more of the hydroxyl groups optionally substituted or absent, or E is a substituted or unsubstituted aromatic group;

wherein at least one of A or E is a substituted or unsubstituted aromatic group, or a pharmaceutically acceptable salt thereof.

In general, to preserve structural similarity to natural lipid A, the following further features may be present in the lipid A mimics of the invention:

(1) at least one of A or E comprises at least one phosphate group or phosphate group equivalent;

(2) at least one of A, $L_1$, $L_2$, or E comprises at least one lipid chain substituent; more particularly, at least one of A or $L_1$ comprises one or more lipid chain substituents and at least one of E or $L_2$ comprises one or more lipid chain substituents.

From the above, it can be seen that the lipid A mimics of the invention may comprise at least four major elements: an aromatic group; a sugar residue (cyclic monosaccharide); a phosphate group or phosphate group equivalent, and a lipid chain substituent. However, it is possible that one or more of these major elements is not present or that more than one of certain major elements may be present. In addition to the major elements, there may also be other elements such as linkers or spacers and substituent groups.

Linkers and spacers include, for example, the substituents identified as $L_1$ and $L_2$ in formula A-$L_1$-D-$L_2$-E. Substituent group D may also be considered a linker or spacer. In addition to these specific linkers or spacers, the lipid A mimics may also comprise further linkers or spacers such as, for example and without limitation, a linker or spacer connecting the lipid chain substituents and/or connecting the phosphate or phosphate group equivalents.

Any of the major elements of the lipid A mimics may be optionally substituted thereon, particularly the sugar residue (if present), aromatic group(s) and the lipid chain substituents. Exemplary embodiments of substituents are described herein without limitation. The substituents may be any organic group or moiety. As used herein, the term "organic group or moiety" refers to a substituent group having at least one carbon atom, and typically at least one C—H bond. The substituent group may comprise any number of oxygen, nitrogen, sulfur, phosphorus, halogen or other atoms.

Aromatic Group(s) of the Lipid A Mimics

An invariant structural feature of the natural lipid A molecule is its 13-(1-6)-linked D-glucosamine disaccharide backbone. The lipid A mimics of the present invention replace of one or both of the glucosamine sugar residues with an aromatic group.

Without being bound by theory, it is believed that the employment of an aromatic group to replace one or both of the glucosamine residues in natural lipid A brings about two unique structural features which may potentially be important to strengthen the binding between the lipid A mimic of the invention and its receptor, TLR4/MD-2. First, the aromatic group is a rigid system which may provide favourable free energy for binding. In other words, the less flexible molecule will potentially produce higher binding energy than its more flexible counterpart when all other parameters are identical. Second, aromatic groups comprise a flat electron-rich π-system, which may provide π-effects or π-interactions, a type of non-covalent interaction involving π systems. Non-covalent interactions involving t systems are pivotal to biological events such as protein-ligand interaction. Common π-interactions include aromatic-aromatic interaction (π stacking), C—H/π interaction, and anion-π interaction. Such π-interactions are not present for natural lipid A molecules or other synthetic analogues lacking an aromatic group. It is considered that the additional π-interactions potentially contribute to the binding affinity between the lipid A mimics of the invention and its receptor TLR4/MD-2, and thus the biological activity of these compounds may potentially be improved.

As used herein, the term "aromatic group" refers to a substituent group that comprises one or more aromatic rings. As such, the terms "aromatic group" and "aromatic ring" may be used interchangeably herein. If the aromatic group comprises more than one aromatic ring, the rings may be attached together in a pendent manner or may be fused. The term "aromatic group" encompasses carbocyclic aromatic groups (containing only carbon atoms in the aromatic ring or rings) and heteroaromatic groups (containing carbon and one or more other atoms in at least one of the aromatic rings).

Each carbocyclic aromatic group may have from 3 to 26 total carbon ring atoms and, in the case of a heteroaromatic group, may have from 3 to 26 total ring atoms with 1 to 6 ring atoms being selected from nitrogen, oxygen, sulfur, phosphorus, or selenium atoms.

Generally, the aromatic group substituents of the lipid A mimics of the invention abide by the criteria for aromaticity: (i) the group must be cyclic, (ii) every atom in the ring must have an occupied p orbital, which overlaps with p orbitals on either side (completely conjugated), (iii) the group must be planar, (iv) the group must contain an odd number of pairs of π electrons (i.e. must satisfy Hückel's rule: (4n+2) π electrons, where n is an integer starting at zero).

The term "carbocyclic aromatic group", as used herein, means an aromatic group having one or more carbon rings wherein such rings may be attached together in a pendent manner or may be fused. In particular embodiments, a carbocyclic aromatic group is one, two or three rings. Monocyclic embodiments may contain 4 to 10 carbon atoms, more particularly 4 to 7 carbon atoms, and even more particularly 6 carbon atoms in the ring. Bicyclic embodiments may contain 8 to 12 carbon atoms, more particularly 8 to 10, and even more particularly 10 carbon atoms in the rings. Tricyclic embodiments may contain 12 to 16 carbon atoms, and more particularly 14 carbon atoms in the rings. Examples of carbocyclic aromatic groups include, but are not limited to, benzene, naphthalene and anthracene:

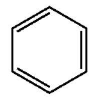

benzene 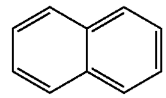 naphthalene 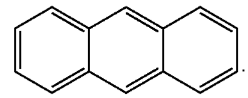 anthracene

With respect to the structures immediately above, it will be understood that one of the carbon ring atoms will be bonded to the remainder of the lipid A mimic (i.e. in formula $A-L_1-D-L_2-E$, it will be bonded to D or to one of $L_1$ or $L_2$). The other carbon atoms may be substituted or unsubstituted.

The term "heteroaromatic group", as used herein, means an aromatic group having one or more rings wherein such rings may be attached together in a pendent manner or may be fused, wherein the aromatic group has at least one heteroatom such as, for example, nitrogen, oxygen, sulfur, phosphorus, or selenium. Monocyclic embodiments may contain 4 to 10 member atoms, more particularly 4 to 7 member atoms, and even more particularly 5 or 6 member atoms in the ring. Bicyclic embodiments may contain 8 to 12 member atoms, more particularly 8 to 10 member atoms, and even more particularly 9 or 10 member atoms in the rings. Tricyclic embodiments may contain 12 to 16 member atoms, and more particularly 14 member atoms in the rings. Examples of heteroaromatic groups include, but are not limited to:

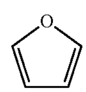

furan 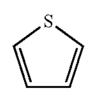 triophene 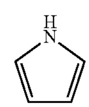 pyrrole 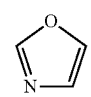 oxazole 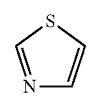 thiazole 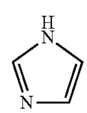 imidazole 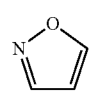 isoxazole 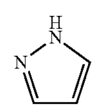 pyrazole 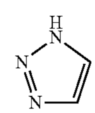 1H-1,2,3-triazole 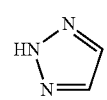 2H-1,2,3-triazole 1H-1,2,4-triazole 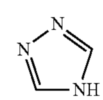 4H-1,2,4-triazole 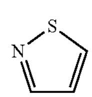 isothiazole 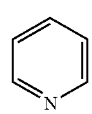 pyridine 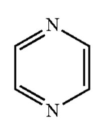 pyrazine 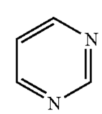 pyrimidine 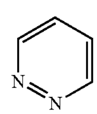 pyridazine 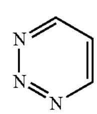 1,2,3-triazine 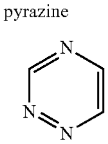 1,2,4-triazine 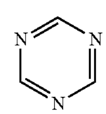 1,3,5-triazine benzofuran idole benzothiophene

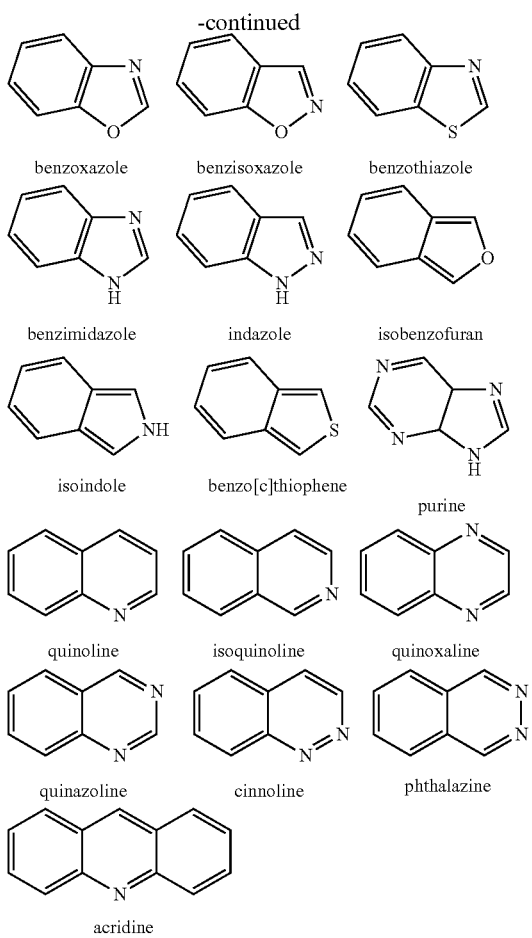

With respect to the structures immediately above, the aromatic group will be bonded to the remainder of the lipid A mimic (i.e. in formula A-L$_1$-D-L$_2$-E, it will be bonded to D or to one of L$_1$ or L$_2$) by a bond with one of the carbon atoms on the rings or with one of the heteroatoms on the rings. The other carbon atoms or heteroatoms may be substituted or unsubstituted.

In an embodiment, the aromatic group of the lipid A mimics is a carbocyclic aromatic group comprising one, two or three substituted or unsubstituted aromatic rings. In some embodiments, the aromatic group comprises only one substituted or unsubstituted aromatic ring, and in more particular embodiments the aromatic group is a substituted or unsubstituted benzene ring. As will be understood, when the benzene ring is bonded to the remainder of the lipid A mimic (i.e. in formula A-L$_1$-D-L$_2$-E it will be bonded to D or to one of L$_1$ or L$_2$), it can equally be referred to as a phenyl group. The carbon atoms on the ring of the phenyl group may optionally be substituted with one or more of the same or different substituents.

In the lipid A mimics of the invention, at least one of A or E is an aromatic group. In one embodiment, A is the aromatic group and E is a cyclic monosaccharide residue as defined later herein. In a second embodiment, E is the aromatic group and A is a cyclic monosaccharide residue as defined later herein. In a third embodiment, both A and E are aromatic groups and the lipid A mimic does not contain a cyclic monosaccharide residue. In this third embodiment, A and E may be the same or different aromatic group, and in either embodiment each aromatic group may independently have the same or different substituents, or no substituents at all.

To preserve structural similarity to natural lipid A, embodiments of the invention may only have one of A or E replaced with an aromatic group such that the lipid A mimic maintains a cyclic monosaccharide residue. In a particular embodiment, it is E that is replaced with an aromatic group and that aromatic group is a benzene ring.

As mentioned, the aromatic groups may be optionally substituted by one or more identical or different groups. Without limitation, the substitutions may be selected from a halogen atom such as, for example, fluorine (—F), chlorine (—Cl), bromine (—Br), or iodine (—I); —OH; —NH$_2$; —COOH; —CN; —SO$_3$H; —OCH$_3$; —NO$_2$; a substituted or unsubstituted, linear or branched C$_{1-10}$ alkyl group; a substituted or unsubstituted, linear or branched C$_{1-10}$ alkoxy group; a substituted or unsubstituted, linear or branched C$_{2-10}$ alkene group; or a substituted or unsubstituted, linear or branched C$_{2-10}$ alkyne group. For any of the alkyl, alkoxy, alkene, or alkyne group substituents, it is possible that one or more of the carbon atoms in the carbon chain may be replaced with a nitrogen, oxygen or sulfur atom. The substitution positions of the substituent on the aromatic group are not particularly limited as far as it can be substituted thereon.

In addition or in alternative to the substituents described above, the aromatic group may be optionally substituted with any one or more of the phosphate group or phosphate group equivalents as defined later herein; or with any one or more of the lipid chain substituents as defined later herein. Again, the substitution positions of the substituent on the aromatic group are not particularly limited as far as it can be substituted thereon.

In an exemplary embodiment of the lipid A mimics of the invention, at least one of A or E in formula A-L$_1$-D-L$_2$-E, is:

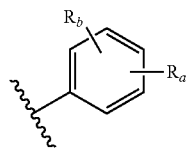

wherein:

R$_a$ is present or absent and if present is placed at any position on the benzene ring and is a phosphate or phosphate group equivalent as defined later herein; and R$_b$ is present or absent and if present is placed at any remaining position on the benzene ring and is a halogen atom; —OH; —NH$_2$; —COOH; —CN; —SO$_3$H; —OCH$_3$; —NO$_2$; a substituted or unsubstituted, linear or branched C$_{1-10}$ alkyl group; a substituted or unsubstituted, linear or branched C$_{1-10}$ alkoxy group; a substituted or unsubstituted, linear or branched C$_2$-10 alkene group; or a substituted or unsubstituted, linear or branched C$_{2-10}$ alkyne group.

In more particular embodiments of the structure above, R$_a$ is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6. In some embodiments, R$_a$ is —H, —OH or —OP(O)(OH)$_2$. For R$_b$, more particular embodiments include —H, —OH, —NH$_2$, —Cl, —Br, —F, —COOH, —CN, —SO$_3$H, —OCH$_3$, —NO$_2$ or any substituted or unsubstituted C$_{1-6}$ alkyl. In some embodiments, R$_b$ is —H.

The structure above may be of particular interest for substituent E in the lipid A mimics of the invention when: A is a cyclic monosaccharide residue (e.g. glucosamine), $L_1$ is absent, D is O, and $L_2$ is present and comprises a lipid chain substituent as defined herein. In an opposite configuration, the structure above may alternatively be of particular interest for substituent A in the lipid A mimics, when: E is a cyclic monosaccharide residue (e.g. glucosamine), $L_2$ is absent, D is O, and $L_1$ is present and comprises a lipid chain substituent as defined herein. In each of these embodiments, A or E may be selected from one of the following structures:

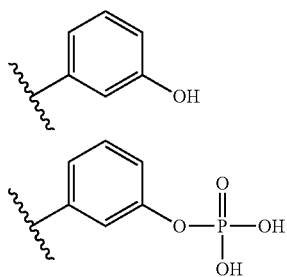

In another exemplary embodiment of the lipid A mimics of the invention, at least one of A or E in formula A-$L_1$-D-$L_2$-E, is:

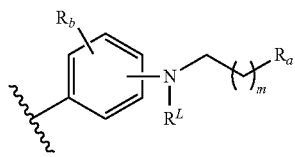

wherein:

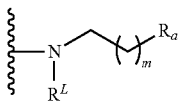

is placed at any position on the benzene ring;
$R_a$ is as defined earlier herein and in particular embodiments is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6;
$R_b$ is present or absent and if present is placed at any remaining position on the benzene ring and is as defined earlier herein, such as for example, —H, —OH, —NH$_2$, —Cl, —Br, —F, —COOH, —CN, —SO$_3$H, —OCH$_3$, —NO$_2$ or any substituted or unsubstituted $C_{1-6}$ alkyl;
m is 0-6;
$R^L$ is a lipid chain substituent as defined later herein.

The structure above may be of particular interest for substituent E in the lipid A mimics of the invention when: A is a cyclic monosaccharide residue (e.g. glucosamine), $L_1$ is absent, D is O, and $L_2$ is absent. In an opposite configuration, the structure above may alternatively be of particular interest for substituent A in the lipid A mimics, when: E is a cyclic monosaccharide residue (e.g. glucosamine), $L_2$ is absent, D is O, and $L_1$ is absent.

It is possible that there may be more aromatic groups in the lipid A mimic than those used to replace one or both sugar residues of natural lipid A. Such "additional" aromatic groups may be useful for the attachment of phosphate or phosphate equivalent groups, lipid chain substituents, or other useful chemical moieties. There may also be aromatic groups as substituents on the lipid chain substituents. Generally, there can be up to six "additional" aromatic groups. In some embodiments, there is just one "additional" aromatic group. In other embodiments, there are no "additional" aromatic groups.

Sugar Residue of the Lipid A Mimics

Natural lipid A is a disaccharide. The lipid A mimics of the present invention replace of one or both of the sugar residues of a natural lipid A with an aromatic group. The remaining sugar residue may be retained (possibly in a modified form), likewise replaced with an aromatic group, or omitted altogether from the lipid A mimics of the present invention. If the lipid A mimic includes a sugar residue, it need not be the same sugar residue as in natural lipid A, i.e. glucosamine. The remaining sugar residue, if present, may be a natural sugar residue of lipid A, a different sugar residue, or a modified form thereof. For example, in an embodiment, the sugar residue can be any cyclic monosaccharide, including the derivatives or modified versions of cyclic monosaccharides contemplated herein.

As used herein, the term "cyclic monosaccharide residue" refers to a chemical moiety in the lipid A mimics of the invention where the backbone structure of the moiety is that of a cyclic monosaccharide or a derivative or modified version thereof, including for example a cyclic hemiacetal or hemiketal. The term cyclic monosaccharide may be used interchangeably herein with "sugar residue". By cyclic monosaccharide, it is meant that the moiety minimally comprises a ring of carbon atoms closed by one bridging oxygen atom, with each respective carbon atom bonded to a hydroxyl group. Thus, the term "cyclic monosaccharide residue", as used herein, refers not only to the backbone ring of the sugar residue, but also the hydroxyl group attached at each carbon atom. In the lipid A mimics of the invention, one or more of the hydroxyl groups may be optionally substituted or absent.

Cyclic monosaccharides with a three membered ring are oxiroses; with four, oxetoses; with five, furanoses; with six, pyranoses; with seven, septanoses; with eight, octanoses; and so forth. The locants of the positions of ring closure may vary. In the more common cyclic monosaccharides, the ring includes one oxygen atom, with the remaining ring atoms being carbon. In an embodiment of the lipid A mimics of the invention, the remaining sugar residue or modified form thereof (if present), typically comprises a five- or six-membered ring, such as a furanose ring or a pyranose ring, respectively:

 

furansose ring  pyranose ring

The furanose or pyranose ring may be linked, directly or indirectly, to the aromatic group of the lipid A mimic of the invention at any one of the carbon atoms on the ring, and the remaining positions on the ring may be unsubstituted or substituted with any other chemical moiety. Particular substitutions are described later herein and include, for example, the addition of lipid chains, phosphate or phosphate group equivalents, or other substituent groups.

The cyclic monosaccharide or modified version thereof may be a deoxy sugar (alcoholic hydroxy group replaced by hydrogen), amino sugar (alcoholic hydroxy group replaced by amino group), a thio sugar (alcoholic hydroxy group replaced by thiol, or C=O replaced by C=S, or a ring oxygen of cyclic form replaced by sulfur), a seleno sugar, a telluro sugar, an aza sugar (ring carbon replaced by nitrogen), an imino sugar (ring oxygen replaced by nitrogen), a phosphano sugar (ring oxygen replaced with phosphorus), or a phospha sugar (ring carbon replaced with phosphorus), and so forth. Amino sugars include glycosylamines, in which the hemiacetal hydroxy group is replaced.

Derivatives of these structures include O-substituted derivatives, in which the hydroxy hydrogen is replaced by something else. Without limitation, possible replacements include alkyl, acyl, phosphate or phosphate group equivalents as defined herein, phosphonate, phosphinate, sulphate, lipid chain substituents as defined herein, or other substituents. Likewise, derivatives of amino sugars include N-substituted derivatives, and derivatives of thio sugars include S-substituted derivatives.

To preserve structural similarity to natural lipid A, embodiments of the invention may include a pyranose ring in the position of the remaining sugar residue. In a particular embodiment, the remaining sugar residue is represented by the following general formula:

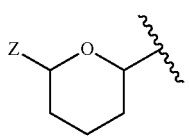

wherein Z is —H, —OH, —CH$_2$G or —CH$_2$MQ, wherein G is —H, -halogen, —OH, —NH$_2$, —COOH, —OSO$_3$H, —SO$_3$H, —P(O)(OH)$_2$, or —OP(O)(OH)$_2$; M is —O—, —S—, —NH—, —OC(=O)—, —SC(=O)—, —OC(=S)—, or —NHC(=O)—; and Q is —H or a substituted or unsubstituted, branched or linear, saturated or unsaturated C$_{1-20}$ aliphatic hydrocarbon;

represents the position of the bond linkage to the aromatic group of the lipid A mimics of the invention; and any remaining position on the pyranose ring may be substituted or unsubstituted as described herein.

To further preserve structural similarity to natural lipid A, embodiments of the invention may include a pyranose sugar residue as the remaining sugar residue. As used herein, the term "pyranose sugar residue" refers not only to the backbone ring of the sugar residue, but also the hydroxyl group attached at each carbon atom. A pyranose sugar residue includes, for example, any cyclic isomer of a hexose sugar, such as the pyranose form of allose, altrose, glucose, mannose, gulose, iodose, galactose or talose. The general structure of the pyranose sugar residue, without any substitutions and without any stereochemistry, is depicted by the following formula:

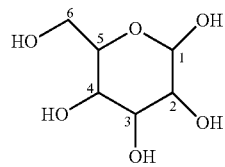

In the lipid A mimics of the invention, one or more of the hydroxyl groups may be optionally substituted or absent.

In particular embodiments, the pyranose sugar residue in the lipid A mimics of the invention comprises a glucopyranose ring or a galactopyranose ring with one or more of the hydroxyl groups optionally substituted or absent. By reference to glucopyranose and galactopyranose, it is meant to define the alternate arrangements of the chemical moiety (i.e. hydroxyl or any substituent as defined herein) attached at the C-4 position (i.e. epimers). In a particular embodiment, the pyranose sugar residue comprises a glucopyranose ring with one or more of the hydroxyl groups optionally substituted or absent. The glycosidic linkage between the sugar residue and the substituent attached thereto can be α or β.

Turning specifically to substituent A in formula A-L$_1$-D-L$_2$-E of the lipid A mimics of the invention, when A is not replaced with an aromatic group, this substituent may, without limitation, be represented by the following formula:

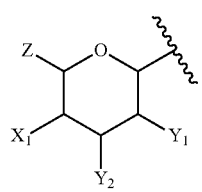

wherein:
Z is —CH$_2$G or —CH$_2$MQ, wherein G is —H, -halogen, —OH, —NH$_2$, —COOH, —OSO$_3$H, —SO$_3$H, —P(O)(OH)$_2$, or —OP(O)(OH)$_2$; M is —O—, —S—, —NH—, —OC(=O)—, —SC(=O)—, —OC(=S)—, or —NHC(=O)—; and Q is —H or a substituted or unsubstituted, branched or linear, saturated or unsaturated C$_{1-20}$ aliphatic hydrocarbon;
X$_1$ is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6; and
Y$_1$ and Y$_2$ are independently —H, —OH, —O—R$^L$, —NH—R$^L$, or —S—R$^L$, wherein R$^L$ is a lipid chain substituent as defined herein.

To preserve structural similarity to natural lipid A, in a particular embodiment of the lipid A mimics of the invention, Z is —CH$_2$OH, X$_1$ is —OP(O)(OH)$_2$, Y$_1$ is —NH—R$^L$ and Y$_2$ is —O—R$^L$, wherein R$^L$ is a lipid chain substituent as defined herein. Also, without limitation, the stereochemistry of the substitutions on A may be defined by the following formula:

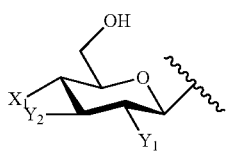

wherein $X_1$, $Y_1$ and $Y_2$ are as defined herein.

Turning specifically to substituent E in formula $A-L_1-D-L_2-E$ of the lipid A mimics of the invention, when E is not replaced with an aromatic group, this substituent may, without limitation, be represented by the following formula:

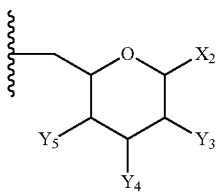

wherein:

$X_2$ is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6; and $Y_3$, $Y_4$ and $Y_5$ are independently —H, —OH, —O—R$^L$, —NH—R$^L$, or —S—R$^L$, wherein R$^L$ is a lipid chain substituent.

To preserve structural similarity to natural lipid A, in a particular embodiments of the lipid A mimics of the invention, $X_2$ is —OP(O)(OH)$_2$, $Y_3$ is —NH—R$^L$, and $Y_4$ is —O—R$^L$ and $Y_5$ is —OH, wherein R$^L$ is a lipid chain substituent as defined herein. Also, without limitation, the stereochemistry of the substitutions on E may be defined by the following formula:

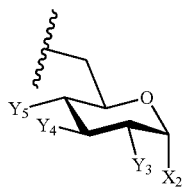

wherein $X_2$, $Y_3$, $Y_4$ and $Y_5$ are as defined herein.

Phosphate Group or Phosphate Group Equivalent of the Lipid A Mimics

Natural Lipid A includes two phosphate groups, each attached directly to a separate sugar residue of the disaccharide backbone. The recently approved monophosphoryl lipid A (MPL®), developed by GlaxoSmithKline, has been found to have reduced toxicity as compared to the natural diphosphorylated lipid A, while the immunostimulatory activity largely remains. In some embodiments of the lipid A mimics of the invention, one or more of the phosphate groups as found in natural lipid A may be omitted (i.e. replaced with hydrogen), replaced with another chemical moiety (e.g. hydroxyl), or replaced with a phosphate group equivalent.

As used herein, the term "phosphate group equivalent" refers generally to a bioisostere of the phosphate group. A "bioisostere" represents the replacement of a chemical moiety (i.e. an atom or a group of atoms) with an alternative, broadly similar, chemical moiety. The objective of a bioisosteric replacement is to create a compound with similar biological properties to the parent compound in all aspects (e.g. immunostimulatory activity, toxicity, pyrogenicity, etc) or in only some aspects, with other aspects being altered. A "phosphate group equivalent", as used herein, can contain a phosphate group (i.e. —OP(O)(OH)$_2$), so long as it is no longer directly attached to the sugar residue (or the aromatic group replacement).

Some examples of phosphate group equivalents include, without limitation, —P(O)(OH)$_2$, —COOH, —SO$_3$H, —OSO$_3$H, —CH(COOH)$_2$, —OB(OH)$_2$, —OP(O)(OH)—O—P(O)(OH)$_2$, —(O)$_k$(CH$_2$)$_n$COOH, —(O)$_k$(CH$_2$)$_n$SO$_3$H, —(O)$_k$(CH$_2$)$_n$P(O)(OH)$_2$, —(O)$_k$(CH$_2$)$_q$OCOOH, —(O)$_k$(CH$_2$)$_q$OSO$_3$H, —(O)$_k$(CH$_2$)$_q$OP(O)(OH)$_2$, wherein k is 0 or 1, n is 0-6 and q is 1-6. These represent examples of phosphate group equivalents where the phosphate equivalent is essentially a terminal moiety.

Other possible examples of phosphate group equivalents include, without limitation, —OP(O)(OH)OR$^P$, —P(O)(OH)OR$^P$, —OC(═O)OR$^P$, —C(═O)OR$^P$, —S(═O)$_2$OR$^P$, —OS(═O)$_2$OR$^P$, —OB(OH)OR$^P$ or —OP(O)(OH)—O—P(O)(OH)OR$^P$, where R$^P$ is a substituted or unsubstituted alkyl group of 1-4 carbons. If R$^P$ is a substituted alkyl group, then the substitutions are in some embodiments selected from —OH or —NH$_2$. An R$^P$ group of particular interest is —CH$_2$CH$_2$NH$_2$. In a particular embodiment, the phosphate equivalent group may be —OP(O)(OH)(OCH$_2$CH$_2$NH$_2$), wherein k is 0 or 1, n is 0-6 and q is 1-6. These represent examples of phosphate group equivalents where the phosphate equivalent may not be a terminal moiety in view of the inclusion of R$^P$.

In one embodiment of the lipid A mimics of the invention, both A and E in formula $A-L_1-D-L_2-E$ comprise a phosphate group attached directly thereto. By "directly thereto", it is meant that the phosphate group is bonded directly to the sugar residue or the aromatic group without any intervening chemical structure. It is possible that in these embodiments, one or both of A and E may additionally comprise one or more phosphate group equivalents.

In another embodiment of the lipid A mimics of the invention, only one of A or E in formula $A-L_1-D-L_2-E$ comprises a phosphate group attached directly thereto. On the other of A or E, the phosphate group has in some embodiments been replaced with —H, —OH or a phosphate group equivalent. It is possible in these embodiments that one or both of A or E may comprise one or more phosphate group equivalents, whether it be in replacement of the phosphate group or in addition to the phosphate group.

In another embodiment of the lipid A mimics of the invention, neither A or E comprise a phosphate group attached directly thereto. In some embodiments, the phosphate group on both of A and E has been replaced with —H, —OH or a phosphate group equivalent. It is possible in these embodiments that A and E may comprise one or more phosphate group equivalents, whether it be in replacement of the phosphate group or in addition to the replacement.

In the lipid A mimics of the invention, the phosphate group or phosphate group equivalents may be attached directly or indirectly to the sugar residue or the aromatic group found at position A or E. If not attached directly to the sugar residue or aromatic group, they may be attached through a spacer or linker. Without limitation, the spacer or linker may be a substituted or unsubstituted, branched or linear, saturated or unsaturated, carbon chain optionally comprising one or more of oxygen, sulfur, or nitrogen. As an example, the phosphate group or phosphate group equivalent may be attached to the sugar residue through the following structure:

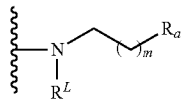

wherein:
$R_a$ is —H, —OH, a phosphate group or a phosphate group equivalent;
m is 0-6; and
$R^L$ is a lipid chain substituent as defined herein.

In a particular embodiment of the above formula, $R_a$ is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6.

In some embodiments, the lipid A mimics of the invention have 0, 1, 2, 3 or 4 phosphate or phosphate equivalent groups, and if they have more than one, they may be the same or different. Thus, they could have one phosphate group and one phosphate group equivalent. Alternatively, they could have one phosphate group and no phosphate group equivalent, or one phosphate group equivalent and no phosphate group. If there is more than one, the phosphate group or phosphate group equivalents may be attached to the same sugar residue or aromatic group at A or E (but not both) or may be attached to the sugar residue or aromatic group at both A and E.

To preserve structural similarity to natural lipid A, in some embodiments of the lipid A mimics of the invention where there remains a pyranose sugar residue at position A in formula A-L$_1$-D-L$_2$-E, the phosphate group or phosphate group equivalent may be attached to the C-4 carbon of the pyranose ring. In other embodiments where there remains a pyranose sugar residue at position E, the phosphate group or phosphate group equivalent may be attached to the C-1 carbon of the pyranose ring.

Lipid Chain Substituents of the Lipid A Mimics

Lipid diversity contributes to the most significant variations among natural lipid A structures. While they are all linked through ester and amide bonds to the hydroxy and amino groups of the sugar residues, variations include the number of lipids chains attached, the length of each lipid chain and the functional groups contained within the lipid chains.

As used herein, the term "lipid chain" refers to fatty acids and their derivatives, as well as substances related biosynthetically or functionally to these compounds. Generally, each lipid chain is a hydrophobic or amphipathic molecule that comprises one major carbon chain and optionally one or more minor carbon chains. Each carbon chain will be composed of carbon atoms linked sequentially by single, double or triple bonds. In some embodiments, no more than one bond of a particular carbon chain is a double or triple bond. In other embodiments, the carbon chain is fully saturated. Without limitation, the carbon chain may be a $C_{1-22}$ straight or branched chain alkyl, alkenyl, alkynyl, or dialkenyl, any of which may be optionally substituted with substituents selected from, for example, halogen, oxo, hydroxy, amino, and alkoxy. Carbon chains that are at least six carbons in length are considered "major" carbon chains, and other shorter carbon chains are considered "minor" carbon chains.

The carbon atoms of a carbon chain may be bonded to 3, 2, 1 or 0 hydrogens. In a major carbon chain, the —CH< and >C< carbons are usually branching points for the attachment (with or without a linker) of another carbon chain. They may also be substituted with a side group, such as amino or hydroxyl. The carbon atoms of any major carbon chain may include one or more carbonyl or thiocarbonyl carbons, i.e., —C(=O)— or —C(=S)—. If there is only one carbonyl or thiocarbonyl carbon, it is usually (but not necessarily) at the beginning of the chain, so the chain is an acyl chain (saturated or unsaturated). Thus, if the linker is —O—, the attachment to carbonyl forms an ester (—C(=O)—O—), whereas if it is —NH—, the attachment forms an amide (—C(=O)—NH—).

The expression "lipid chain substituent", as used herein, refers to each individual lipid substituent on the sugar residue or the aromatic group. Each lipid chain substituent may itself contain one or more lipid chains. Each lipid chain substituent of the lipid A mimics of the invention will comprise at least one major carbon chain. The lipid chain substituent may also comprise one or more minor carbon chains. The minor carbon chains may, for example, be a species of a linker that links the lipid chain substituent to the sugar residue or the aromatic group, or that links the major carbon chains to one another.

In some embodiments, the lipid chain substituent may comprise a single, unbranched lipid chain, i.e. a single major carbon chain. In other embodiments, the lipid chain substituent may comprise one, two, three or four lipid chains, such that the lipid chain substituent comprises one, two, three or four major carbon chains, respectively.

If the lipid chain substituent comprises more than one major carbon chain, the major chain beginning closest to the sugar residue or the aromatic group is considered the primary major chain of the group. Any chains attached to the primary major chain are considered secondary major chains. Any major chains attached to the secondary major chains are considered tertiary major chains, etc.

A secondary major chain may be attached to the distal end (relative to the sugar residue or aromatic group) of the primary major chain, in which case the lipid chain remains linear (absent other moieties). Or the secondary major chain may be attached to an interior carbon of the primary major chain, resulting in a branched lipid chain. A secondary major chain may be attached to a primary major chain by a simple —O—, —S— or —NH— linker, or it may be attached directly without a linker (i.e., C—C). It also may be attached by a complex linker. A tertiary major chain may be attached to a secondary major chain in the same manner as described above for the attachment of a secondary major chain to a primary major chain, and so on.

In an embodiment, a point of attachment of a higher order chain to a lower order chain (e.g. secondary to primary) is at the C-3 carbon of the lower order (e.g., primary) chain.

Like a primary major chain, a secondary or higher order major chain may comprise doubly or triply bonded carbon atoms, and/or carbonyl or thiocarbonyl carbons. The various carbon chains referred to above may be substituted with e.g. hydroxyl or amino groups. In an embodiment, the hydroxyl or amino group would be a substituent on the C-2 or C-3 carbon of the chain.

The lipid complement of the lipid A mimics of the invention comprises one or more of the lipid chain substituents as described herein. Each lipid chain substituent provides one or more major carbon chains. Collectively, the lipid chain substituents on the lipid A mimics provide one, two, three, four, five, six, seven, eight or more major carbon chains, with particular embodiments providing three to six major carbon chains. Each lipid chain substituent independently may provide one, two, three, four or more major carbon chains. In some embodiments, these major carbon chains are each 10-22 carbons in length, more particularly 12-16 carbons in length, and even more particularly 14 carbons in length.

In *E. coli* lipid A, the lipid groups provide 82 carbon atoms, and in *S. minnesota* lipid A, 98 carbons (7 acyl chains), while in *R. capsulatus* lipid A, which is an endotoxin antagonist, they provide 60 carbon atoms. There are monosaccharide analog lipid A agonists whose lipid groups provide 42 carbon atoms.

Hence, the major carbon chains of the lipid chain substituents collectively may provide at least 20, at least 30, at least 40, at least 50, at least 60, at least 70, or at least 80 carbon atoms. In corresponding embodiments, the lipid chain substituents collectively may provide not more than 120, not more than 110, not more than 100 or not more than 90 carbon atoms.

In some embodiments, each lipid chain substituent is connected to the remainder of the lipid A mimic (e.g. the sugar residue, the aromatic group or linker $L_1$ and/or $L_2$) by a proximal linker selected from of —O—, —S—, and —NH—. In the case of connection to a sugar residue, the proximal linker is the oxygen of a sugar hydroxyl, the sulfur of a thio sugar, or the nitrogen of an amino sugar. In the case of connection to the aromatic group or any other structure of the lipid A mimic (e.g. linker $L_1$ or $L_2$), the proximal linker is a portion of that respective structure as described herein.

This proximal linker may be bonded directly to a major carbon chain, or to a distal linker in the lipid chain substituent. The distal linker may be divalent, trivalent, tetravalent, etc. Usually it will be at least trivalent, thus serving to connect the remainder of the lipid A mimic to at least two different major carbon chains of the lipid chain substituent. The distal linker consists of two or more elements independently selected from the group consisting of a $C_{1-5}$ alkyl, —O—, —S—, —C(=O)—, —C(=S)—, —NH—, and —N<, with the caveat that the atoms of the distal linker connected directly to the major carbon chains of the lipid chain substituent are not carbon atoms. A distal linker is more often included in embodiments where the lipid chain substituent is not being attached to a sugar residue, but this is not necessarily the case.

If the lipid A mimics of the invention include a sugar residue (i.e. both of A and E in formula A-$L_1$-D-$L_2$-E have not been replaced with an aromatic group), at least one of the following sites on the sugar carbon skeleton may be linked to a lipid chain substituent:

(A) the anomeric ring carbon (only if substituent E is the sugar residue);

(B) the ring carbon immediately adjacent to the ring heteroatom (usually oxygen);

(C) a ring carbon other than those of (A) or (B) above; and/or (D) a sugar carbon other than a ring carbon (only if substituent A is the sugar residue).

It will be understood that such linkage will usually be through a linker such as a proximal linker as defined herein, but a connection without a linker (i.e., a C-substituted amino acid) is not absolutely excluded.

If the sugar is a pyranose, like glucose, at least one of the following sites may be linked to a lipid chain substituent:

(1) the C-2 carbon of the sugar ring (i.e., a site at which natural lipid A is N-lipidated);

(2) the C-3 carbon of the sugar ring (i.e., a site at which natural lipid A is O-lipidated);

(3) the C-1 (anomeric) carbon of the sugar ring (only if substituent E is the sugar residue; in natural lipid A this carbon is phosphorylated);

(4) the C-6 non-ring carbon of the sugar (only if substituent A is the sugar residue; in the lipid A disaccharide based on natural lipid A, this bears —OH, but this is normally the site of attachment of the lipid A disaccharide to the remainder of the LPS molecule); and/or (5) the C-4 carbon of the sugar ring (in natural lipid A, this is phosphorylated in one of the sugar residues and bears a free hydroxyl in the other sugar residue).

If a sugar residue remains in the lipid A mimic, the lipid chain substituents are in some embodiments attached to the C-2 and C-3 carbons of the sugar ring. The —O— linker may be found at the C-3 and C-4 carbons, and the —NH— linker at the C-2 carbon. It should be appreciated that if the $NH_2$ group on these carbons is lipidated, the $NH_2$ becomes an NH linker. Likewise, if the —OH group is lipidated, the —OH becomes an —O— linker.

There is no particular preference with regard to the linker at the anomeric carbon or at the non-ring carbons of the sugar.

In an embodiment, at least one of the lipid chain substituents on the lipid A mimics of the invention comprises a strongly lipophilic group. The determination and identification of strongly lipophilic groups is described by Jiang et al. in U.S. Pat. No. 8,097,593. Generally, the lipophilicity of groups may be determined by measuring the partition coefficient of the molecule HZ (where Z is the side chain in question) between a nonpolar solvent (e.g. ethanol, dioxane, acetone, benzene, n-octanol) and water, at STP. The lipophilicity may be defined as the logarithm of this partition coefficient; it will be positive for molecules which prefer the nonpolar solvent.

The partition coefficient (P) is defined as the ratio of the equilibrium concentrations of a dissolved substance in a two-phase system consisting of largely immiscible solvents. One such system is n-octanol:water, where the relevant partition coefficient (Pow) is the ratio of the molar concentration of the solute in octanol saturated with water to its molar concentration in water saturated with octanol. This system is described in Jiang et al. (U.S. Pat. No. 8,097,593), as well as in Sangster, J., *Octanol-Water Partition Coefficients: Fundamentals and Physical Chemistry* (April 1997) (ISBN 0-471-9739).

To avoid the need for experimental determinations of log Pow, the value predicted by Meylan's method can be used, as described in Jiang et al. (U.S. Pat. No. 8,097,593). In Meylan's method, the predicted log Pow is obtained by adding weighted coefficients for each fragment (the raw coefficient multiplied by the number of copies of that fragment) to the constant 0.2290. The fragments considered include aliphatically attached —CH3 (0.5473), —CH2- (-0.4911), —CH (0.3614), —OH (−1.4086), —NH2 (−1.4148), —C(=O)N(−0.5236), —SH (−0.0001), —NH— (−1.4962), —N=C (−0.0010), —O— (−1.2566), —CHO (−0.9422), -tert C so 3+C attached (0.2676), C no H not tert (0.9723), —C(=O)O— (−0.9505), —C(=O)— (−1.5586), =CH or C<(0.3836), #C (0.1334), —C(=O)N(−0.5236), —O—CO—C—N—CO (−0.5), —SO—O (−9), —O—P (−0.0162); 0=P (−2.4239), phosphate attached —OH (0.475); aromatic C (0.2940), aromatic N (5 membered ring)

(−0.5262), and aromatically attached —OH (−0.4802). The Meylan algorithm can be implemented in the program Log Pow (KowWin™).

A group is expected to be a lipophilic group if its log Pow, as predicted by the Meylan algorithm, is greater than zero. As described in Jiang et al. (U.S. Pat. No. 8,097,593), and for the purpose of this disclosure, a strongly lipophilic group is defined as being a group, comprising at least five atoms other than hydrogen, for which the predicted log Pow is at least 3. In further embodiments, the log Pow predicted by the Meylan algorithm for the strongly lipophilic group is at least 4, at least 5, at least 6, at least 7, at least 8, at least 9 or at least 10. For the purpose of determining whether a lipid chain substituent comprises a strongly lipophilic group, the proximal linker is disregarded, but the distal linker (if present) is considered part of the group.

In some embodiments of the lipid A mimics of the invention, any number of the lipid chain substituents may comprise a strongly lipophilic group. In an embodiment, all of the lipid chain substituents on the lipid A mimics will comprise a strongly lipophilic group. The collective sum of the predicted log Pows for the strongly lipophilic groups on the lipid A mimics may be at least 3, at least 6, at least 9, at least 12, at least 15, at least 20, at least 25, at least 30, at least 40, or at least 50. Typically, without limitation, it is not more than 60, not more than 50, not more than 40 or not more than 30.

As noted previously, the strongly lipophilic group comprises at least five atoms other than hydrogen. The strongly lipophilic group(s) may, for example, be composed of the major and minor carbon chains as defined above, including any substitutions that have been described. In some embodiments, the strongly lipophilic group comprises at least 6, at least 8, at least 9, at least 11 atoms other than hydrogen, in more particular embodiments at least 13 such atoms, and in even more particular embodiments at least 21 such atoms. Generally, the strongly lipophilic group will comprise not more than 100 atoms other than hydrogen, not more than 80 such atoms, not more than 60 such atoms, or not more than 40 such atoms.

The strongly lipophilic group typically has an elemental composition limited to the elements carbon, silicon, hydrogen, oxygen, nitrogen, sulfur, and phosphorous. Also, in some embodiments, the majority of the bonds within the group which do not involve hydrogen are carbon-carbon bonds, since the presence of oxygen, nitrogen, sulfur and phosphorous tends to reduce lipophilicity. Thus, in particular embodiments of the strongly lipophilic group, more than 50%, more than 60% or more than 75% of the non-hydrogen bonds are carbon-carbon bonds. For the same reason, typically no more than one double or triple bond between carbon atoms is present in the strongly lipophilic group, and in some embodiments there are no double or triple bonds between carbon atoms (e.g. the carbon chain is fully saturated).

Fatty acid groups of the form —O—C(═O)—$X^F$, where $X^F$ is primarily alkyl but may include alkenyl, alkynyl, or ether linkages, may be of particular interest as lipid chain substituents on the lipid A mimics of the invention. Generally, the fatty acids are composed of a chain of hydrocarbon groups containing from 4 to 22 carbon atoms and characterized by a terminal carboxyl radical. They may be designated by "the number of carbon atoms: number of double bonds", and optionally the locations of cis/trans isomerism. Thus, suitable fatty acids include, for example and without limitation, those with designations 4:0, 6:0, 8:0, 10:0, 12:0, 14:0, 16:0, 16:1 (9c), 18:0, 18:1 (9c), 18:2 (9c, 12c), 18:3 (9c, 12c, 15c), 18:4 (6c, 9c, 12c, 15c), 18:3 (9c, 11t, 13t), 18:1 (9c) 12-OH, 20:1 (9c), 20:1 (11c), 20:4 (8c, 11c, 14c, 17c), 20:5 (5c, 8c, 11c, 14c, 17c), 22:0, 22:1 (11c), 22:1 (13c), 22:5 (7c, 10c, 13c, 16c, 19c) and 22:6 (4c, 7c, 10c, 13c, 16c, 19c), all of which are found in naturally occurring glycosides.

The lipid structures which occur in natural lipid A from various species include 10:0, 12:0, 14:0, 16:0, 18:0, 20:0 fatty acids. Secondary acyl groups are usually 3-O-attached. Hydroxylation is usually 3-OH or 2-OH. A number of lipid A molecules (e.g., *Rhodobacter capsulatus* and *Rhodobacter sphaeroides*) include 12:1 or 14:1 secondary acyl groups. See Alexander et al., Trends in Glycoscience and Glycotechnology, 14: 69-86, 2002.

For the lipid chain substituents on the lipid A mimics of the invention, the following structures are of particular interest:

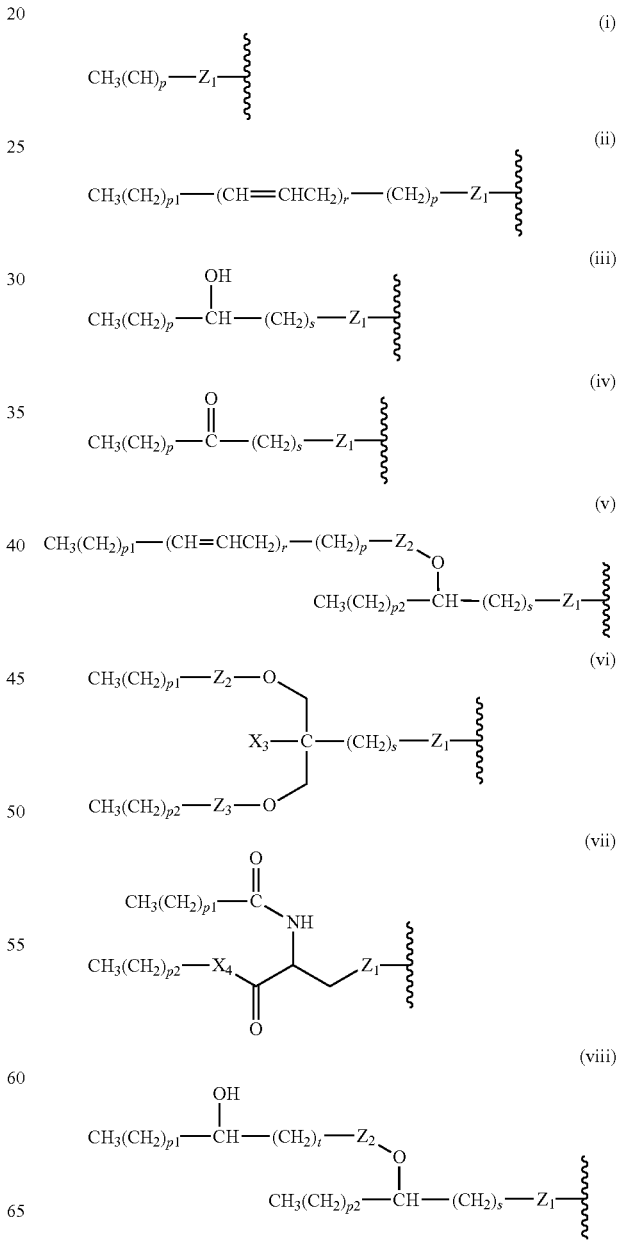

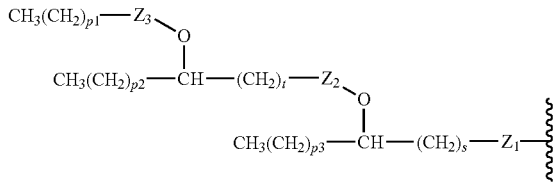 (ix)

wherein:
$Z_1$, $Z_2$ and $Z_3$ are independently —C(=O)— or —OH$_2$—;
$X_3$ is —H or —(CH$_2$)$_{p3}$CH$_3$;
$X_4$ is —NH—, —O— or —CH$_2$—;
p, p1, p2 and p3 are independently 0-30; and
r, s and t are independently 0-6.

More particularly, the structures above with the following definitions are of interest:

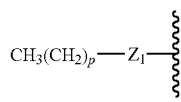 (i)

where $Z_1$ is —C(=O)— or —CH$_2$—, and p is 2-30;

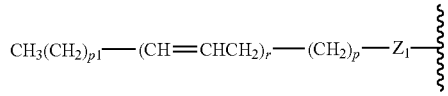 (ii)

where $Z_1$ is —C(=O)— or —CH$_2$—, r is 0-6, and p and p1 are independently 0-30, whereby p+p1+3r is 2-30;

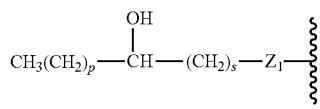 (iii)

where $Z_1$ is —C(=O)— or —CH$_2$—, s is 0-6, and p is 0-30, whereby s+p+1 is 2-30;

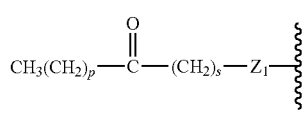 (iv)

where $Z_1$ is —C(=O)— or —CH$_2$—, s is 0-6, and p is 0-30, whereby s+p+1 is 2-30;

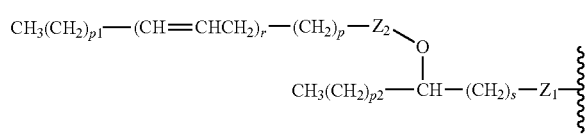 (v)

where $Z_1$ and $Z_2$ are independently —C(=O)— or —CH$_2$—, p, p1 and p2 are independently 0-30, and s and r are independently 0-6, whereby p+p1+3r is 3-30 and s+p2+1 is 2-30;

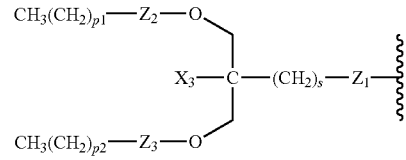 (vi)

where $Z_1$, $Z_2$ and $Z_3$ are independently —C(=O)— or —CH$_2$—, $X_3$ is —H, p1 and p2 are independently 2-30, and s is 0;

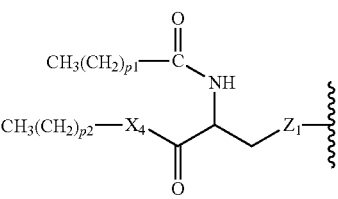 (vii)

where $Z_1$ is —C(=O)—, $X_4$—NH— or —O—, and p1 and p2 are independently 2-30;

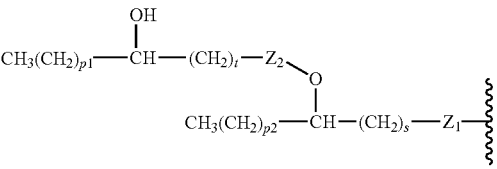 (viii)

where $Z_1$ and $Z_2$ are independently —C(=O)— or —CH$_2$—, p1 and p2 are independently 0-30, and s and t are independently 0-6, whereby p+t+1 is 2-30 and p2+s+1 is 2-30;

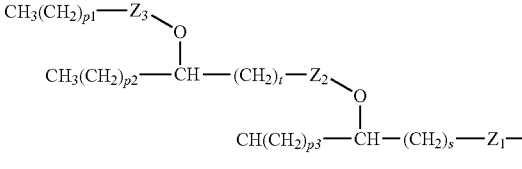 (ix)

where $Z_1$, $Z_2$ and $Z_3$ are independently —C(=O)— or —CH$_2$—, p1, p2 and p3 are independently 0-30, and s and t are independently 0-6, whereby p2+t+1 is 2-30 and p2+t+1 is 2-30.

Other lipid chain substituents encompassed are the lipid substituents described by Asai et al. in U.S. Pat. No. 6,235,724 and those described by Jiang et al. in U.S. Pat. No. 8,097,593. It will be understood that these lipid chain substituents should still qualify as strongly lipophilic groups.

For example, and without limitation, the lipid A mimics of the invention may include one or more lipid chain substituents selected independently from:

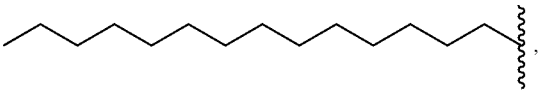

-continued

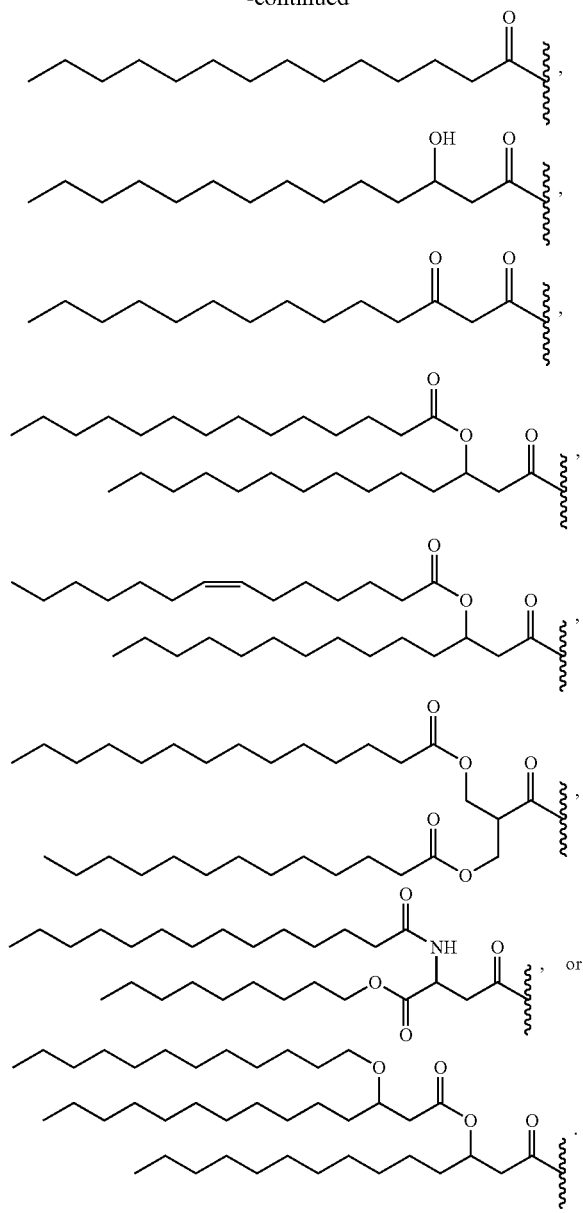

It is noted that all of the structures immediately above qualify as strongly lipophilic groups.

In an embodiment, the lipid A mimics of the invention will include one, two, three, four, five, six, seven or eight lipid chain substituents, each of which may be independently selected from, for example, the specific structures described above. In an embodiment, the lipid A mimics will include two, three, four or five lipid chain substituents, and in further embodiments three or four. Each of the lipid chain substituents may be the same or different than other lipid chain substituents on the lipid A mimic.

To preserve structural similarity to natural lipid A, some embodiments of the lipid A mimics of the invention may comprise at least one lipid chain substituent which is identical to a lipid chain substituent occurring in a natural lipid A structure. In a further sub-embodiment, all of the lipid chain substituents of the lipid A mimics are identical to those that occur in natural lipid A structures, but it is not necessary that they all occur in the same natural lipid A molecule.

In other embodiments, the lipid A mimics of the invention may comprise at least one lipid chain substituent which is not found in any natural lipid A structure. The difference may be, without limitation, a difference in the length of the major carbon chain(s), the degree of branching of the major carbon chain(s), the presence or location of unsaturated linkages in the major carbon chain(s), or the presence or location of —C(=O)—O— (ester), —O— (ether) or —NH-(amino) linkages. Examples of such lipid chain substituents may include, for example, any of the synthetic lipid acid structures disclosed by Jiang et al. in U.S. Pat. No. 7,491,707.

In the major form of natural *E. coli* lipid A, the disaccharide backbone is composed of two glucosamines (FIG. 1). The lipid component takes the form of six carbon chains, linked to the carbon atoms at the C-2 and C-3 positions of the sugar ring. One of the sugar residues has a branched lipid that is O-linked to the carbon atom at the C-3 position of the sugar ring, and a similar branched lipid that is N-linked to the carbon atom at the C-2 position of the sugar ring. This lipid chain substituent has the following structure:

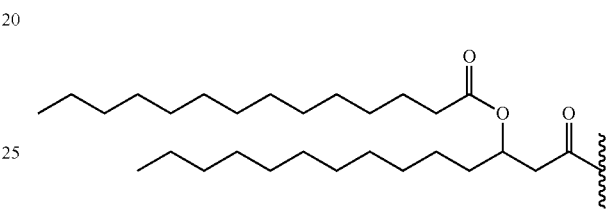

As can be seen, the primary chain (the one linked to the sugar ring carbon) is an acyl chain. A secondary acyl chain is O-linked to the C-3 carbon of the primary acyl chain (the carbonyl carbon being C-1). Thus, a total of four major carbon chains are linked directly or indirectly to this first sugar residue in the major form of natural *E. coli* lipid A.

On the second sugar residue in the major form of natural *E. coli* lipid A, an unbranched but hydroxylated acyl chain is O-linked to the carbon atom at the C-3 position of the sugar ring and another such acyl chain is N-linked to the carbon atom at the C-2 position of the sugar ring. This lipid chain substituent has the following structure:

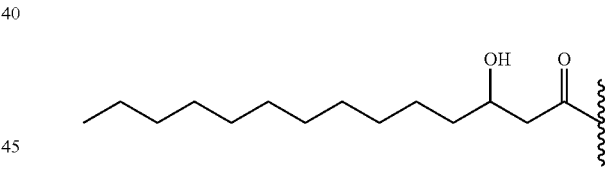

Thus, a total of two carbon major chains are linked this second sugar residue in the major form of natural *E. coli* lipid A. Since there are four acyl chains on one sugar, and two on the other, natural *E. coli* lipid A is said to have an asymmetric hexaacyl lipid complement, and, more specifically, a 4/2 distribution.

In an embodiment, the lipid chain substituents on the lipid A mimics of the invention may also provide an asymmetric hexaacyl lipid complement. Additionally or alternatively, the lipid A mimics of the invention comprise one or more lipid chain substituents identical to those in the major form of natural *E. coli* lipid A, as depicted above. The arrangement of the lipid chain substituents on the lipid A mimics may be the same or different than that of natural *E. coli* lipid A.

Spacers, Linkers and Connectivity of the Lipid A Mimics

The lipid A mimics may include any number of spacers or linkers. Some of the spacers or linkers that may be present in the lipid A mimics have already been mentioned. These include, for example, the proximal and distal linkers that may be present to connect the lipid chain substituents to the sugar residue or aromatic group; or the spacer or linker that may be used in substituent A or E of formula A-L$_1$-D-L$_2$-E to connect the phosphate or phosphate group equivalent to the sugar residue or aromatic group.

Other specific spacers or linkers of the lipid A mimics are the substituents L$_1$ and L$_2$ in formula A-L$_1$-D-L$_2$-E. These spacers may be present or absent. If present, they may without limitation be any substituted or unsubstituted, branched or linear, saturated or unsaturated, carbon chain optionally comprising one or more of oxygen, sulfur, or nitrogen. In some embodiments, a functional aspect of substituents L$_1$ and L$_2$ may be to provide distance between the substituent groups present at A and E (e.g. spacer function). In some embodiments, another functional aspect of L$_1$ and L$_2$ may be to provide a site of connection for a lipid chain substituent (e.g. linker function). The spacer or linker that may be used to connect the phosphate or phosphate group equivalents to the sugar residue or aromatic group likewise may provide one or both these functional aspects.

As an example, and without limitation, L$_1$ may have the following structure of II:

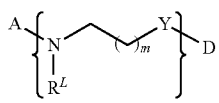

wherein A and D are those in A-L$_1$-D-L$_2$-E, m is 0-6, Y is —(CO)$_f$—, wherein f is 0 or 1, and R$^L$ is a lipid chain substituent.

As an example, and without limitation, L$_2$ may have the following structure of I:

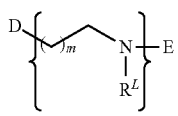

wherein D and E are those in A-L$_1$-D-L$_2$-E, m is 0-6 and R$^L$ is a lipid chain substituent.

The above exemplary structures for L$_1$ and L$_2$ provide the described functional aspect of providing a site of connection for a lipid chain substituent. Many other structures can also provide this functional characteristic and are encompassed herein. The structure of L$_1$ and/or L$_2$ may also provide more than one site of attachment for a lipid chain substituent, and may comprise one, two, three or four lipid chain substituents. In a particular embodiment, L$_1$ and L$_2$ individually provide one or two sites of attachment for a lipid chain substituent, more particularly one.

In an embodiment of the lipid A mimics, at least one of A, L$_1$, L$_2$, or E comprises one or more lipid chain substituents.

In another embodiment of the lipid A mimics, at least one of A or L$_1$ comprises one or more lipid chain substituents.

In another embodiment of the lipid A mimics, at least one of L$_2$ or E comprises one or more lipid chain substituents.

To preserve structural similarity of natural lipid A, in an embodiment of the lipid A mimics, at least one of A or L$_1$ and at least one of L$_2$ or E comprises one or more lipid chain substituents.

From the above, it will be understood that in particular embodiments of the lipid A mimics, L$_1$ is absent if: (i) substituent A is a sugar residue having one or more lipid chain substituents or (ii) substituent A is a sugar residue or aromatic group and there is a spacer or linker present that connects the phosphate or phosphate group equivalent to the sugar residue or aromatic group, this spacer or linker having at least one lipid chain substituent. Additionally or alternatively, in particular embodiments of the lipid A mimics, L$_2$ is absent if: (i) substituent E is a sugar residue having one or more lipid chain substituents or (ii) substituent E is a sugar residue or aromatic group and there is a spacer or linker present that connects the phosphate or phosphate group equivalent to the sugar residue or aromatic group, this spacer or linker having at least one lipid chain substituent.

Thus, if substituent A does not comprise a lipid chain substituent, then L$_1$ is typically present and comprises a lipid chain substituent. Likewise, in addition or in the alternative, if substituent E does not comprise a lipid chain substituent, then L$_2$ is typically present and comprises a lipid chain substituent.

The substituent D in formula A-L$_1$-D-L$_2$-E may also be considered a linker or a spacer. This position corresponds to the position of the O-glycosidic bond in natural lipid A. There exist other types of glycosidic bonds, including S- and N-glycosidic bonds. Thus, in the lipid A mimics of the invention, substituent D may be —O—, —S— or —NH. In a particular embodiment, substituent D is —O— in order to preserve structural similarity to natural lipid A. It is possible that other divalent groups may also be used as substituent D. For example, —S(O)—, —S(O)$_2$—, —OP(O)(OH)O— or —C(O)— can be used for linking two molecular fragments. In such instances, e.g. where D is —C(O)—, it will be appreciated that the definitions of substituents immediately adjacent to D may have to be adapted accordingly (e.g. the definition of Y).

Exemplary Groups of Lipid A Mimics

In one exemplary embodiment, the lipid A mimics of the invention may be a compound having the following structure:

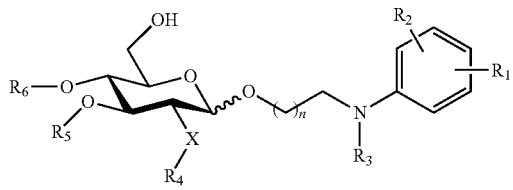

wherein:

the glycosidic linkage is α or β;

X is O or NH;

m is 0-6;

R$_1$ is placed in ortho-, meta-, or para-position to the N-substituent on the benzene ring and is —H, —OH, —OP(O)(OH)$_2$, —COOH, —SO$_3$H, —(O)$_k$(CH$_2$)$_n$COOH or —(O)$_k$(CH$_2$)$_q$OP(O)(OH)$_2$; wherein k is 0 or 1, n is 0-4, and q is 2-6;

R$_2$ is placed at any remaining position of the benzene ring and is —H, —OH, —Cl, —Br, —F, —COOH, —CN, —SO$_3$H, —OCH$_3$, —NO$_2$, or a C1-6 alkyl optionally substituted or unsubstituted;

R$_3$, R$_4$, and R$_5$ are each independently a lipid chain substituent; and

R$_6$ is —H, —P(O)(OH)$_2$, or —CH$_2$COOH, or a pharmaceutically acceptable salt thereof.

In a more particular embodiment of a lipid A mimic of the structure immediately above, X is NH; m is 1; R$_1$ is placed in ortho-position to the N-substituent on the benzene ring and is —OH or —OP(O)(OH)$_2$; R$_2$ is —H; R$_3$, R$_4$ and R$_5$ are each independently:

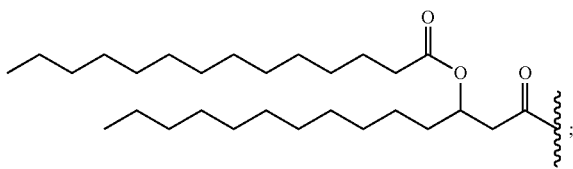 [SMILES: *C(=O)CC(CCCCCCCCCCC)OC(=O)CCCCCCCCCCCCC]

and $R_6$ is —P(O)(OH)$_2$.

Figure 2:
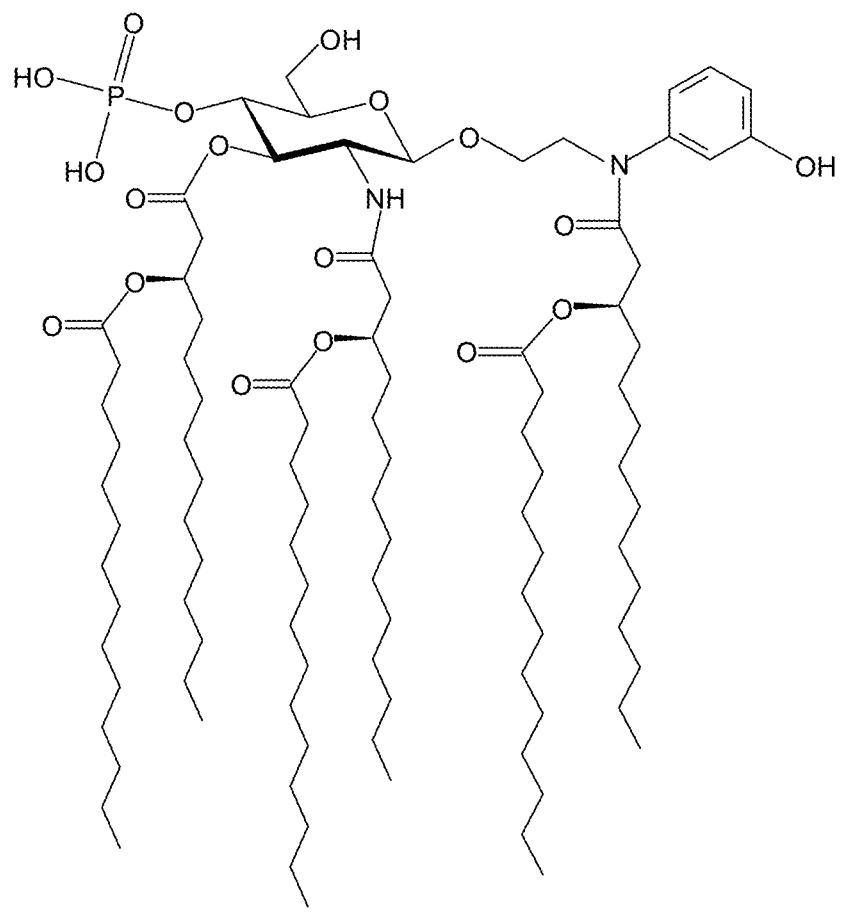
FIG. 2 illustrates the structure of an exemplary lipid A mimic of the present invention (JL-265).
Figure 3:
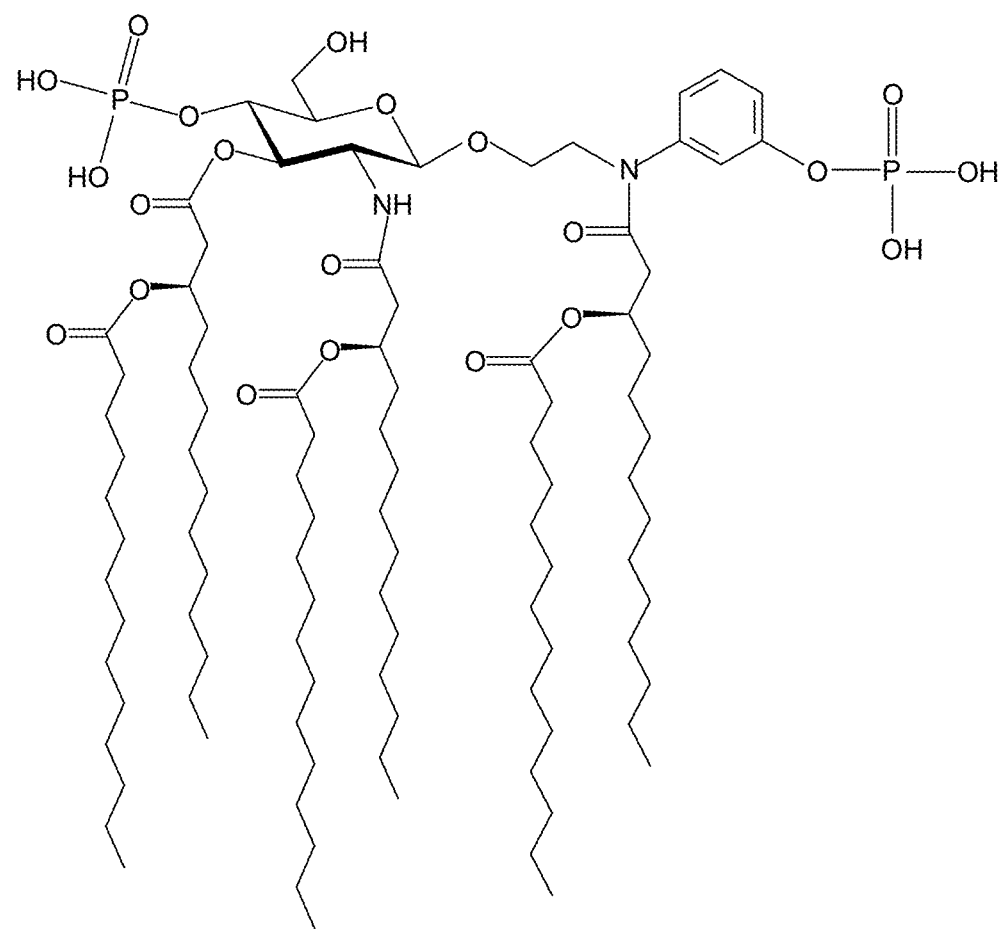
FIG. 3 illustrates the structure of an exemplary lipid A mimic of the present invention (JL-266).

Thus, in specific embodiments, the lipid A mimic of the invention is represented by the structure of JL-265 (FIG. 2) or JL-266 (FIG. 3), reproduced below:

JL-265
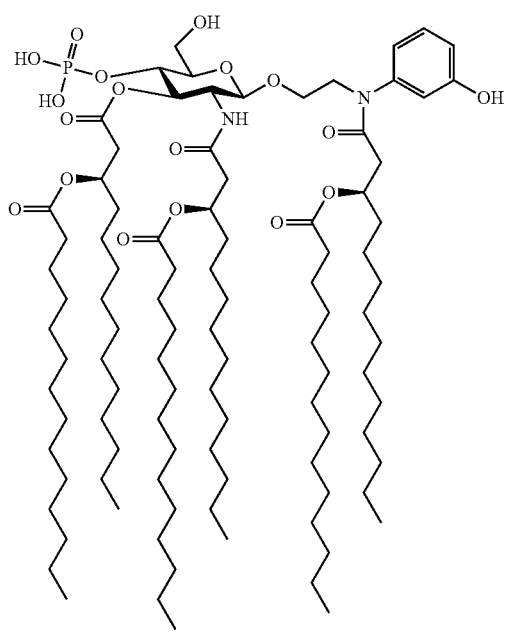

JL-266
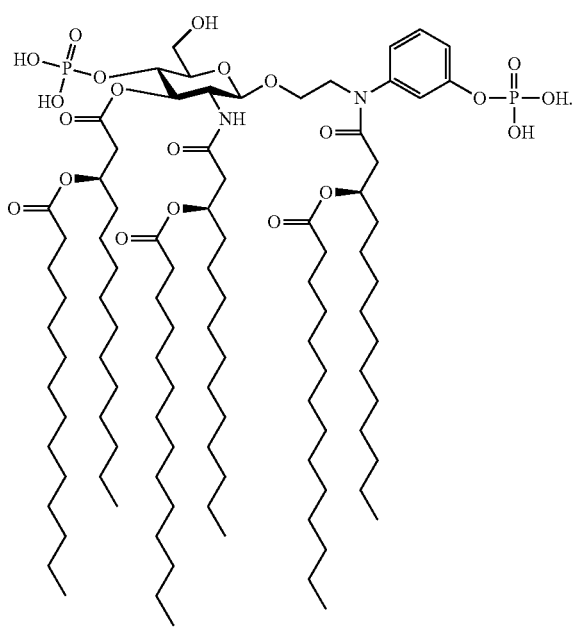

In another exemplary embodiment, the lipid A mimics of the invention may be a compound having the following structure:

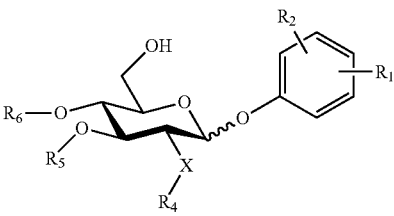

wherein:
the glycosidic linkage is α or β;
X is O or NH;
$R_1$ is placed in ortho-, meta-, or para-position to the N-substituent on the benzene ring and is:

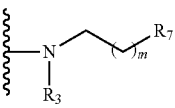

$R_7$ is —H, —OH, —OP(O)(OH)$_2$, —COOH, —SO$_3$H, —(O)$_k$(CH$_2$)$_n$COOH, or —(O)$_k$(CH$_2$)$_q$OP(O)(OH)$_2$; wherein k is 0 or 1, n is 0-4, and q is 2-6;
m is 0-6;
$R_2$ is placed at any remaining position of the benzene ring and is —H, —OH, —Cl, —Br, —F, —COOH, —CN, —SO$_3$H, —OCH$_3$, —NO$_2$, or a C1-6 alkyl optionally substituted or unsubstituted;
$R_3$, $R_4$, and $R_5$ are each independently a lipid chain substituent; and
$R_6$ is —H, —P(O)(OH)$_2$, or —CH$_2$COOH,
or a pharmaceutically acceptable salt thereof.

In another exemplary embodiment, the lipid A mimics of the invention may be a compound having the following structure:

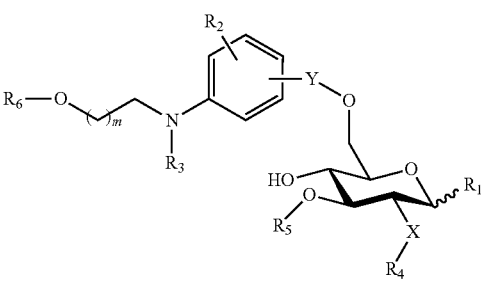

wherein:
the glycosidic linkage is α or β;
X is O or NH;
m is 0-6;
Y is placed in ortho-, meta-, or para-position to the N-substituent on the benzene ring and is —(O)$_g$(CH$_2$)$_h$(CO)$_j$—, wherein g is 0 or 1, h is 0-6, and j is 0 or 1;
$R_2$ is placed at any remaining position of the benzene ring and is —H, —OH, —Cl, —Br, —F, —COOH, —CN, —SO$_3$H, —OCH$_3$, —NO$_2$, or a $C_{1-6}$ alkyl optionally substituted or unsubstituted;

$R_1$ is —H, —OH, —OP(O)(OH)$_2$, —COOH, —SO$_3$H, —(O)$_k$(CH$_2$)$_n$COOH, or —(O)$_k$(CH$_2$)$_q$OP(O)(OH)$_2$; wherein k is 0 or 1, n is 0-4, and q is 2-6;

$R_3$, $R_4$, and $R_5$ are each independently a lipid chain substituent; and $R_6$ is —H, —P(O)(OH)$_2$, or —CH$_2$COOH, or a pharmaceutically acceptable salt thereof.

In another exemplary embodiment, the lipid A mimics of the invention may be a compound having the following structure:

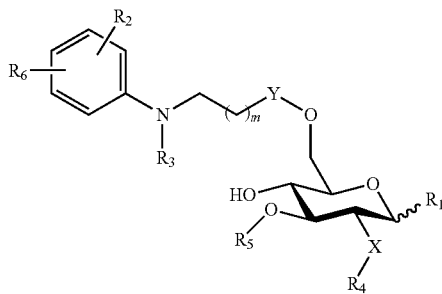

wherein:
the glycosidic linkage is α or β;
X is O or NH;

m is 0-6;

$R_6$ is placed in ortho-, meta-, or para-position to the N-substituent on the benzene ring and is —H, —OH, —OP(O)(OH)$_2$, —COOH, —SO$_3$H, —(O)$_k$(CH$_2$)$_n$COOH, or —(O)$_k$(CH$_2$)$_q$OP(O)(OH)$_2$; wherein k is 0 or 1, n is 0-4, and q is 2-6;

$R_2$ is placed at any remaining position of the benzene ring and is —H, —OH, —Cl, —Br, —F, —COOH, —CN, —SO$_3$H, —OCH$_3$, —NO$_2$, or a C$_{1-6}$ alkyl optionally substituted or unsubstituted;

Y is —(CO)$_f$—, wherein f is 0 or 1;

$R_1$ is —H, —OH, —OP(O)(OH)$_2$, —COOH, —SO$_3$H, —(O)$_k$(CH$_2$)$_n$COOH, or —(O)$_k$(CH$_2$)$_q$OP(O)(OH)$_2$; wherein k is 0 or 1, n is 0-4, and q is 2-6; and $R_3$, $R_4$, and $R_5$ are each independently a lipid chain substituent, or a pharmaceutically acceptable salt thereof.

Description of the Synthesis of Lipid A Mimics JL-265 (2) and JL-266 (3)

The synthesis of lipid A mimics JL-265 (2) and SL-266 (3) began with the formation of glycosyl acceptor 7 (Scheme 1; below). As such, the amine moiety in 3-aminophenol was condensed with 2-chloroethanol in the presence of aqueous sodium bicarbonate at 90° C. to yield the phenolic-based acyclic scaffold of 4 in 58% yield. Protection of the primary hydroxyl group in 4 via treatment with tert-butyldiphenylsilyl chloride (TBDPS-Cl) and imidazole in N,N-dimethylformamide (DMF) gave 5 in 84% yield. This therefore allowed for the selective acylation of the amine moiety in 5 via the mixed anhydride method in which dilipid acid 8 (Kiso et al., *Carbohydr. Res.*, 162: 247-256, 1987) was first condensed with isobutyl chloroformate (IBCF) via N-methylmorpholine (NMM) in CH$_2$Cl$_2$ at −20° C. to generate the anhydride, which was then allowed to couple to the amine group of 5, ultimately yielding 6 in an 80% overall yield. Finally, cleavage of the silyl ether protecting group in 6 via tetrabutyl ammonium fluoride treatment in a CH$_2$Cl$_2$ and acetic acid mixture gave desired glycosyl acceptor 7 in an 81% yield.

Scheme 1.

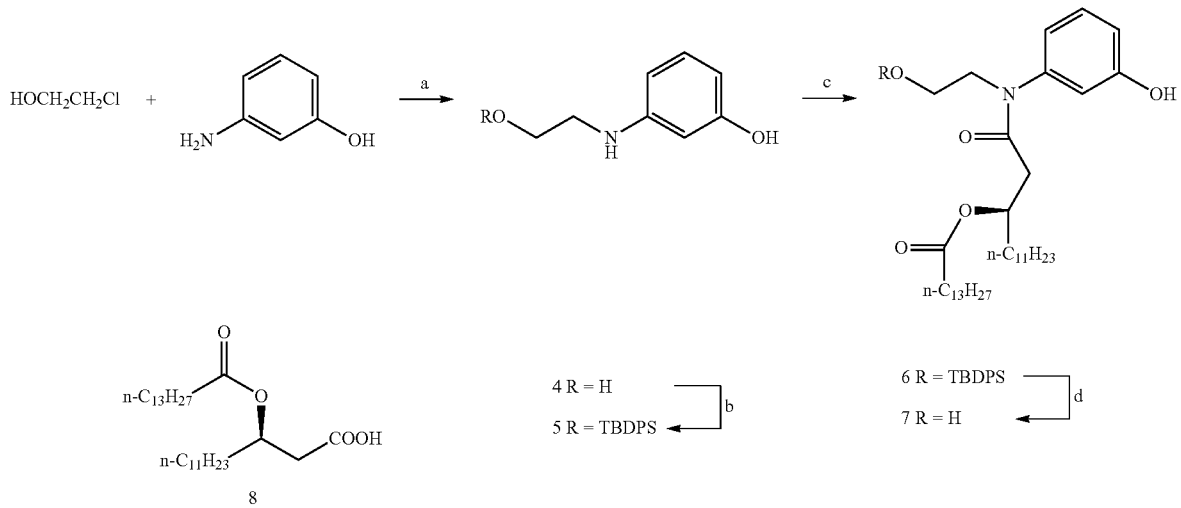

Reagents and conditions: (a) NaHCO$_3$, H$_2$O, 90° C., 58%; (b) TBDPS—Cl, imidazole, DMF, 84%; (c) (i) 8, IBCF, NMM, CH$_2$Cl$_2$, -20° C., (ii) then add 5, 80%; (d) Bu$_4$NF, CH$_2$Cl$_2$, HOAc, 81%.

The trimethylsilyl trifluoromethane sulfonate (TMSOTf) catalyzed glycosylation of glycosyl acceptor 7 with known imidate donor 9 (Jiang et al., *Tetrahedron*, 58: 8833-8842, 2002) yielded glycoside 10 in an 89% yield (Scheme 2; below). The desired β-glycosidic linkage in 10 was confirmed by $^1$H NMR spectral data (δ 4.59, d, J 8.5 Hz, H-1). Removal of the N-Troc protecting group in 10 via treatment with zinc powder in acetic acid, followed by the N, N'-diisopropylcarbodiimide (DIC) promoted coupling with dilipid acid 8 gave the hexaacylated derivative 11 in 68% overall yield. Lipid A mimic JL-265 (2) was obtained in an 88% yield by subjecting compound 11 to global deprotection via catalytic hydrogenation in tetrahydrofuran (THF). To obtain lipid A mimic JL-266 (3), compound 11 was first converted to diphosphate derivative 12 in a 93% overall yield via the two step reaction with first, dibenzyl N,N-diisopropyl phosphoramidite [(BnO)$_2$PN(iPr)$_2$] and 5-phenyltetrazole in CH$_2$Cl$_2$, followed by the oxidation of the phosphite intermediate by m-chloroperbenzoic acid (m-CPBA) at 0° C. Thus, a global deprotection of 12 via catalytic hydrogenation in THF afforded lipid A mimic JL-266 (3) in an 89% yield. The structure of lipid A mimics JL-265 (2) and JL-266 (3) have been confirmed by $^1$H NMR and high resolution MALDI-MS data.

nesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

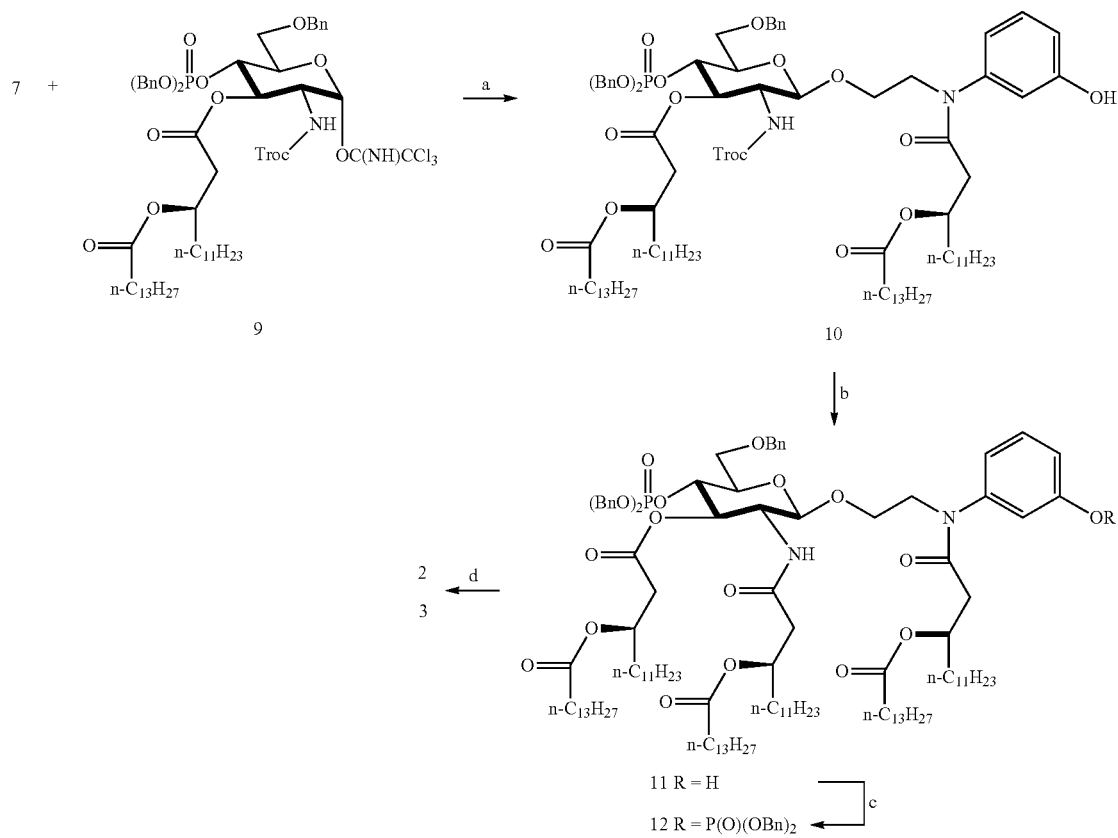

Scheme 2.

Reagents and conditions: (a) TMSOTF, CH$_2$Cl$_2$, 89%; (b) (i) Zn dust, HOAc; (ii) 8, DIC, CH$_2$Cl$_2$, 68%; (c) (i) (BnO)$_2$PN(iPr)$_2$, 5-Ph-Tetrazole, CH$_2$Cl$_2$, (ii) m-CPBA, 0° C., 93%; (d) H$_2$, Pd/C, THF, 88% for JL-266 (2) and 89% for JL-266 (3).

Pharmaceutically Acceptable Salts

The lipid A mimics of the invention also include pharmaceutically acceptable salts of the disclosed compounds.

As used herein the term "pharmaceutically acceptable salt" refers to salts of the lipid A mimics that retain biological activity, and which are not biologically or otherwise undesirable. Many of the lipid A mimics disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and mag- Combinations Any of the lipid A mimics disclosed herein may be used in combination with each other, optionally together with one or more other pharmaceutical agents. When the lipid A mimic is used as an immunological agent, it may be used in combination with other immunological agents. As used herein, the term "immunological agent" refers to any agent (e.g. molecule or compound) that can have an effect on the immune response or the immune system of a subject, whether it be immunostimulatory or immunoinhibitory. Without limitation, immunological agents include antigens (including both immunogens and haptens), adjuvants, cytokines, or any other immunomodulatory molecule as described herein or as known in the art.

Any of the lipid A mimics of the invention may be used in combination with each other, with other lipid A mimics or analogues, with natural lipid A molecules, or with other pharmaceutical agents (e.g. adjuvants, carriers, diluents, excipients, etc). Notably, the pharmaceutical agents may be immunological agents.

A combination may be a covalent conjugate, a non-covalent conjugate, a simple mixture, use such that all of the elements are present in the subject at the same or overlapping times, or use such that all of the elements of the combination are simultaneously active in the subject to which they are administered. Simultaneous activity may, but need not, be achieved by simultaneous administration. Compounds may be simultaneously active even if they are not simultaneously administered, e.g. where compound X with a long half-life is administered prior to compound Y with a short half-life, but X is still present in the body at an effective level when Y is administered. Thus, simultaneously active includes consecutive administration of the members of the combination.

Pharmaceutical Compositions

The lipid A mimics of the invention may be formulated in a pharmaceutical composition, optionally together with a pharmaceutically acceptable carrier.

In some embodiments the pharmaceutical composition contains, as an active ingredient, a lipid A mimic as disclosed herein in a therapeutically effective amount. As used in this embodiment, a "therapeutically effective amount" refers to an amount of the lipid A mimic effective to treat, prevent or suppress a condition or symptom associated with an LPS/lipid A-mediated disease or disorder or LPS-mediated virus production, including treating, preventing or suppressing the disorder or virus production itself or suppressing an overactivation of a subject's immune system caused by the LPS/lipid A-mediated disorder. In these embodiments, the lipid A mimic typically is a LPS/lipid A antagonist. Optionally, the pharmaceutical composition includes a pharmaceutically acceptable carrier.

In other embodiments the pharmaceutical compositions comprise, as a first component, an active agent other than a lipid A mimic and, as a second component, at least one lipid A mimic of the invention. In this embodiment of the pharmaceutical composition, the lipid A mimic may be included as e.g. an adjuvant. The first component, i.e., the active agent, can include any therapeutic agent, or multiple therapeutic agents, without limitation, since the function of the lipid A mimic in this embodiment is often that of an auxiliary, immunostimulating compound. In an embodiment, the active agent is an antigen as described herein. Pharmaceutical compositions that include an antigen as the active agent are referred to herein as a vaccine composition, as described later herein. Optionally, the pharmaceutical composition (or vaccine composition) includes a pharmaceutically acceptable carrier.

As used herein, the term "pharmaceutically acceptable carrier" refers to a carrier that is 'acceptable' in the sense of being compatible with the other ingredients of a composition and not deleterious (e.g. toxic) to the recipient thereof. Typcially, the pharmaceutically acceptable carrier is a medium that does not interfere with the immunomodulatory activity of the active ingredient and/or the lipid A mimics.

Some examples of pharmaceutically acceptable carriers include, but are by no means limited to, e.g., water, phosphate buffered saline, glycerol, ethanol, Ringer's solution, dextrose solution, serum-containing solutions, Hank's solution, other aqueous physiologically balanced solutions, oil-in-water emulsions, oils, water-in-oil emulsions, esters, poly (ethylene-vinyl acetate), copolymers of lactic acid and glycolic acid, poly(lactic acid), gelatin, collagen matrices, polysaccharides, poly(D,L lactide), poly(malic acid), poly (caprolactone), celluloses, albumin, starch, casein, dextran, polyesters, mathacrylate, polyurethane, polyethylene, vinyl polymers, glycols, thyroglobulin, albumins such as human serum albumin, tetanus toxoid, polyamino acids such as poly L-lysine, poly L-glutamic acid, influenza, hepatitis B virus core protein, mixtures thereof and the like. See, for example, Remington: The Science and Practice of Pharmacy, 2000, Gennaro, A R ed., Eaton, Pa.: Mack Publishing Co.

In some embodiments, the carrier of the pharmaceutical or vaccine compositions herein is a carrier comprising a continuous phase of a hydrophobic substance, as described later herein.

The pharmaceutical compositions may additionally comprise further excipients, auxiliary agents or diluents which are known in the art, such as and without limitation, salts, buffering agents, wetting or emulsifying agents, and preservatives. See, e.g., Porter et al., eds., The Merck Manual, 19th edition, Merck and Co., Rahway, N.J., 2011. When used in pharmaceutical compositions, the salts should typically be pharmaceutically acceptable salts as described herein, but non-pharmaceutically acceptable salts may conveniently be used to prepare pharmaceutically acceptable salts thereof and are not excluded from the scope of the invention.

The pharmaceutical composition of the invention optionally further includes, in addition to the lipid A mimics disclosed herein, any adjuvant or mixture of adjuvants known to one skilled in the art that are capable of boosting or enhancing the immune response in a subject. Examples of other adjuvants are well known to those skilled in the art and include, without limitation, nonionic block polymers, aluminum hydroxide or aluminum phosphate adjuvant, and mixtures thereof. The pharmaceutical compositions may also include as additional adjuvants to the lipid A mimics disclosed herein, other lipid A mimics or analogues.

Additionally or alternatively, the pharmaceutical compositions may include immunomodulators, such as cytokines which favour or inhibit either a cell-mediated immune response or a humoral immune response, or inhibitory antibodies against such cytokines. Other examples of immunomodulators include any agent that interferes with DNA replication, such as for example those described in WO 2014/153636 (e.g. cyclophosphamide) or immune checkpoint pathway inhibitors (e.g. PD-1 pathway inhibitors). These and other compounds or agents that function as immunomodulators are known in the art and any one or more immunomodulators may be used in or with the compositions described herein. The immunomodulators may be a component of the compositions described herein or may be administered separately.

In some embodiments of the pharmaceutical composition, the components (e.g. lipid A mimics, antigens, etc) may be incorporated into a delivery vehicle. Such delivery vehicles may include, but are not limited to, liposomes, liposheres, polymers, and slow release devices such as microspheres or microcapsules, and combinations thereof.

In an embodiment, when these delivery vehicles are used (e.g. liposomes), the carrier is a carrier comprising a continuous phase of a hydrophobic substance, as described later herein.

The composition may comprise antigen-presenting cells, and in such cases the antigen may be pulsed onto the cells, prior to administration, for more effective presentation.

In some embodiments, the pharmaceutical compositions may further comprise at least one cancer chemotherapeutic compound, such as for example, and without limitation, one selected from the group consisting of an anti-metabolite, a bleomycin peptide antibiotic, a podophyllin alkaloid, a Vinca alkaloid, an alkylating agent (e.g. temozolomide), an antibiotic, cisplatin, or a nitrosourea. The pharmaceutical compositions may further comprise at least one viral chemotherapeutic compound, such as for example, and without limitation, one selected from gamma globulin, amantadine, guanidine, hydroxybenzimidazole, interferon-α, interferon-β, interferon-γ, thiosemicarbarzones, methisazone, rifampin, ribvirin, a pyrimidine analog, a purine analog, foscarnet, phosphonoacetic acid, acyclovir, dideoxynucleosides, or ganciclovir. See, e.g., Katzung, ed., Basic and Clinical Pharmacology, Fifth Edition, Appleton and Lange, Norwalk, Conn., (1992).

As mentioned above, particular embodiments of the pharmaceutical compositions are vaccine compositions. These will now be described in greater detail. It is to be understood that the embodiments and features described above for pharmaceutical compositions equally apply to the vaccine compositions of the invention, where feasible. Likewise, embodiments and features of vaccine compositions described herein may be applied to the pharmaceutical compositions generally, where feasible.

Vaccine Compositions

As used herein, the terms "vaccine" or "vaccine composition" may be used interchangeably.

Vaccine compositions of the invention, for use together with a lipid A mimic, may be of any form suitable for delivery of an antigen to a subject. Vaccine compositions according to the invention can be formulated according to known methods, such as by admixture of the lipid A mimic, one or more antigens and one or more pharmaceutically acceptable excipients or carriers, such as for example those acceptable for administration to humans. Examples of such excipients, carriers and methods of formulation may be found e.g. in Remington's Pharmaceutical Sciences (Maack Publishing Co, Easton, Pa.). To formulate a pharmaceutically acceptable vaccine composition suitable for effective administration, such compositions will typically contain a therapeutically effective amount of the antigen together with one or more lipid A mimics disclosed herein.

Vaccine compositions according to the invention may be administered to a subject in a therapeutically effective amount. As used herein, a "therapeutically effective amount" means an amount of vaccine or active ingredient (e.g., antigen) effective to treat, prevent, alleviate, or ameliorate a disease or disorder, or a condition or symptom associated with that disease or disorder; prolong the survival of the subject being treated; and/or stimulate, induce or enhance an immune response in a subject, such as a humoral immune response or a cell-mediated immune response. Determination of a therapeutically effective amount of the vaccine or active ingredient is well within the capability of those skilled in the art. The therapeutically effective amount may vary according to a variety of factors such as the subject's condition, weight, sex and age.

Once one or more appropriate antigens have been selected for inclusion in a vaccine composition together with a lipid A mimic of the present invention, the antigen may be delivered by various suitable means which are known in the art. Vaccine compositions may include for example, and without limitation, lipopeptides (e.g., Vitiello, A. et al., J. Clin. Invest. 95:341, 1995), peptide compositions encapsulated in poly(DL-lactide-co-glycolide) ("PLG") microspheres (see, e.g., Eldridge, et al., Molec. Immunol. 28:287-294, 1991: Alonso et al., Vaccine 12:299-306, 1994; Jones et al., Vaccine 13:675-681, 1995), peptide compositions contained in immune stimulating complexes (ISCOMS) (see, e.g., Takahashi et al., Nature 344:873-875, 1990; Hu et al., Clin Exp Immunol. 113:235-243, 1998), multiple antigen peptide systems (MAPs) (see e.g., Tam, J. P., Proc. Natl. Acad. Sci. U.S.A. 85:5409-5413, 1988; Tam, J. P., J. Immunol. Methods 196:17-32, 1996), peptides formulated as multivalent peptides; peptides for use in ballistic delivery systems, typically crystallized peptides, viral delivery vectors (Perkus, M. E. et al., In: Concepts in vaccine development, Kaufmann, S. H. E., ed., p. 379, 1996; Chakrabarti, S. et al., Nature 320:535, 1986; Hu, S. L. et al., Nature 320:537, 1986; Kieny, M.-P. et al., AIDS Bio/Technology 4:790, 1986; Top, F. H. et al., J. Infect. Dis. 124:148, 1971; Chanda, P. K. et al., Virology 175:535, 1990), particles of viral or synthetic origin (e.g., Kofler, N. et al., J. Immunol. Methods. 192:25, 1996; Eldridge, J. H. et al., Sem. Hematol. 30:16, 1993; Falo, L. D., Jr. et al., Nature Med. 7:649, 1995), adjuvants (Warren, H. S., Vogel, F. R., and Chedid, L. A. Annu. Rev. Immunol. 4:369, 1986; Gupta, R. K. et al., Vaccine 11:293, 1993), liposomes (Reddy, R. et al, J. Immunol. 148:1585, 1992; Rock, K. L., Immunol. Today 17:131, 1996), or, naked or particle absorbed cDNA (Ulmer, J. B. et al., Science 259:1745, 1993; Robinson, H. L., Hunt, L. A., and Webster, R. G., Vaccine 11:957, 1993; Shiver, J. W. et al., In: Concepts in vaccine development, Kaufmann, S. H. E., ed., p. 423, 1996; Cease, K. B., and Berzofsky, J. A., Annu. Rev. Immunol. 12:923, 1994 and Eldridge, J. H. et al., Sem. Hematol. 30:16, 1993).

Vaccine compositions of the invention also encompass nucleic acid mediated modalities. For example, DNA or RNA encoding one or more of the antigens as described herein may be administered to the subject. Such approaches are described, for example, in Wolff et al., Science 247:1465 (1990) as well as U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

In further embodiments of the vaccine compositions, the antigens may be expressed by viral or bacterial vectors. Examples of expression vectors include attenuated viral hosts, such as vaccinia or fowlpox. This approach involves the use of vaccinia virus, for example, as a vector to express nucleotide sequences that encode the antigens as described herein. Upon introduction into an acutely or chronically infected host or into a non-infected host, the recombinant vaccinia virus expresses the antigenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 351:456-460 (1991). A wide variety of other vectors useful for therapeutic administration or immunization of the antigen, e.g. adeno and adeno-associated virus vectors, retroviral vectors, *Salmonella typhi* vectors, detoxified anthrax toxin vectors, and the like, will be apparent to those skilled in the art and are encompassed by the vaccine compositions described herein.

Vaccines in accordance with the invention also encompass compositions containing one or more of the antigens, where the antigen can be present individually or as a construct containing multiple copies of the same or different antigen. For example, the antigen can be present as a single nucleic acid molecule (e.g. vector) encoding several of the same or different antigens. Or, in other embodiments, a homopolymer comprising multiple copies of the same antigen, or a heteropolymer of various different antigens, may be used. Such polymers may have the advantage of providing an increased immunological reaction as they comprise multiple copies of the antigens, such that the resultant effect may be an enhanced ability to induce an immune response with one or more antigenic determinants of a particular antigen. The composition can comprise a naturally occurring region of one or more antigens or can comprise prepared antigens, e.g., recombinantly or by chemical synthesis.

A vaccine of the invention can also include antigen-presenting cells (APC), such as dendritic cells (DC), as a vehicle to present the one or more antigens to the immune system. Such vaccine compositions can be created in vitro, following dendritic cell mobilization and harvesting, whereby loading of dendritic cells occurs in vitro. For example, dendritic cells are transfected with DNA or RNA encoding the one of more antigens, or are pulsed with peptide antigens. The dendritic cell can then be administered to a subject to elicit an immune response in vivo.

A vaccine according to the invention may be administered by any suitable means, such as e.g. injection (e.g. intramuscular, intradermal, subcutaneous, intravenous or intraperitoneal), aerosol, oral, nasal, topical, intravaginal, transdermal, transmucosal, or any other suitable routes. The vaccine may be formulated for systemic or localized distribution in the body of the subject. Systemic formulations include those designed for administration by injection, as well as those designed for transdermal, transmucosal or oral administration.

In some embodiments, such as for administration by injection, the vaccines may be formulated in a carrier comprising a continuous phase of a hydrophobic substance as described herein, such as a water-in-oil emulsion or an oil-based carrier. Additionally or alternatively, the vaccine compositions may be liposome formulations. In more particular embodiments, liposomes may be used together with the hydrophobic carrier. The vaccines may also be formulated as aqueous solutions such as in Hank's solution, Ringer's solution or physiological saline buffer.

As will be apparent from the above, vaccine compositions of the invention are meant to encompass any composition or antigen/immunogen delivery means (e.g. viral vectors) which are useful in the treatment of a disease or disorder associated with the antigen, including compositions capable of stimulating an immune response in a subject upon administration, such as a specific cell-mediated immune response or a humoral immune response.

To obtain vaccine compositions of the invention, it may be suitable to combine the lipid A mimic and antigen, with various materials such as adjuvants, excipients, surfactants, immunostimulatory components and/or carriers. Adjuvants may be included in the vaccine composition to enhance the specific immune response. Different carriers may be used depending on the desired route of administration or the desired distribution in the subject, e.g. systemic or localized.

In a particular embodiment, the vaccine composition may comprise at least one antigen, at least one lipid A mimic of the invention, liposomes and a carrier comprising a continuous phase of a hydrophobic substance. In a further embodiment, the composition may additionally comprise a T-helper epitope. The antigen may be or comprise a B cell epitope. The antigen may be or comprise a CTL epitope and it may be fused to a T-helper epitope.

Thus, in an embodiment, the vaccine composition comprises one or more antigens; a lipid A mimic; a T-helper epitope; liposomes; and a carrier comprising a continuous phase of a hydrophobic substance.

In some embodiments, the vaccine composition is one comprising at least one lipid A mimic and at least one antigen, together with Immunovaccine, Inc's liposome-based and/or amphipathic compound-based vaccine adjuvanting platform, including, but not limited to, the VacciMax® and DepoVax™ platform technologies (see e.g. U.S. Pat. Nos. 6,793,923 and 7,824,686; WO 2002/038175; WO 2007/041832; WO 2009/039628; WO 2009/043165 and WO 2009/146523). The DepoVax™ platform is a vaccine delivery formulation that provides controlled and prolonged exposure of antigens plus adjuvant to the immune system. The platform is capable of providing a strong, specific and sustained immune response and is capable of single-dose effectiveness.

The vaccine may optionally further comprise additional components such as, for example, emulsifiers. A more detailed disclosure of exemplary embodiments of the vaccine, and the components thereof, are described as follows.

Antigens

In some embodiments, the pharmaceutical or vaccine compositions of the invention, which include a lipid A mimic as disclosed herein, may also comprise one or more antigens. Typically, but not always, when a composition disclosed herein includes an antigen, it will be a vaccine composition.

As used herein, the term "antigen" refers to any substance or molecule that can bind specifically to components of the immune system. In some embodiments, suitable antigens of the compositions herein are those that are capable of inducing or potentiating an immune response in a subject. An antigen that is capable of inducing an immune response is said to be immunogenic, and may also be called an immunogen. Thus, as used herein, the term "antigen" includes immunogens and the terms may be used interchangeably unless specifically stated otherwise. The term antigen, as used herein, also includes haptens. As is understood in the art, a hapten is a small molecule that is antigenic (e.g. capable of being bound by components of the immune system), but is not immunogenic unless it is attached to a carrier molecule of some sort which supplies the immunogenicity.

Antigens that may be useful in the compositions of the invention include, for example and without limitation, a polypeptide, carbohydrate, a microorganism or a part thereof, such as a live, attenuated, inactivated or killed bacterium, virus or protozoan, or part thereof. The antigen may be, for example, a pathogenic biological agent, a toxin, an allergen, a peptide, a suitable native, non-native, recombinant or denatured protein or polypeptide, or a fragment thereof, or an epitope that is capable of inducing or potentiating an immune response in a subject. In some embodiments, the antigen may be one that is derived from an animal (an animal antigen), such as for example a human (a human antigen), or an antigen that is substantially related thereto.

As used herein, the term "derived from" encompasses, without limitation: an antigen that is isolated or obtained directly from an originating source (e.g. a subject); a synthetic or recombinantly generated antigen that is identical or substantially related to an antigen from an originating source; or an antigen which is made from an antigen of an originating source or a fragment thereof. The term "substantially related", as used herein, means that the antigen may have been modified by chemical, physical or other means (e.g. sequence modification), but that the resultant product remains capable of generating an immune response to the original antigen or to the disease or disorder associated with the original antigen.

As used herein, the term "antigen" also includes a polynucleotide that encodes a polypeptide that functions as an antigen. Nucleic acid-based vaccination strategies are known, wherein a vaccine composition that contains a polynucleotide is administered to a subject. The antigenic polypeptide encoded by the polynucleotide is expressed in the subject, such that the antigenic polypeptide is ultimately present in the subject, just as if the vaccine composition itself had contained the polypeptide. For the purposes of the present disclosure, the term "antigen", where the context dictates, encompasses such polynucleotides that encode the polypeptide which functions as the antigen.

In some embodiments, the antigen is a molecule comprising at least one B cell epitope or CTL epitope, as defined below, and which, when suitably administered to a subject, induces or potentiates a humoral and/or cell-mediated immune response which is protective against the disease.

In some embodiments, the antigen may be one that is associated with cancer, an infectious disease, or an addiction disease.

Viruses, or parts thereof, that may be useful as antigens in the compositions herein include for example, and without limitation, Cowpoxvirus, Vaccinia virus, Pseudocowpox virus, herpes virus, Human herpesvirus 1, Human herpesvirus 2, Cytomegalovirus, Human adenovirus A-F, Polyomavirus, human papillomavirus (HPV), Parvovirus, Hepatitis A virus, Hepatitis B virus, Hepatitis C virus, human immunodeficiency virus (HIV), Orthoreovirus, Rotavirus, Ebola virus, parainfluenza virus, influenza virus (e.g. H5N1 influenza virus, influenza A virus, influenza B virus, influenza C virus), Measles virus, Mumps virus, Rubella virus, Pneumovirus, respiratory syncytial virus, human respiratory syncytial virus, Rabies virus, California encephalitis virus, Japanese encephalitis virus, Hantaan virus, Lymphocytic choriomeningitis virus, Coronavirus, Enterovirus, Rhinovirus, Poliovirus, Norovirus, Flavivirus, Dengue virus, West Nile virus, Yellow fever virus and varicella.

In an embodiment, a composition disclosed herein comprises an antigen that may potentially be useful for treating and/or preventing an influenza virus infection in a subject in need thereof. Influenza is a single-stranded RNA virus of the family Orthomyxoviridae and is often characterized based on two large glycoproteins on the outside of the viral particle, hemagglutinin (HA) and neuraminidase (NA). Numerous HA subtypes of influenza A have been identified (Kawaoka et al., Virology (1990) 179:759-767; Webster et al., "Antigenic variation among type A influenza viruses," p. 127-168. In: P. Palese and D. W. Kingsbury (ed.), Genetics of influenza viruses. Springer-Verlag, New York). In some embodiments, the antigen may be derived from the HA or NA glycoproteins.

In another embodiment, a composition disclosed herein comprises an antigen that may potentially be useful for treating and/or preventing an Ebola virus infection in a subject in need thereof.

In another embodiment, a composition disclosed herein comprises an antigen that may potentially be useful for treating and/or preventing a human papillomavirus (HPV) infection in a subject in need thereof. In more particular embodiments, a composition disclosed herein comprises an antigen that may potentially be useful for treating and/or preventing a HPV-related cervical cancer or HPV-related head and neck cancer. In some embodiments, the antigen is a peptide comprising the sequence RAHYNIVTF (HPV16E7 (H-2Db) peptide 49-67; R9F; SEQ ID NO: 1).

In another embodiment, a composition disclosed herein comprises an antigen that may potentially be useful for treating and/or preventing a respiratory syncytial virus (RSV) infection in a subject in need thereof. In more particular embodiments, a composition disclosed herein comprises an antigen that may potentially be useful for treating and/or preventing a lung disease associated with a RSV infection.

Bacteria or parts thereof that may be useful as antigens in the compositions herein include for example, and without limitation, Anthrax (*Bacillus anthracis*), *Brucella*, *Bordetella pertussis*, *Candida*, *Chlamydia pneumoniae*, *Chlamydia psittaci*, *Cholera*, *Clostridium botulinum*, *Coccidioides immitis*, *Cryptococcus*, *Diphtheria*, *Escherichia coli* 0157: H7, Enterohemorrhagic *Escherichia coli*, Enterotoxigenic *Escherichia coli*, *Haemophilus influenzae*, *Helicobacter pylori*, *Legionella*, *Leptospira*, *Listeria*, *Meningococcus*, *Mycoplasma pneumoniae*, *Mycobacterium*, *Pertussis*, *Pneumonia*, *Salmonella*, *Shigella*, *Staphylococcus*, *Streptococcus pneumoniae* and *Yersinia enterocolitica*.

In an embodiment, a composition disclosed herein comprises an antigen that may potentially be useful for treating and/or preventing a *Bacillus anthracis* infection (i.e. Anthrax) in a subject in need thereof. Without limitation, the antigen contained in the vaccine may for example be anthrax recombinant protective antigen (rPA) (List Biological Laboratories, Inc.; Campbell, Calif.) or anthrax mutant recombinant protective antigen (mrPA) (Pfenex, Inc.; San Diego, Calif.).

Protozoa or parts thereof that may be useful as antigens in the compositions herein include for example, and without limitation, the genus *Plasmodium* (*Plasmodium falciparum*, *Plasmodium malariae*, *Plasmodium vivax*, *Plasmodium ovale* or *Plasmodium knowlesi*), which causes malaria.

In an embodiment, a composition disclosed herein comprises an antigen that may potentially be useful for treating and/or preventing a *Plasmodium malariae* infection (i.e. malaria) in a subject in need thereof.

The antigen may alternatively be a naturally occurring or synthesized toxin or allergen. A "toxin", as used herein, refers to any substance produced by living cells or organisms (e.g. plants, animals, microorganisms, etc.) that is capable of causing a disease or ailment, or an infectious substance, or a recombinant or synthesized molecule capable of adverse effect. Toxins may be for example small molecules, peptides, or proteins. Toxins include drug substances such as, for example, cocaine. The toxin may be capable of being neutralized by an antibody. In such embodiments, the antigen may elicit the production of antibodies that bind to and sequester the toxin in circulation (e.g. the blood), thereby potentially preventing its delivery to another area of the body (e.g. the brain).

An "allergen", as used herein, refers to any substance that can cause an allergy. The allergen may be derived from, without limitation, cells, cell extracts, proteins, polypeptides, peptides, polysaccharides, polysaccharide conjugates, peptide and non-peptide mimics of polysaccharides and other molecules, small molecules, lipids, glycolipids, and carbohydrates of plants, animals, fungi, insects, food, drugs, dust, and mites. Allergens include but are not limited to environmental aeroallergens; plant pollens (e.g. ragweed/hayfever); weed pollen allergens; grass pollen allergens; Johnson grass; tree pollen allergens; ryegrass; arachnid allergens (e.g. house dust mite allergens); storage mite allergens; Japanese cedar pollen/hay fever; mold/fungal spore allergens; animal allergens (e.g., dog, guinea pig, hamster, gerbil, rat, mouse, etc., allergens); food allergens (e.g. crustaceans; nuts; citrus fruits; flour; coffee); insect allergens (e.g. fleas, cockroach); venoms: (Hymenoptera, yellow jacket, honey bee, wasp, hornet, fire ant); bacterial allergens (e.g. streptococcal antigens; parasite allergens such as *Ascaris* antigen); viral antigens; drug allergens (e.g. penicillin); hormones (e.g. insulin); enzymes (e.g. streptokinase); and drugs or chemicals capable of acting as incomplete antigens or haptens (e.g. the acid anhydrides and the isocyanates).

Where a hapten is used in a composition of the invention, it may be attached to a carrier, such as for example a protein, to form a hapten-carrier adduct. The hapten-carrier adduct is capable of eliciting an immune response, whereas the hapten itself would not typically elicit a response. Non-limiting examples of haptens are aniline, urushiol (a toxin in poison ivy), hydralazine, fluorescein, biotin, digoxigenin and dinitrophenol.

In another embodiment, the antigen may be an antigen associated with a disease where it is desirable to sequester the antigen in circulation, such as for example an amyloid protein (e.g. Alzheimer's disease). Thus, in some embodiments, a composition of the invention comprises an antigen that may potentially be useful in the treatment and/or prevention of a neurodegenerative disease in a subject in need thereof, wherein the neurodegenerative disease is associated with the expression of the antigen.

In another embodiment, the antigen may be any one or more of the antigens disclosed in WO 2007/041832, such as for example the peptide antigens disclosed in Table 1 at pages 17-19 of WO 2007/041832.

For example, and without limitation, polypeptides or fragments thereof that may be useful as antigens in the compositions herein include those derived from Cholera toxoid, tetanus toxoid, diphtheria toxoid, hepatitis B surface antigen, hemagglutinin (e.g. H5N1 recombinant hemagglutinin protein), anthrax recombinant protective antigen (List Biological Laboratories, Inc.; Campbell, Calif.), anthrax mutant recombinant protective antigen (Pfenex, Inc.; San Diego, Calif.), neuraminidase, influenza M protein, PfHRP2, pLDH, aldolase, MSP1, MSP2, AMA1, Der-p-1, Der-f-1, Adipophilin, AFP, AIM-2, ART-4, BAGE, α-feto protein, BCL-2, Bcr-Abl, BING-4, CEA, CPSF, CT, cyclin D1Ep-CAM, EphA2, EphA3, ELF-2, FGF-5, G250, Gonadotropin Releasing Hormone (GNRH), HER-2, intestinal carboxyl esterase (iCE), IL13Rα2, MAGE-1, MAGE-2, MAGE-3, MART-1, MART-2, M-CSF, MDM-2, MMP-2, MUC-1, NY-EOS-1, MUM-1, MUM-2, MUM-3, pertussis toxoid protein, p53, PBF, PRAME, PSA, PSMA, RAGE-1, RNF43, RU1, RU2AS, SART-1, SART-2, SART-3, SAGE-1, SCRN 1, SOX2, SOX10, STEAP1, survivin, Telomerase, TGFβRII, TRAG-3, TRP-1, TRP-2, TERT and VVT1.

The term "polypeptide" encompasses any chain of amino acids, regardless of length (e.g., at least 6, 8, 10, 12, 14, 16, 18, or 20 amino acids) or post-translational modification (e.g., glycosylation or phosphorylation), and includes, for example, natural proteins, synthetic or recombinant polypeptides and peptides, epitopes, hybrid molecules, variants, homologs, analogs, peptoids, peptidomimetics, etc. A variant or derivative therefore includes deletions, including truncations and fragments; insertions and additions, for example conservative substitutions, site-directed mutants and allelic variants; and modifications, including peptoids having one or more non-amino acyl groups (for example, sugar, lipid, etc.) covalently linked to the peptide and post-translational modifications. As used herein, the term "conserved amino acid substitutions" or "conservative substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Specific, non-limiting examples of a conservative substitution include the following examples:

| Original Residue | Conservative Substitution |
| --- | --- |
| Ala | Ser |
| Arg | Lys |
| Asn | Gln, His |
| Asp | Glu |
| Cys | Ser |
| Gln | Asn |
| Glu | Asp |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Val | Ile, Leu |

Polypeptides or peptides that have substantial identity to an antigen sequence may be used. Two sequences are considered to have substantial identity if, when optimally aligned (with gaps permitted), they share at least approximately 50% sequence identity, or if the sequences share defined functional motifs. In alternative embodiments, optimally aligned sequences may be considered to be substantially identical (i.e., to have substantial identity) if they share at least 60%, 70%, 75%, 80%, 85%, 90%, 95%, 96%, 97%, 98%, 99% identity over a specified region. The term "identity" refers to sequence similarity between two polypeptides molecules. Identity can be determined by comparing each position in the aligned sequences. A degree of identity between amino acid sequences is a function of the number of identical or matching amino acids at positions shared by the sequences, for example, over a specified region. Optimal alignment of sequences for comparisons of identity may be conducted using a variety of algorithms, as are known in the art, including the ClustalW program, available at http://clustalw.qenome.ad.ip, the local homology algorithm of Smith and Waterman, 1981, Adv. Appl. Math 2: 482, the homology alignment algorithm of Needleman and Wunsch, 1970, *J. Mol. Biol.* 48:443, the search for similarity method of Pearson and Lipman, 1988, Proc. Natl. Acad. Sci. USA 85:2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). For example, the "BLAST 2 Sequences" tool, available through the National Center for Biotechnology Information (through the internet at http://www.ncbi.nlm.nih.qov/BLAST/bl2seq/wblast2.cqi) may be used, selecting the "blastp" program at the following default settings: expect threshold 10; word size 3; matrix BLOSUM 62; gap costs existence 11, extension 1. In another embodiment, the person skilled in the art can readily and properly align any given sequence and deduce sequence identity and/or homology by mere visual inspection.

Polypeptides and peptides used to practice the invention can be isolated from natural sources, be synthetic, or be recombinantly generated polypeptides. Peptides and proteins can be recombinantly expressed in vitro or in vivo. The peptides and polypeptides used to practice the invention can be made and isolated using any method known in the art. Polypeptide and peptides used to practice the invention can also be synthesized, whole or in part, using chemical methods well known in the art. See e.g., Caruthers (1980) Nucleic Acids Res. Symp. Ser. 215-223; Hom (1980) Nucleic Acids Res. Symp. Ser. 225-232; Banga, A. K, Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

In some embodiments, the antigen may be a purified antigen, e.g., from about 25% to 50% pure, from about 50% to about 75% pure, from about 75% to about 85% pure, from about 85% to about 90% pure, from about 90% to about 95% pure, from about 95% to about 98% pure, from about 98% to about 99% pure, or greater than 99% pure.

As noted above, the term "antigen" also includes a polynucleotide that encodes the polypeptide that functions as an antigen. As used herein, the term "polynucleotide" encompasses a chain of nucleotides of any length (e.g. 9, 12, 18, 24, 30, 60, 150, 300, 600, 1500 or more nucleotides) or number of strands (e.g. single-stranded or double-stranded). Polynucleotides may be DNA (e.g. genomic DNA or cDNA) or RNA (e.g. mRNA) or combinations thereof. They may be naturally occurring or synthetic (e.g. chemically synthesized). It is contemplated that the polynucleotide may contain modifications of one or more nitrogenous bases, pentose sugars or phosphate groups in the nucleotide chain. Such modifications are well-known in the art and may be for the purpose of e.g. improving stability of the polynucleotide.

The polynucleotide may be delivered in various forms. In some embodiments, a naked polynucleotide may be used, either in linear form, or inserted into a plasmid, such as an expression plasmid. In other embodiments, a live vector such as a viral or bacterial vector may be used.

One or more regulatory sequences that aid in transcription of DNA into RNA and/or translation of RNA into a polypeptide may be present. In some instances, such as in the case of a polynucleotide that is a messenger RNA (mRNA) molecule, regulatory sequences relating to the transcription process (e.g. a promoter) are not required, and protein expression may be effected in the absence of a promoter. The skilled artisan can include suitable regulatory sequences as the circumstances require.

In some embodiments, the polynucleotide is present in an expression cassette, in which it is operably linked to regulatory sequences that will permit the polynucleotide to be expressed in the subject to which the composition of the invention is administered. The choice of expression cassette depends on the subject to which the composition is administered as well as the features desired for the expressed polypeptide.

Typically, an expression cassette includes a promoter that is functional in the subject and can be constitutive or inducible; a ribosome binding site; a start codon (ATG) if necessary; the polynucleotide encoding the polypeptide of interest; a stop codon; and optionally a 3' terminal region (translation and/or transcription terminator). Additional sequences such as a region encoding a signal peptide may be included. The polynucleotide encoding the polypeptide of interest may be homologous or heterologous to any of the other regulatory sequences in the expression cassette. Sequences to be expressed together with the polypeptide of interest, such as a signal peptide encoding region, are typically located adjacent to the polynucleotide encoding the protein to be expressed and placed in proper reading frame. The open reading frame constituted by the polynucleotide encoding the protein to be expressed solely or together with any other sequence to be expressed (e.g. the signal peptide), is placed under the control of the promoter so that transcription and translation occur in the subject to which the composition is administered.

The amount of antigen used in a single treatment with a composition as described herein may vary depending on the type of antigen and characteristics of the subject (e.g. size, weight, age, sex, etc). One skilled in the art will be able to determine, without undue experimentation, the effective amount of antigen to use in a particular application. The term "effective amount" as used herein means an amount effective, at dosages and for periods of time necessary, to achieve the desired result.

Cancer-Associated Antigens

In some embodiments, the antigen may be a cancer or tumor-associated protein or a fragment thereof. Many cancer or tumor-associated proteins are known in the art. Without limitation, the antigen may be from a membrane surface-bound cancer-associated protein. The surface-bound cancer-associated protein (or antigen thereof) may be capable of being recognized by an antibody.

In some embodiments, the cancer may be caused by a pathogen, such as a virus. Viruses linked to the development of cancer are known to the skilled person and include, but are not limited to, human papillomaviruses (HPV), John Cunningham virus (JCV), Human herpes virus 8, Epstein Barr Virus (EBV), Merkel cell polyomavirus, Hepatitis C Virus and Human T cell leukaemia virus-1. Thus, in an embodiment, a composition disclosed herein may comprise an antigen associated a virus that is linked to the development of cancer.

In a particular embodiment, the pharmaceutical or vaccine compositions of the invention, which include a lipid A mimic as disclosed herein, may comprise one or more survivin antigens.

Survivin, also called baculoviral inhibitor of apoptosis repeat-containing 5 (BIRC5), is a protein involved in the negative regulation of apoptosis. It has been classed as a member of the family of inhibitors of apoptosis proteins (IAPs). Survivin is a 16.5 kDa cytoplasmic protein containing a single BIR motif and a highly charged carboxy-terminal coiled region instead of a RING finger. The gene coding for survivin is nearly identical to the sequence of Effector Cell Protease Receptor-1 (EPR-1), but oriented in the opposite direction. The coding sequence for the survivin (*Homo sapiens*) is 429 nucleotides long (SEQ ID NO: 2) including stop codons. The encoded protein survivin (*Homo sapiens*) is 142 amino acids long (SEQ ID NO: 3).

It is postulated that the survivin protein functions to inhibit caspase activation, thereby leading to negative regulation of apoptosis or programmed cell death. Consistent with this function, survivin has been identified as one of the top genes invariably up-regulated in many types of cancer but not in normal tissue (see e.g. Altieri et al., Lab Invest, 79: 1327-1333, 1999; and U.S. Pat. No. 6,245,523). This fact therefore makes survivin an ideal target for cancer therapy as cancer cells are targeted while normal cells are not. Indeed, survivin is highly expressed in many tumor types, including a large portion of human cancer, and has reported prognostic value.

In some embodiments, vaccines of the invention may comprise one or more survivin antigens. As used herein, the term "survivin antigen" encompasses any peptide, polypeptide or variant thereof (e.g. survivin peptide variant) derived from a survivin protein or a fragment thereof. The term "survivin antigen" also encompasses a polynucleotide that encodes a survivin peptide, survivin peptide variant or survivin peptide functional equivalent described herein. Polynucleotides may be DNA (e.g. genomic DNA or cDNA) or RNA (e.g. mRNA) or combinations thereof. They may be naturally occurring or synthetic (e.g. chemically synthesized). It is contemplated that the polynucleotide may contain modifications of one or more nitrogenous bases, pentose sugars or phosphate groups in the nucleotide chain. Such modifications are well-known in the art and may be for the purpose of e.g. improving stability of the polynucleotide.

In an embodiment, the survivin antigen may comprise the full length survivin polypeptide or a nucleic acid encoding the full length survivin polypeptide. Alternatively, the survivin antigen may be a survivin peptide comprising a fragment of any length of the survivin protein. Exemplary embodiments include a survivin peptide that comprises at least 5, 6, 7, 8, 9, 10, 11, 12, 13, 14, 15, 16, 17, 18, 19 or 20 amino acid residues. In specific embodiments, the survivin peptide consists of a heptapeptide, an octapeptide, a nonapeptide, a decapeptide or an undecapeptide, consisting of 7, 8, 9, 10, 11 consecutive amino acid residues of the survivin protein (e.g. SEQ ID NO: 3), respectively. Particular embodiments of the survivin antigen include survivin peptides of about 9 or 10 amino acids.

Survivin antigens of the invention also encompass variants and functional equivalents of survivin peptides. Variants or functional equivalents of a survivin peptide encompass peptides that exhibit amino acid sequences with differences as compared to the specific sequence of the survivin protein, such as one or more amino acid substitutions, deletions or additions, or any combination thereof. The difference may be measured as a reduction in identity as between the survivin protein sequence and the survivin peptide variant or survivin peptide functional equivalent.

The identity between amino acid sequences may be calculated using algorithms well known in the art. Survivin peptide variants or functional equivalents are to be considered as falling within the meaning of a "survivin antigen" of the invention when they are, over their entire length, at least 70% identical to a peptide sequence of a survivin protein, such as at least 75% identical, at least 80% identical, at least 85% identical, at least 90% identical, or at least 95% identical, including 96%, 97%, 98% or 99% identical with a peptide sequence of a survivin protein. In a particular embodiment, the survivin peptide variant has a sequence that is at least 85%, 90%, 95%, 96%, 97%, 98% or 99% identical to a consecutive amino acid sequence of SEQ ID NO: 3.

The survivin protein from which the survivin antigen can be derived is a survivin protein from any animal species in which the protein is expressed. A particular embodiment is the survivin protein from humans (SEQ ID NO: 3). Based on the sequence of the selected survivin protein, the survivin antigen may be derived by any appropriate chemical or enzymatic treatment of the survivin protein or coding nucleic acid. Alternatively, the survivin antigen may be synthesized by any conventional peptide or nucleic acid synthesis procedure with which the person of ordinary skill in the art is familiar.

The survivin antigen (peptide or nucleic acid) may have a sequence which is a native sequence of survivin. Alternatively, the survivin antigen may be a peptide or nucleic acid sequence modified by one or more substitutions, deletions or additions, such as e.g. the survivin peptide variants or functional equivalents described herein. Exemplary procedures and modifications of survivin peptides that increase the immunogenicity of the peptides include, for example, those described in WO 2004/067023 involving amino acid substitutions introduced at anchor positions which increase peptide binding to the HLA class I molecule.

In an embodiment, the survivin antigen is any peptide derived from the survivin protein, or any survivin peptide variant thereof, that is capable of binding MHC Class I HLA molecules. Along these lines, the survivin antigen may be any survivin peptide, or survivin peptide variant thereof, that is capable of inducing or potentiating an immune response in a subject.

In an embodiment, the survivin antigen is a peptide antigen comprising an amino acid sequence from the survivin protein (SEQ ID NO: 3) that is capable of eliciting a cytotoxic T-lymphocyte (CTL) response in a subject, or a nucleic acid molecule encoding said peptide.

In an embodiment, the vaccine comprises one or more synthetic survivin peptides, or variants thereof, based on the amino acid sequence of the survivin protein, such as the amino acid sequence set forth in SEQ ID NO: 3.

Survivin peptides, survivin peptide variants and survivin functional equivalents, and their use for diagnostic and therapeutic purposes, specifically in cancer, have been described, for example, in WO 2004/067023 and WO 2006/081826. The novel peptides disclosed in these publications were found to be capable of eliciting cytotoxic T-lymphocyte (CTL) responses in cancer patients. In particular, in WO 2004/067023, it was found that MHC Class I restricted peptides can be derived from the survivin protein, which are capable of binding to MHC Class I HLA molecules and thereby eliciting both ex vivo and in situ CTL immune responses in patients suffering from a wide range of cancer diseases.

In an embodiment, a vaccine composition of the invention may include any one or more of the survivin peptides, survivin peptide variants or survivin peptide functional equivalents disclosed in WO 2004/067023 and WO 2006/081826.

In another embodiment, a vaccine composition of the invention may include one or more of a survivin peptide, survivin peptide variant or survivin peptide functional equivalent having the ability to bind any of the MHC Class I molecules selected from HLA-A, HLA-B or HLA-C molecules.

Exemplary MHC Class I HLA-A molecules to which the survivin peptide, survivin peptide variant, or survivin peptide functional equivalent may bind include, without limitation, HLA-A1, HLA-A2, HLA-A3, HLA-A9, HLA-A10, HLA-A11, HLA-A19, HLA-A23, HLA-A24, HLA-A25, HLA-A26, HLA-A28, HLA-A29, HLA-A30, HLA-A31, HLA-A32, HLA-A33, HLA-A34, HLA-A36, HLA-A43, HLA-A66, HLA-A68, and HLA-A69.

Exemplary MHC Class I HLA-B molecules to which the survivin peptide, survivin peptide variant, or survivin peptide functional equivalent may bind include, without limitation, HLA-B5, HLA-B7, HLA-B8, HLA-B12, HLA-B13, HLA-B14, HLA-B15, HLA-B16, HLA-B17, HLA-B18, HLA-B21, HLA-B22, HLA-B27, HLA-B35, HLA-B37, HLA-B38, HLA-B39, HLA-B40, HLA-B41, HLA-B42, HLA-B44, HLA-B45, HLA-B46 and HLA-B47.

Exemplary MHC Class I HLA-C molecules to which the survivin peptide, survivin peptide variant, or survivin peptide functional equivalent may bind include, without limitation, HLA-C1, HLA-C2, HLA-C3, HLA-C4, HLA-C5, HLA-C6, HLA-C7 and HLA-C16.

In a particular embodiment, a vaccine composition of the invention may comprise one or more of the survivin peptide antigens selected from: $P_{GF}\text{-}7_6, D_{NA}$

|   |   |   |
|---|---|---|
| i) | FEELTLGEF [HLA-A1] | (SEQ ID NO: 4) |
| ii) | FTELTLGEF [HLA-A1] | (SEQ ID NO: 5) |
| iii) | LTLGEFLKL [HLA-A2] | (SEQ ID NO: 6) |
| iv) | LMLGEFLKL [HLA-A2] | (SEQ ID NO: 7) |
| v) | RISTFKNWPF [HLA-A3] | (SEQ ID NO: 8) |
| vi) | RISTFKNWPK [HLA-A3] | (SEQ ID NO: 9) |
| vii) | STFKNWPFL [HLA-A24] | (SEQ ID NO: 10) |
| viii) | LPPAWQPFL [HLA-B7] | (SEQ ID NO: 11) |

The above-listed survivin peptides represent, without limitation, exemplary MHC Class I restricted peptides encompassed by the invention. The specific MHC Class I HLA molecule to which each of the survivin peptides is believed to bind is shown on the right in square brackets. A vaccine of the invention may comprise one or more of these survivin peptides, in any suitable combination.

In a further embodiment, a vaccine composition of the invention may comprise any one or more of the five survivin peptides listed below, in any suitable combination:

|   |   |   |
|---|---|---|
| i) | FTELTLGEF [HLA-A1] | (SEQ ID NO: 5) |
| ii) | LMLGEFLKL [HLA-A2] | (SEQ ID NO: 7) |
| iii) | RISTFKNWPK [HLA-A3] | (SEQ ID NO: 9) |
| iv) | STFKNWPFL [HLA-A24] | (SEQ ID NO: 10) |
| v) | LPPAWQPFL [HLA-B7] | (SEQ ID NO: 11) |

In a particular embodiment, the composition of the invention comprises all five of the survivin peptide antigens listed above.

In some embodiments, in addition to the at least one survivin antigen, a vaccine composition of the invention may comprise one or more additional antigens, such as for example those described herein.

CTL Epitopes and B Cell Epitopes

As mentioned above, in some embodiments, the antigen is a molecule comprising at least one B cell epitope or CTL epitope.

The epitopes may be of any chemical nature, including without limitation peptides, carbohydrates, lipids, glycopeptides and glycolipids. In particular embodiments, the epitopes are peptides derived from any of the antigens described herein. The epitope may be identical to a naturally occurring epitope, or may be a modified form of a naturally occurring epitope.

B cell epitopes are epitopes recognized by B cells and by antibodies. B cell peptide epitopes are typically at least five amino acids, more often at least six amino acids, still more often at least seven or eight amino acids in length, and may be continuous ("linear") or discontinuous ("conformational"); the latter being formed, for example, by the folding of a protein to bring non-contiguous parts of the primary amino acid sequence into physical proximity. B cell epitopes may also be carbohydrate epitopes.

In an embodiment, the antigen of the compositions described herein may be or comprise a B cell epitope capable of inducing a humoral immune response.

In some embodiments, the antigen of the compositions described herein may be or comprise a B cell epitope associated with an infectious disease. For example, the antigen may be or comprise a B cell epitope derived from a virus, such as for example influenza virus or respiratory syncytial virus. In another embodiment, the B cell epitope may be an epitope derived from the hemagglutinin glycoprotein of the H5N1 influenza virus.

In another embodiment, the antigen of the compositions described herein may be or comprise a B cell epitope derived from a bacterium, such as for example *Bordetella pertussis* or *Bacillus anthracis*. In a particular embodiment, the B cell epitope may be an epitope of the pertussis toxoid protein produced by *Bordetella pertussis*. In another particular embodiment, the B cell epitope may be an epitope of the anthrax recombinant protective antigen (rPA) or the anthrax mutant recombinant protective antigen (mrPA).

In another embodiment, the antigen of the compositions described herein may be or comprise a B cell epitope derived from a protozoan, such as from the genus *Plasmodium*.

In a further embodiment, the composition may comprise a mixture of B cell epitopes as antigens for inducing a humoral immune response. The B cell epitopes may be linked to form a single polypeptide.

CTL epitopes are molecules recognized by cytotoxic T lymphocytes. CTL epitopes are typically presented on the surface of an antigen-presenting cell, complexed with MHC molecules. As used herein, the term "CTL epitope" refers to a molecule (e.g. peptide) which is substantially the same as a natural CTL epitope of an antigen (including a hapten). The CTL epitope may be modified as compared to its natural counterpart, such as by one or two amino acids. Unless otherwise stated, reference herein to a CTL epitope is to an unbound molecule that is capable of being taken up by cells and presented on the surface of an antigen-presenting cell.

The CTL epitope should typically be one that is amendable to recognition by T cell receptors so that a cell-mediated immune response can occur. For peptides, CTL epitopes may interact with class I or class II MHC molecules. CTL epitopes presented by MHC class I molecules are typically peptides between 8 and 15 amino acids in length, and more often between 9 and 11 amino acids in length. CTL epitopes presented by MHC class II molecules are typically peptides between 5 and 24 amino acids in length, and more often between 13 and 17 amino acids in length. If the antigen is larger than these sizes, it will be processed by the immune system into fragments of a size more suitable for interaction with MHC class I or II molecules. Therefore, CTL epitopes may be part of larger peptide than those mentioned above.

Many CTL epitopes are known. Several techniques of identifying additional CTL epitopes are recognized by the art. In general, these involve preparing a molecule which potentially provides a CTL epitope and characterizing the immune response to that molecule.

In an embodiment, the antigen of the compositions described herein may be or comprise a CTL epitope capable of inducing a CTL response. For example, the antigen may be a CTL epitope derived from a virus, such as HPV.

In another embodiment, the antigen may be or comprise a CTL epitope derived from the E6 or E7 protein of HPV. For example, and without limitation, the CTL epitope of E6 protein of HPV may comprise the peptide sequence TIHDIILECV (T10V) (SEQ ID NO: 12) and the CTL epitope of the E7 protein of HPV may comprise the peptide sequence RAHYNIVTF (R9F) (SEQ ID NO: 1), YMLDLQPETT (Y10T) (SEQ ID NO: 13), LLMGTLGIV (L9V) (SEQ ID NO: 14), and TLGIVCPI (T81) (SEQ ID NO: 15).

In another embodiment, the CTL epitope may be an epitope of a tumor-associated protein, such as for example, one or more of the survivin peptides described herein or a melanoma-associated protein. In an embodiment, the melanoma-associated protein may be a tyrosine related protein-2 (TRP-2) or p53, which can be obtained by various methods including recombinant technology or chemical synthesis.

For example, and without limitation, the CTL epitope of a TRP-2 derived protein may comprise the peptide sequence SVYDFFVWL (S9L; SEQ ID NO: 16) or VYDFFVWL (V8L; SEQ ID NO: 17). The CTL epitope of a p53 derived protein may comprise, for example, the peptide sequence KYMCNSSCM (K9M; wild type p53; SEQ ID NO: 18), KYICNSSCM (mK9M; modified p53; SEQ ID NO: 19) or AKXVAAVVTLKAAAKYICNSSCM (mK9M fusion with T-helper epitope; SEQ ID NO: 20).

In a further embodiment, the composition may comprise a mixture of CTL epitopes as antigens for inducing a CTL response. The CTL epitopes may be linked to form a single polypeptide.

In some embodiments, the B cell and CTL epitopes are disease-associated and/or disease-specific epitopes. Such diseases include, but are not limited to, any of those described earlier herein. For example, and without limitation, the disease may be a cancer (such as, for example, breast cancer, ovarian cancer, prostate cancer, glioblastoma or diffuse large B cell lymphoma), an infectious disease (such as, for example, a disease caused by or associated with human papillomavirus (HPV) infection, respiratory syncytial virus (RSV) infection, influenza virus infection, Ebola virus infection, *Bacillus anthracis* infection, or *Plasmodium malariae* infection) or an addiction disease (such as, for example, addiction to cocaine).

T-Helper Epitopes

In some embodiments, the pharmaceutical or vaccine compositions of the invention, which include a lipid A mimic as disclosed herein, may also comprise at least one T-helper epitope or T-helper antigen.

T-helper epitopes are a sequence of amino acids (natural or non-natural amino acids) that have T-helper activity. T-helper epitopes are recognised by T-helper lymphocytes, which play an important role in establishing and maximising the capabilities of the immune system, and are involved in activating and directing other immune cells, such as for example cytotoxic T lymphocytes.

A T-helper epitope can consist of a continuous or discontinuous epitope. Hence not every amino acid of a T-helper is necessarily part of the epitope. Accordingly, T-helper epitopes, including analogs and segments of T-helper epitopes, are capable of enhancing or stimulating an immune response. Immunodominant T-helper epitopes are broadly reactive in animal and human populations with widely divergent MHC types (Celis et al. (1988) *J. Immunol.* 140:1808-1815; Demotz et al. (1989) *J. Immunol.* 142:394-402; Chong et al. (1992) *Infect. Immun.* 60:4640-4647). The T-helper domain of the subject peptides may have from about 10 to about 50 amino acids, and more particularly about 10 to about 30 amino acids. When multiple T-helper epitopes are present, then each T-helper epitope acts independently.

In some embodiments, the T-helper epitope may form part of an antigen described herein. In particular, if the antigen is of sufficient size, it may contain an epitope that functions as a T-helper epitope. In other embodiments, the T-helper epitope is a separate molecule from the antigen.

In another embodiment, T-helper epitope analogs may include substitutions, deletions and insertions of from one to about 10 amino acid residues in the T-helper epitope. T-helper segments are contiguous portions of a T-helper epitope that are sufficient to enhance or stimulate an immune response. An example of T-helper segments is a series of overlapping peptides that are derived from a single longer peptide.

In a particular embodiment, the compositions of the invention may comprise as a T-helper epitope or antigen, the modified Tetanus toxin peptide A16L (830 to 844; AQYIKANSKFIGITEL (SEQ ID NO: 21), with an alanine residue added to its amino terminus to enhance stability (Slingluff et al., Clin Cancer Res., 7: 3012-3024, 2001).

Other sources of T-helper epitopes which may be used in the present compositions include, for example, hepatitis B surface antigen helper T cell epitopes, pertussis toxin helper T cell epitopes, measles virus F protein helper T cell epitope, *Chlamydia trachomitis* major outer membrane protein helper T cell epitope, diphtheria toxin helper T cell epitopes, *Plasmodium falciparum* circumsporozoite helper T cell epitopes, *Schistosoma mansoni* triose phosphate isomerase helper T cell epitopes, *Escherichia coli* TraT helper T cell epitopes and immune-enhancing analogs and segments of any of these T-helper epitopes.

In some embodiments, the T-helper epitope may be a universal T-helper epitope. A universal T-helper epitope as used herein refers to a peptide or other immunogenic molecule, or a fragment thereof, that binds to a multiplicity of MHC class II molecules in a manner that activates T cell function in a class II (CD4+ T cells)-restricted manner. An example of a universal T-helper epitope is PADRE (pan-DR epitope) comprising the peptide sequence AKXVAAVVTL-KAAA (SEQ ID NO: 22), wherein X may be cyclohexylalanyl. PADRE specifically has a CD4+ T-helper epitope, that is, it stimulates induction of a PADRE-specific CD4+ T-helper response.

In addition to the modified tetanus toxin peptide A16L mentioned earlier, Tetanus toxoid has other T-helper epitopes that work in the similar manner as PADRE. Tetanus and diphtheria toxins have universal epitopes for human CD4+ cells (Diethelm-Okita, B. M. et al., *J. Infect. Diseases,* 181:1001-1009, 2000). In another embodiment, the T-helper epitope may be a tetanus toxoid peptide such as F21E comprising the peptide sequence FNNFTVSFWLRVPKVSASHLE (amino acids 947-967; SEQ ID NO: 23).

In certain embodiments, the T-helper epitope is fused to at least one of the one or more antigens in the vaccine of the invention (e.g. a fusion peptide).

Liposomes and Lipid-Based Particles or Vesicles, and Formulations Thereof

In some embodiments, the pharmaceutical or vaccine compositions of the invention comprise liposomes. In a particular embodiment, liposomes are included when the vaccine compositions comprise a carrier comprising a continuous phase of a hydrophobic substance as described herein. Because liposomes can be formulated with bulk lipid molecules that are also found in natural cellular membranes, liposomes generally can be administered safely and are biodegradable.

Liposomes are completely closed lipid bilayer membranes containing an entrapped aqueous volume. Liposomes may be unilamellar vesicles (possessing a single bilayer membrane) or multilamellar vesicles characterized by multimembrane bilayers, each bilayer may or may not be separated from the next by an aqueous layer. A general discussion of liposomes can be found in Gregoriadis G. *Immunol. Today,* 11:89-97, 1990; and Frezard, F., *Braz. J. Med. Bio. Res.,* 32:181-189, 1999.

Liposomes can adsorb to virtually any type of cell and then release an incorporated agent (e.g. antigen). Alternatively, the liposome can fuse with the target cell, whereby the contents of the liposome empty into the target cell. Alternatively, a liposome may be endocytosed by cells that are phagocytic.

It is also envisioned that lipids may form lipid-based particles or vesicles in a continuous oil medium. Therefore, in some embodiments, the pharmaceutical or vaccine compositions of the invention may comprise for example, and without limitation, single layer lipid vesicles. These single layer lipid vesicles may be present alone or together with bilayer liposomes in the same composition. In some embodiments, the lipids form other lipid-based particles besides single layer lipid vesicles.

As used herein and in the claims, the term "liposomes" is intended to encompass all such vesicular structures as described above, including, without limitation, those described in the art as "niosomes", "transfersomes" and "virosomes". Other suitable liposomes that may be used include multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). The skilled artisan will recognize that the techniques for preparing these liposomes are well known in the art (see e.g. Kreuter, J., ed., Colloidal Drug Delivery Systems, vol. 66, Marcel Dekker, Inc., 1994).

Although any liposomes may be used in this invention, including liposomes made from archaebacterial lipids, particular embodiments of liposomes use phospholipids and unesterified cholesterol in the liposome formulation. The cholesterol is used to stabilize the liposomes and any other compound that stabilizes liposomes may replace the cholesterol. Other liposome stabilizing compounds are known to those skilled in the art. For example, saturated phospholipids produce liposomes with higher transition temperatures indicating increased stability.

Phospholipids that may be used in the preparation of liposomes include for example, and without limitation, those with at least one head group selected from the group consisting of phosphoglycerol, phosphoethanolamine, phosphoserine, phosphocholine (e.g. DOPC; 1,2-Dioleoyl-sn-glycero-3-phosphocholine) and phosphoinositol. In some embodiments, the liposomes are prepared using a mixture of DOPC and cholesterol in, for example, a DOPC:cholesterol ratio of 10:1 w/w. Thus, when unesterified cholesterol is also used in the liposome formulation, the cholesterol may be used in an amount equivalent to about 10% of the weight of phospholipid. If a compound other than cholesterol is used to stabilize the liposomes, one skilled in the art can readily determine the amount needed in the composition.

Liposome compositions may be obtained, for example, by using natural lipids, synthetic lipids, sphingolipids, ether lipids, sterols, cardiolipin, cationic lipids and lipids modified with poly (ethylene glycol) and other polymers. Synthetic lipids may include the following fatty acid constituents; lauroyl, myristoyl, palmitoyl, stearoyl, arachidoyl, oleoyl, linoleoyl, erucoyl, or combinations of these fatty acids.

Pharmaceutical agents, such as the lipid A mimics disclosed herein or an antigen, can be internalized within or attached to the liposomes. Several different agents may be internalized or attached to the same liposome, or different agents may be associated with different liposomes, and the liposomes administered separately or together to a subject.

In some embodiments, a lipid-containing molecule (such as embodiments of the lipid A mimics disclosed herein) can be incorporated into a liposome because the lipid portion is capable of integrating into the lipid bilayer. Thus, a lipid A mimic of the invention may be presented on the "surface" of a liposome or, additionally or alternatively, may be encapsulated within a liposome while at the same time being incorporated into the lipid bilayer.

In some embodiments, one or more antigens (e.g. haptens) may be attached to polar lipids that in turn become part of the liposome particle. In this case, the lipid moiety of the liposome may act as an immunogenic carrier. In some embodiments, lipidation of an antigen may facilitate its attachment to (or incorporation into) a liposome, which in turn may improve the immune presentation of the antigen.

In further embodiments, a liposome may include lipids with a special affinity for particular target cells. For example, lactosylceramide has a specific affinity for hepatocytes (and perhaps also for liver cancer cells).

As another embodiment, the pharmaceutical or vaccine compositions encompassed herein may be a formulation comprising amphipathic compound suspended in a hydrophobic carrier (e.g. continuous oil medium), wherein the formulation is substantially free of water. Such compositions are described, for example, in WO 2009/043165, which is incorporated herein by reference.

Carrier Comprising a Continuous Phase of a Hydrophobic Substance

The pharmaceutical or vaccine compositions of the invention may comprise a pharmaceutically acceptable carrier as described herein.

In some embodiments, the carrier is a carrier that comprises a continuous phase of a hydrophobic substance, such as for example a liquid hydrophobic substance. The continuous phase may be an essentially pure hydrophobic substance or a mixture of hydrophobic substances. In addition, the carrier may be an emulsion of water in a hydrophobic substance or an emulsion of water in a mixture of hydrophobic substances, provided the hydrophobic substance constitutes the continuous phase. It is possible in some embodiments that these types of carriers may additionally function as an adjuvant.

Hydrophobic substances that are useful in the compositions described herein are those that are pharmaceutically and/or immunologically acceptable. The carrier is typically a liquid but certain hydrophobic substances that are not liquids at atmospheric temperature may be liquefied, for example by warming, and may also be useful.

Oil or water-in-oil emulsions are particularly suitable carriers for use in the pharmaceutical or vaccine compositions disclosed herein. Oils should be pharmaceutically and/or immunologically acceptable. Suitable oils include, for example, mineral oils (especially light or low viscosity mineral oil such as Drakeol® 6VR), vegetable oils (e.g., soybean oil), nut oils (e.g., peanut oil), or mixtures thereof. Thus, in an embodiment the carrier is a hydrophobic substance such as vegetable oil, nut oil or mineral oil. Animal fats and artificial hydrophobic polymeric materials, particularly those that are liquid at atmospheric temperature or that can be liquefied relatively easily, may also be used.

In some embodiments, the hydrophobic carrier may be Incomplete Freund's Adjuvant (IFA), a mineral oil-based model hydrophobic carrier.

In another embodiment, the hydrophobic carrier may be a mannide oleate in mineral oil solution, such as that commercially available as Montanide® ISA 51 (SEPPIC, France).

To enhance immunogenicity of vaccines, Immunovaccine Inc. has developed an adjuvanting vaccine platform designed to facilitate a strong and robust immune response to peptide or polynucleotide antigens. DepoVax™ (DPX) is a liposome-in-oil formulation that can be formulated with any antigen, or mixture of antigens, to induce or potentiate a cell-mediated immune response (Karkada et al., *J Immunother* 33(3):250-261, 2010) and/or a humoral immune response. DPX forms a strong depot at the site of immunization which prolongs antigen exposure to the immune system.

It has been shown that a single vaccination with peptide or polynucleotide antigens in DPX results in equivalent or better immune responses than multiple vaccinations with the same antigens in other conventional formulations, such as Montanide ISA51 VG emulsions, similar to VacciMax which was a first generation emulsion-based vaccine platform (Daftarian et al., *J Transl Med* 5: 26, 2007; Mansour et al., *J Transl Med* 5: 20, 2007). A DepoVax™ based peptide-vaccine called DPX-0907 has completed a phase I clinical trial in breast, ovarian and prostate cancer patients demonstrating safety and immunogenicity in these advanced patients (Berinstein et al., *J Transl Med* 10(1): 156, 2012).

Unlike water-in-oil emulsion based vaccines, which rely on oil entrapping water droplets containing antigen and adjuvant, DepoVax™ based formulations rely on liposomes to facilitate the incorporation of antigens and adjuvants directly into the oil, without the need for emulsification. Advantages of this approach include: (1) enhancing the solubility of hydrophilic antigens/adjuvant in oil diluents which otherwise would normally have maximum solubility in aqueous based diluents, and (2) the elimination of cumbersome emulsification procedures prior to vaccine administration.

In some embodiments, the hydrophobic carrier of the pharmaceutical or vaccine compositions disclosed herein may be Immunovaccine, Inc's liposomal-based adjuvanting system DepoVax™.

In certain embodiments, the compositions may be substantially free of water (e.g., "water-free"). It is possible that the hydrophobic carrier of these "water-free" compositions may still contain small quantities of water, provided that the water is present in the non-continuous phase of the carrier. For example, individual components of the composition may have bound water that may not be completely removed by processes such as lyophilization or evaporation and certain hydrophobic carriers may contain small amounts of water dissolved therein. Generally, compositions of the invention that are "water-free" contain, for example, less than about 10%, 9%, 8%, 7%, 6%, 5%, 4%, 3%, 2%, 1%, 0.5%, 0.1%, 0.05% or 0.01% water on a weight/weight basis of the total weight of the carrier component of the composition.

Additional Adjuvants

In some embodiments of the compositions disclosed herein, the lipid A mimic is present as the active ingredient (e.g. as an LPS/lipid A antagonist). In other compositions disclosed herein, the lipid A mimic is an additional component that is included with an active ingredient. In the latter embodiment, the lipid A mimics may act as an adjuvant. In either of these embodiments, the compositions may contain one or more (additional) adjuvants.

A large number of adjuvants have been described and are known to those skilled in the art. See, for example, Remington's Pharmaceutical Sciences (Remington's Pharmaceutical Sciences, Mack Publishing Company, Easton, Pa., USA 1985) and The United States Pharmacopoeia: The National Formulary (USP 24 NF19) published in 1999.

Exemplary adjuvants include, without limitation, alum, other compounds of aluminum, *Bacillus* of Calmette and Guerin (BCG), TiterMax™, Ribi™, Freund's Complete Adjuvant (FCA), CpG-containing oligodeoxynucleotides (CpG ODN), lipopeptides and polyI:C polynucleotides. An exemplary CpG ODN is 5'-TCCAT<u>GACGTT</u>CCT<u>GACGTT</u>-3' (SEQ ID NO: 24). The skilled person can readily select other appropriate CpG ODNs on the basis of the target species and efficacy. An exemplary lipopeptide includes, without limitation, Pam3Cys-SKKK (EMC Microcollections, Germany) or variants, homologs and analogs thereof. The Pam2 family of lipopeptides has been shown to be an effective alternative to the Pam3 family of lipopeptides.

In some embodiments, the pharmaceutical or vaccine compositions may comprise a polyI:C polynucleotide as an adjuvant, such as for example and without limitation, a 26 mer deoxy inosine/cytosine synthetic polynucleotide.

As used herein, a "polyI:C" or "polyI:C polynucleotide" is a double-stranded polynucleotide molecule (RNA or DNA or a combination of DNA and RNA), each strand of which contains at least 6 contiguous inosinic or cytidylic acid residues, or at least 6 contiguous residues selected from inosinic acid and cytidylic acid in any order (e.g. IICIIC, ICICIC or IIICCC), and which is capable of inducing or enhancing the production of at least one inflammatory cytokine, such as interferon, in a mammalian subject. PolyI:C polynucleotides will typically have a length of about 8, 10, 12, 14, 16, 18, 20, 22, 24, 25, 28, 30, 35, 40, 45, 50, 55, 60, 65, 70, 75, 80, 85, 90, 95, 100, 150, 200, 250, 300, 500, 1000 or more residues. The upper limit is not believed to be essential. PolyI:C polynucleotides will often have a minimum length of about 6, 8, 10, 12, 14, 16, 18, 20, 22, 24, 26, 28, or 30 nucleotides and a maximum length of about 1000, 500, 300, 200, 100, 90, 80, 70, 60, 50, 45 or 40 nucleotides.

Each strand of a polyI:C polynucleotide may be a homopolymer of inosinic or cytidylic acid residues, or each strand may be a heteropolymer containing both inosinic and cytidylic acid residues. In either case, the polymer may be interrupted by one or more non-inosinic or non-cytidylic acid residues (e.g. uridine), provided there is at least one contiguous region of 6 I, 6 C or 6 I/C residues as described above. Typically, each strand of a polyI:C polynucleotide will contain no more than 1 non-I/C residue per 6 I/C residues, more particularly no more than 1 non-I/C residue per every 8, 10, 12, 14, 16, 18, 20, 22, 24, 26, 28 or 30 I/C residues.

The inosinic acid or cytidylic acid (or other) residues in the polyI:C polynucleotide may be derivatized or modified as is known in the art, provided the ability of the polyI:C polynucleotide to promote the production of an inflammatory cytokine, such as interferon, is retained. Non-limiting examples of derivatives or modifications include e.g. azido modifications, fluoro modifications, or the use of thioester (or similar) linkages instead of natural phosphodiester linkages to enhance stability in vivo. The polyI:C polynucleotide may also be modified to e.g. enhance its resistance to degradation in vivo by e.g. complexing the molecule with positively charged poly-lysine and carboxymethylcellulose, or with a positively charged synthetic peptide.

If present, the polyI:C polynucleotide will typically be included in the compositions in an amount from about 0.001 mg to 1 mg/unit dose of the composition. In certain embodiments, the amount of polyI:C polynucleotide will be about 0.04 mg/mL of the composition.

Other suitable adjuvants of the compositions disclosed herein are those that activate or increase the activity of TLR2. As used herein, an adjuvant which "activates" or "increases the activity" of a TLR2 includes any adjuvant, in some embodiments a lipid-based adjuvant, which acts as a TLR2 agonist. Further, activating or increasing the activity of TLR2 encompasses its activation in any monomeric, homodimeric or heterodimeric form, and particularly includes the activation of TLR2 as a heterodimer with TLR1 or TLR6 (i.e. TLR1/2 or TLR2/6). Exemplary embodiments of an adjuvant that activates or increases the activity of TLR2 include lipid-based adjuvants, such as those described in WO 2013/049941.

Further examples of adjuvants that may be used include, without limitation, chemokines, colony stimulating factors, cytokines, 1018 ISS, aluminum salts, Amplivax, AS04, AS15, ABM2, Adjumer, Algammulin, AS01B, AS02 (SBASA), ASO2A, BCG, Calcitriol, Chitosan, Cholera toxin, CP-870,893, CpG, polyI:C, CyaA, DETOX (Ribi Immunochemicals), Dimethyldioctadecylammonium bromide (DDA), Dibutyl phthalate (DBP), dSLIM, Gamma inulin, GM-CSF, GMDP, Glycerol, IC30, IC31, Imiquimod, ImuFact IMP321, IS Patch, ISCOM, ISCOMATRIX, Juvlmmune, LipoVac, LPS, lipid core protein, MF59, monophosphoryl lipid A and analogs or mimics thereof, Montanide® IMS1312, Montanide® based adjuvants (e.g. Montanide ISA-51, -50 and -70), OK-432, OM-174, OM-197-MP-EC, ONTAK, PepTel vector system, other palmitoyl based molecules, PLG microparticles, resiquimod, squalene, SLR172, YF-17 DBCG, QS21, QuilA, P1005, Poloxamer, Saponin, synthetic polynucleotides, Zymosan, pertussis toxin.

Accordingly, the compositions herein may comprise one or more (additional) pharmaceutically acceptable adjuvants.

In some embodiments, at least one of the antigens may be coupled to at least one of the adjuvants.

The amount of adjuvant used depends on the amount of antigen and on the type of adjuvant. One skilled in the art can readily determine the amount of adjuvant needed in a particular application by empirical testing.

Methods of Preparing the Pharmaceutical or Vaccine Compositions

Generally, methods of preparing pharmaceutical compositions are well known in the art, and any of these methods may be employed in order to prepare the compositions described herein.

In some embodiments, the vaccine composition is one that comprises at least one antigen, liposomes, at least one lipid A mimic, and a carrier comprising a continuous phase of a hydrophobic substance. Exemplary methods for preparing these compositions are described further herein, without limitation.

Methods for making liposomes are well known in the art. See e.g. Gregoriadis (1990) and Frezard (1999) both cited previously. Any suitable method for making liposomes may be used in the practice of the invention, or liposomes may be obtained from a commercial source. Liposomes are typically prepared by hydrating the liposome components that will form the lipid bilayer (e.g. phospholipids and cholesterol) with an aqueous solution, which may be pure water or a solution of one or more components dissolved in water, e.g. phosphate-buffered saline (PBS), phosphate-free saline, or any other physiologically compatible aqueous solution.

In an embodiment, a liposome component or mixture of liposome components, such as a phospholipid (e.g. Phospholipon® 90G) or DOPC and cholesterol, may be solubilized in an organic solvent, such as a mixture of chloroform and methanol or tert-butanol, followed by filtering (e.g. a PTFE 0.2 μm filter) and drying, e.g. by rotary evaporation, to remove the solvents.

Hydration of the resulting lipid mixture may be effected by e.g. injecting the lipid mixture into an aqueous solution or sonicating the lipid mixture and an aqueous solution. During formation of liposomes, the liposome components form single bilayers (unilamellar) or multiple bilayers (multilamellar) surrounding a volume of the aqueous solution with which the liposome components are hydrated.

In some embodiments, the liposomes are then dehydrated, such as by freeze-drying or lyophilization.

The liposomes are combined with an appropriate carrier, such as a carrier comprising a continuous hydrophobic phase. This can be done in a variety of ways.

If the carrier is composed solely of a hydrophobic substance or a mixture of hydrophobic substances (e.g. use of a 100% mineral oil carrier), the liposomes may simply be mixed with the hydrophobic substance, or if there are multiple hydrophobic substances, mixed with any one or a combination of them.

If instead the carrier comprising a continuous phase of a hydrophobic substance contains a discontinuous aqueous phase, the carrier will typically take the form of an emulsion of the aqueous phase in the hydrophobic phase, such as a water-in-oil emulsion. Such compositions may contain an emulsifier to stabilize the emulsion and to promote an even distribution of the liposomes. In this regard, emulsifiers may be useful even if a water-free carrier is used, for the purpose of promoting an even distribution of the liposomes in the carrier. Typical emulsifiers include mannide oleate (Arlacel™ A), lecithin (e.g. S100 lecithin), a phospholipid, Tween™ 80, and Spans™ 20, 80, 83 and 85. Typically, the volume ratio (v/v) of hydrophobic substance to emulsifier is in the range of about 5:1 to about 15:1. In an embodiment, the volume ratio (v/v) of hydrophobic substance to emulsifier is about 10:1.

The liposomes may be added to the finished emulsion, or they may be present in either the aqueous phase or the hydrophobic phase prior to emulsification.

The antigen(s) as described herein may be introduced at various different stages of the formulation process. More than one type of antigen may be incorporated into the composition. As used in this section, the term "antigen" is used generally to describe how any antigen may be formulated in the vaccine compositions of the invention. The term "antigen" encompasses both the singular form "antigen" and the plural "antigens". It is not necessary that all antigens be introduced into the vaccine composition in the same way.

In some embodiments, the antigen is present in the aqueous solution used to hydrate the components that are used to form the lipid bilayers of the liposomes (e.g. phospholipid(s) and cholesterol). In this case, the antigen will be encapsulated in the liposome, present in its aqueous interior. If the resulting liposomes are not washed or dried, such that there is residual aqueous solution present that is ultimately mixed with the carrier comprising a continuous phase of a hydrophobic substance, it is possible that additional antigen may be present outside the liposomes in the final product. In a related technique, the antigen may be mixed with the components used to form the lipid bilayers of the liposomes, prior to hydration with the aqueous solution. The antigen may also be added to pre-formed liposomes, in which case the antigen may be actively loaded into the liposomes, or bound to the surface of the liposomes or the antigen may remain external to the liposomes. In such embodiments, prior to the addition of antigen, the pre-formed liposomes may be empty liposomes (e.g. not containing encapsulated antigen or lipid A mimic) or the pre-formed liposomes may contain lipid A mimic incorporated into or associated with the liposomes. These steps may occur prior to mixing with the carrier comprising a continuous phase of a hydrophobic substance.

In an alternative approach, the antigen may instead be mixed with the carrier comprising a continuous phase of a hydrophobic substance, before, during, or after the carrier is combined with the liposomes. If the carrier is an emulsion, the antigen may be mixed with either or both of the aqueous phase or hydrophobic phase prior to emulsification. Alternatively, the antigen may be mixed with the carrier after emulsification.

The technique of combining the antigen with the carrier may be used together with encapsulation of the antigen in the liposomes as described above, such that antigen is present both within the liposomes and in the carrier comprising a continuous phase of a hydrophobic substance.

The above-described procedures for introducing the antigen into the composition apply also to the lipid A mimic and/or the T-helper epitope (if a T-helper epitope is included). That is, the lipid A mimic and T-helper epitope (if present) may be introduced into e.g. one or more of: (1) the aqueous solution used to hydrate the components that are used to form the lipid bilayers of the liposomes; (2) the aqueous solution after formation of the lipid bilayers of the liposomes; (3) the components used to form the lipid bilayers of the liposomes; or (4) the carrier comprising a continuous phase of a hydrophobic substance, before, during, or after the carrier is combined with the liposomes. If the carrier is an emulsion, the lipid A mimic and T-helper epitope (if present) may be mixed with either or both of the aqueous phase or hydrophobic phase before, during or after emulsification.

In an additional embodiment, the lipid chain of the lipid A mimic may be incorporated into the lipid bilayer when the liposomes form.

The technique of combining the lipid A mimic and T-helper epitope (if present) with the carrier may be used together with encapsulation of these components in the liposomes, or with addition of these components to the liposomes, such that lipid A mimic and T-helper epitope are present inside the liposomes and/or outside the liposomes in the carrier comprising a continuous phase of a hydrophobic substance.

The lipid A mimic and T-helper epitope (if present) can be incorporated in the composition together with the antigen at the same processing step, or separately, at a different processing step. For instance, the antigen, lipid A mimic and T-helper epitope may all be present in the aqueous solution used to hydrate the lipid bilayer-forming liposome components, such that all three components become encapsulated in the liposomes. Alternatively, the antigen and the T-helper epitope may be encapsulated in the liposomes, and the lipid A mimic mixed with the carrier comprising a continuous phase of a hydrophobic substance. In a further embodiment, the T-helper epitope and/or lipid A mimic may be incorporated into the composition after the antigen encapsulation step by passing the liposome-antigen preparation through a manual mini-extruder and then mixing the obtained liposome-antigen preparation with the lipid A mimic in, for example, phosphate buffer. The T-helper epitope and/or lipid A mimic may also be incorporated into the composition, either alone or together with antigen, after the liposomes have been formed, such that the T-helper epitope and lipid A mimic may be associated or remain external to the liposomes. The T-helper epitope and/or lipid A mimic may also be incorporated into or associated with liposomes prior to addition of antigen, with the antigen remaining outside the pre-formed liposomes or loaded into/associated with the liposomes by further processing. In such embodiments, the resulting preparation may be lyophilized and then reconstituted in the carrier comprising a continuous phase of a hydrophobic substance. It will be appreciated that many such combinations are possible.

In a particular embodiment, the vaccine compositions described herein may be prepared by solubilizing a 10:1 mixture of dioleoyl phosphatidylcholine (DOPC) and cholesterol in tert-butanol. The antigen and lipid A mimic are each independently solubilized in separate solutions of dimethyl sulfoxide or water. The antigen is then added to the DOPC/cholesterol/tert-butanol mixture. The lipid A mimic is also then added to the DOPC/cholesterol/tert-butanol mixture. A dry homogenous mixture of the vaccine constituents is prepared by removing the solvents and water by lyophilization. The dry mixture is then suspended in a hydrophobic carrier, such as for example, and without limitation, Incomplete Freud's Adjuvant (e.g. a mineral oil-based model hydrophobic carrier).

If the composition contains one or more additional adjuvants, such additional adjuvants can be incorporated in the composition in similar fashion as described above for the antigen or by combining several of such methods as may be suitable for the additional adjuvant(s).

Stabilizers such as sugars, anti-oxidants, or preservatives that maintain the biological activity or improve chemical stability to prolong the shelf life of the antigen, lipid A mimic, liposomes or continuous hydrophobic carrier, may be added to such compositions.

In some embodiments, an antigen/lipid A mimic mixture may be used, in which case the antigen and lipid A mimic are incorporated into the composition at the same time. An "antigen/lipid A mimic mixture" refers to an embodiment in which the antigen and lipid A mimic are in the same diluent at least prior to incorporation into the composition. The antigen and lipid A mimic in an antigen/lipid A mimic mixture may, but need not necessarily be chemically linked, such as by covalent bonding.

In some embodiments, the carrier comprising a continuous phase of a hydrophobic substance may itself have adjuvanting-activity. Incomplete Freund's adjuvant and Montanide® ISA 51 VG, are examples of a hydrophobic carrier with adjuvanting effect.

Molecular Signalling

The molecular target and mechanisms of action for LPS/lipid A in regard to their immunomodulatory activity have been identified, and involve a group of proteins known as Toll-like receptors (TLRs). LPS/lipid A is recognized by Toll-like receptor 4 (TLR4), a member of the TLR family, which is associated with another protein MD-2. TLR4 is expressed as a complex with the obligate accessory protein MD-2 (Akira, S. M. Adv. Exp. Med. Biol., 667: 59-68, 2010). The crystal structure of TLR4/MD-2 with the bound ligand LPS has been determined (Park et al., Nature, 458: 1191-1196, 2009), which provides direct evidence for the molecular basis of recognition of LPS/lipid A by TLR4/MD-2.

TLR4 plays an important role in the innate immunity and the development of adaptive immune responses. The activation of TLR4 by Gram-negative bacterial LPS has been extensively studied and molecular mechanisms post-activation delineated (Akira, S. M. *Adv. Exp. Med. Biol.,* 667: 59-68, 2010). The ability to regulate the induction of an adaptive immune response has made TLR4 an attractive target in terms of developing vaccine adjuvants (Jiang et al., *Curr. Med. Chem.,* 10: 1423-1439, 2003). Indeed, it is well recognized that TLR4 agonists are an important class of immunostimulatory vaccine adjuvants.

In some embodiments, the lipid A mimics of the invention may signal through TLR4. As shown in Example 13, exemplary lipid A mimics JL-265 and JL-266 provided a strong increased expression of both CD40 and CD86 in dendritic cells of wild-type mice (C3H/HeOuJ) (see FIGS. 7a and 7b; clear bars). However, in TLR4 mutant mice (C3H/HeJ), the induction of CD40 and CD86 in dendritic cells was significantly reduced (see FIG. 7a and 7b; shaded bars). This finding is consistent with that observed for LPS, which is also shown to signal through TLR4 in Example 13. A control polyI:C adjuvant, which is known not to signal through TLR4, provided a comparable stimulation of CD40 and CD86 in dendritic cells of both wild-type and TLR mutant mice. Thus, the data in Example 13 demonstrates that embodiments of lipid A mimics disclosed herein are capable of signalling through TLR4.

Figure 7:
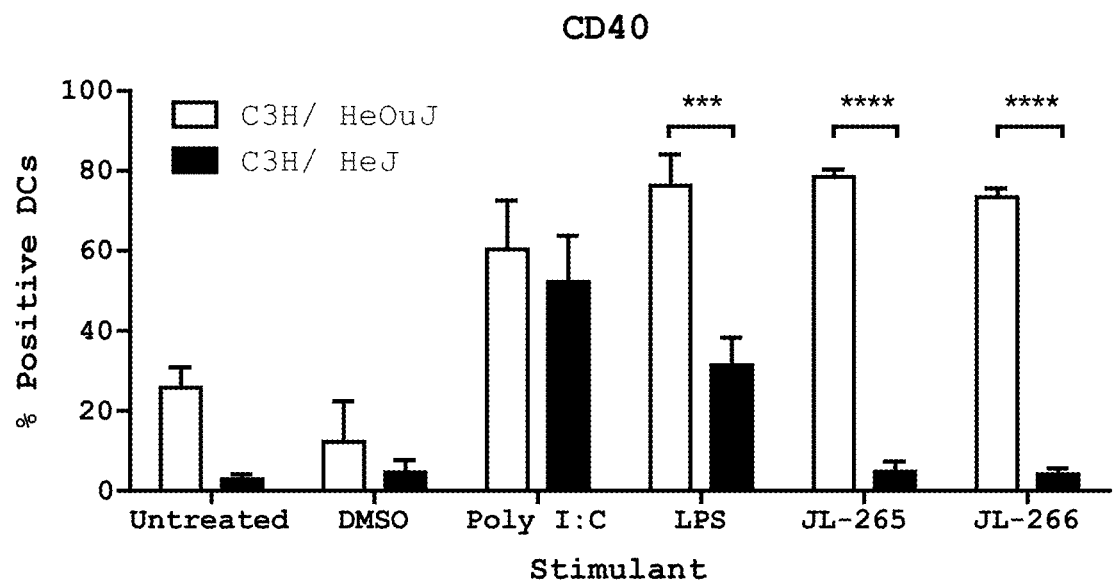
FIG. 7 illustrates the increased expression of CD40 and CD86 induced by exemplary lipid A mimics JL-265 and JL-266 in dendritic cells of wild-type mice as compared to dendritic cells of TLR4 mutant mice. Dendritic cells were isolated from bone marrow of naïve C3H/HeOuJ (Wild-type) or C3H/HeJ (TLR4 mutant) mice (n=3). Dendritic cells were stimulated overnight with DMSO vehicle control or 20 micrograms/millilitre of poly I:C, LPS, JL-265 or JL-266. Next day, cells were stained with fluorochrome-conjugated antibodies specific for CD11c (dendritic cell marker) and CD40 or CD86 (markers of dendritic cell activation). Results are shown as percent CD40 positive of CD11c (Figure A) or percent CD86 positive of CD11c positive (Figure B). Statistics calculated by 2-way AONVA.
Figure 7:
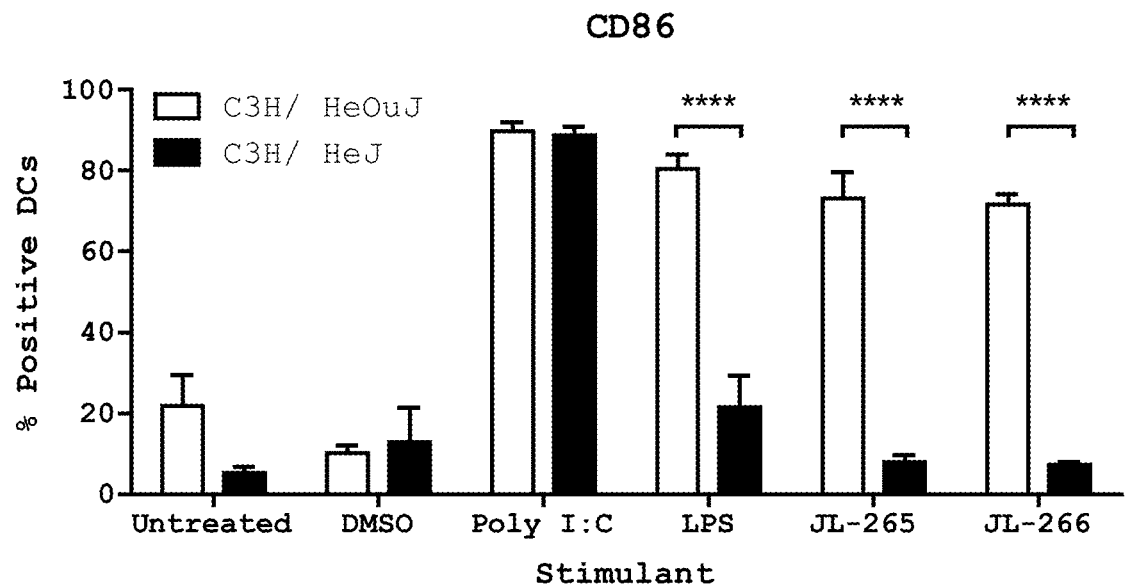

Further, as shown in FIG. 7, in the TLR mutant mice the exemplary lipid A mimics JL-265 and JL-266 provide a slightly lower induction of CD40 and CD86 than LPS, whereas in the wild-type mice both lipid A mimics perform the same as LPS. This indicates that LPS can signal through other receptors besides TLR4, while the lipid A mimics may only signal through TLR4. A potential benefit of this is that, as compared to LPS, the lipid A mimics of the invention may be less likely to induce side effects caused by off-target stimulation of other receptors.

In view of the compounds disclosed herein being lipid A mimics, and further considering their demonstrated ability to signal through TLR4, the lipid A mimics of the invention may be useful as adjuvants or other immunomodulating agents. As used in this context, the term "immunomodulatory agent" refers to a compound that is capable of inducing (e.g. eliciting) or potentiating the activity of the immune response to a biological entity or is capable of decreasing an immune response.

As used herein, "inducing or potentiating" an immune response encompasses, for example, instances where the immune response is initiated (e.g. elicited), stimulated, enhanced, elevated, improved and/or strengthened to the benefit of the host relative to any prior immune response status (or lack thereof) before the administration of a composition of the invention. As used herein, "decreasing" an immune response encompasses, for example, instances where the immune response is reduced, diminished, weakened, negated and/or terminated to the benefit of the host relative to any prior immune response status before the administration of a composition of the invention i) Lipid A Mimics as Potential Bacterial Endotoxin Antagonists In one embodiment, a lipid A mimic disclosed herein may act as an antagonist to natural lipid A or LPS, and may be useful in the treatment or prevention of a LPS/lipid A-mediated disease or disorder characterized by overactivation of a subject's immune system, such as Gram-negative septicaemia or septic shock. In these embodiments, the lipid A mimics may themselves be used as an active ingredient in the pharmaceutical compositions described herein.

For instance, in some embodiments the lipid A mimics disclosed herein may have LPS/lipid A antagonist activity. By "antagonist activity", it is meant that the lipid A mimics may be capable of binding to the same biological receptor as LPS or lipid A (e.g. TLR4) and therefore may be capable of preventing or diminishing the activity of the natural LPS or lipid A. In such embodiments, the lipid A mimics may be useful in the treatment or prevention of LPS/lipid A-mediated disease or disorder.

Upon Gram-negative bacterial infection in humans, bacterial endotoxin, such as LPS, are released into the blood stream. Acute inflammatory responses to LPS or its active principle lipid A result in the release of cytokines and other cellular mediators, including tumor necrosis factor-α (TNF-α), interleukin-1 (IL-1), IL-6 and leukotrienes from monocytes and macrophages. At extreme levels, these cytokines and cellular mediators are known to trigger many pathophysiological events including fever, shock, hypotension, and organ failure (see e.g. Bone, R. C., *Clin. Microbiol. Rev.,* 6: 57-68, 1993). These events are generally termed as septic syndrome. Sepsis is deadly and kills tens of thousands of people annually in the US alone.

One strategy to control LPS-mediated disorders is to prevent LPS/lipid A binding to receptors with inactive competitors (antagonists) of LPS/lipid A. The lipid A mimics disclosed herein, and particularly those that maintain their structural similarity to the natural lipid A molecules, may bind to the LPS/lipid A-binding receptor, TLR4, but without triggering the uncontrolled release of inflammatory cytokines by the immune system. As LPS/lipid A-antagonists, such lipid A mimics might inhibit LPS/lipid A-induced production of cytokines and thus potentially confer benefits in treating or preventing LPS/lipid A-mediated diseases or disorders resulting from Gram-negative bacterial infections. Such diseases and disorders may include, without limitation, fever, generalized inflammation, disseminated intravascular coagulation, hypotension, acute renal failures, acute respiratory distress syndrome, hepatocellular destruction, and cardiac failure.

In some embodiments, such lipid A mimics may be administered in conjunction with common antibiotics to relieve the burden to the host caused by the infections.

Another potential application of lipid A mimics disclosed herein may be to suppress LPS-mediated virus production. LPS potently stimulates the production of viruses which reside in monocytes or macrophages (Pomerantz et al., *J. Exp. Med.*, 172(1): 253-261, 1990). In some embodiments in which the lipid A mimics disclosed herein function as LPS-antagonists, it is contemplated that they may also be capable of inhibiting an LPS-mediated increase in virus production. Such viruses may include, without limitation, human immunodeficiency viruses (HIV), cytomegaloviruses, herpes simplex viruses, and influenza viruses. Thus, the lipid A mimics may provide useful therapeutics for the treatment or prevention of LPS-mediated exacerbation of latent or active viral infections.

ii) Lipid A Mimics as Potential Immunostimulatory Agents

In another embodiment, a lipid A mimic disclosed herein may activate or stimulate the immune system of a subject, thereby having potential for use as an immunotherapeutic agent in the treatment or prevention of a wide range of diseases, such as for example and without limitation, infections and cancers. In these embodiments, the lipid A mimics disclosed herein may be used as a primary therapeutic or may be included in a therapeutic or prophylactic vaccine composition as e.g. an adjuvant.

In some embodiments, the lipid A mimics disclosed herein may function as an immunostimulatory agent. By "immunostimulatory agent", it is meant that the lipid A mimics may have the potential to induce or potentiate an immune response (e.g. act as adjuvant), such as an immune response to an antigen. The lipid A mimics may, for example, exhibit their effect by enhancing the humoral immune response, such as enhancing the generation of antibodies; stimulating the production of cytokines; and/or stimulating a cell-mediated immune response including a cytotoxic T-lymphocyte response. Also, in such embodiments, the lipid A mimics may be usefully administered to a subject with other therapeutic agents for the treatment of targeted diseases in combined therapy to potentially achieve better efficacy. For example, and without limitation, the lipid A mimics may be used in combination with antibiotics, anti-viral agents, anti-inflammatory agents, and chemotherapy agents.

A humoral immune response, as opposed to cell-mediated immunity, is mediated by secreted antibodies which are produced in the cells of the B lymphocyte lineage (B cells). Such secreted antibodies bind to antigens, such as for example those on the surfaces of foreign substances, pathogens (e.g. viruses, bacteria, etc.) and/or cancer cells, and flag them for destruction.

As used herein, "humoral immune response" refers to antibody production and may also include, in addition or alternatively, the accessory processes that accompany it, such as for example the generation and/or activation of T-helper 2 (Th2) or T-helper 17 (Th17) cells, cytokine production, isotype switching, affinity maturation and memory cell activation. "Humoral immune response" may also include the effector functions of an antibody, such as for example toxin neutralization, classical complement activation, and promotion of phagocytosis and pathogen elimination. The humoral immune response is often aided by CD4+ Th2 cells and therefore the activation or generation of this cell type may also be indicative of a humoral immune response. The term "humoral immune response" is used interchangeably herein with "antibody response" or "antibody immune response".

An "antibody" is a protein comprising one or more polypeptides substantially or partially encoded by immunoglobulin genes or fragments of immunoglobulin genes. The recognized immunoglobulin genes include the κ, λ, α, γ, δ, ε and μ constant region genes, as well as myriad immunoglobulin variable region genes. Light chains are classified as either κ or λ. Heavy chains are classified as γ, μ, α, δ, or ε, which in turn define the immunoglobulin classes, IgG, IgM, IgA, IgD and IgE, respectively. A typical immunoglobulin (antibody) structural unit comprises a protein containing four polypeptides. Each antibody structural unit is composed of two identical pairs of polypeptide chains, each having one "light" and one "heavy" chain. The N-terminus of each chain defines a variable region primarily responsible for antigen recognition. Antibody structural units (e.g. of the IgA and IgM classes) may also assemble into oligomeric forms with each other and additional polypeptide chains, for example as IgM pentamers in association with the J-chain polypeptide.

Antibodies are the antigen-specific glycoprotein products of a subset of white blood cells called B lymphocytes (B cells). Engagement of antigen with antibody expressed on the surface of B cells can induce an antibody response comprising stimulation of B cells to become activated, to undergo mitosis and to terminally differentiate into plasma cells, which are specialized for synthesis and secretion of antigen-specific antibody.

B cells are the sole producers of antibodies during an immune response and are thus a key element to effective humoral immunity. In addition to producing large amounts of antibodies, B cells also act as antigen-presenting cells and can present antigen to T cells, such as T helper CD4 or cytotoxic CD8+ T cells, thus propagating the immune response. B cells, as well as T cells, are part of the adaptive immune response. During an active immune response, induced for example by either vaccination or natural infection, antigen-specific B cells are activated and clonally expand. During expansion, B cells evolve to have higher affinity for the epitope. Proliferation of B cells can be induced indirectly by activated T-helper cells, and also directly through stimulation of receptors, such as the TLRs.

Antigen presenting cells, such as dendritic cells and B cells, are drawn to vaccination sites and can interact with antigens and adjuvants contained in a vaccine composition. Typically, the adjuvant stimulates the cells to become activated and the antigen provides the blueprint for the target. Different types of adjuvants may provide different stimulation signals to cells. For example, poly I:C (a TLR3 agonist) can activate dendritic cells, but not B cells. Adjuvants such as Pam3Cys, Pam2Cys and FSL-1 are especially adept at activating and initiating proliferation of B cells, which is expected to facilitate the production of an antibody response (Moyle et al., *Curr Med Chem*, 2008; So., *J Immunol*, 2012).

A humoral immune response is one of the common mechanisms for effective infectious disease vaccines (e.g. to protect against viral or bacterial invaders). However, a humoral immune response can also be useful for combating cancer. Whereas a cancer vaccine is typically designed to produce a cell-mediated immune response that can recognize and destroy cancer cells, B cell mediated responses may target cancer cells through other mechanisms which may in some instances cooperate with a cytotoxic T cell for maximum benefit. Examples of B cell mediated (e.g. humoral immune response mediated) anti-tumor responses include, without limitation: 1) Antibodies produced by B cells that bind to surface antigens found on tumor cells or other cells that influence tumorigenesis. Such antibodies can, for example. induce killing of target cells through antibody-dependant cell-mediated cytotoxicity (ADCC) or complement fixation, potentially resulting in the release of additional antigens that can be recognized by the immune system; 2) Antibodies that bind to receptors on tumor cells to block their stimulation and in effect neutralize their effects; 3) Antibodies that bind to factors released by or associated with a tumor or tumor-associated cells to modulate a signaling or cellular pathway that supports cancer; and 4) Antibodies that bind to intracellular targets and mediate anti-tumor activity through a currently unknown mechanism.

One method of evaluating an antibody response is to measure the titers of antibodies reactive with a particular antigen. This may be performed using a variety of methods known in the art such as enzyme-linked immunosorbent assay (ELISA) of antibody-containing substances obtained from animals. For example, the titers of serum antibodies which bind to a particular antigen may be determined in a subject both before and after exposure to the antigen. A statistically significant increase in the titer of antigen-specific antibodies following exposure to the antigen would indicate the subject had mounted an antibody response to the antigen.

Without limitation, other assays that may be used to detect the presence of an antigen-specific antibody include immunological assays (e.g. radioimmunoassay (RIA)), immuno-precipitation assays, and protein blot (e.g. Western blot) assays; and neutralization assays (e.g., neutralization of viral infectivity in an in vitro or in vivo assay).

As used herein, the terms "cell-mediated immune response" or "cellular immunity" (used interchangeably herein) refer to an immune response characterized by the activation of macrophages and natural killer cells, the production of antigen-specific cytotoxic T lymphocytes and/or the release of various cytokines in response to an antigen. Cytotoxic T lymphocytes are a sub-group of T lymphocytes (a type of white blood cell) which are capable of inducing the death of infected somatic or tumor cells; they kill cells that are infected with viruses (or other pathogens), or that are otherwise damaged or dysfunctional.

Most cytotoxic T cells express T cell receptors that can recognise a specific peptide antigen bound to Class I MHC molecules. Typically, cytotoxic T cells also express CD8 (i.e. CD8+ T cells), which is attracted to portions of the Class I MHC molecule. This affinity keeps the cytotoxic T cell and the target cell bound closely together during antigen-specific activation.

Cellular immunity protects the body by, for example, activating antigen-specific cytotoxic T-lymphocytes (e.g. antigen-specific CD8+ T cells) that are able to lyse body cells displaying epitopes of foreign antigen on their surface, such as virus-infected cells, cells with intracellular bacteria, and cancer cells displaying tumor antigens; activating macrophages and natural killer cells, enabling them to destroy intracellular pathogens; and stimulating cells to secrete a variety of cytokines that influence the function of other cells involved in adaptive immune responses and innate immune responses.

Cellular immunity is an important component of the adaptive immune response and following recognition of antigen by cells through their interaction with antigen-presenting cells such as dendritic cells, B lymphocytes and to a lesser extent, macrophages, protects the body by various mechanisms such as:

1. activating antigen-specific cytotoxic T-lymphocytes that are able to induce apoptosis in body cells displaying epitopes of foreign antigen on their surface, such as virus-infected cells, cells with intracellular bacteria, and cancer cells displaying tumor antigens;

2. activating macrophages and natural killer cells, enabling them to destroy intracellular pathogens; and 3. stimulating cells to secrete a variety of cytokines that influence the function of other cells involved in adaptive immune responses and innate immune responses.

Cell-mediated immunity is most effective in removing virus-infected cells, but also participates in defending against fungi, protozoans, cancers, and intracellular bacteria. It also plays a major role in transplant rejection.

Since cell-mediated immunity involves the participation of various cell types and is mediated by different mechanisms, several methods could be used to demonstrate the induction of immunity following vaccination. These could be broadly classified into detection of: i) specific antigen presenting cells; ii) specific effector cells and their functions and iii) release of soluble mediators such as cytokines.

i) Antigen presenting cells: Dendritic cells and B cells (and to a lesser extent macrophages) are equipped with special immunostimulatory receptors that allow for enhanced activation of T cells, and are termed professional antigen presenting cells (APC). These immunostimulatory molecules (also called co-stimulatory molecules) are up-regulated on these cells following infection or vaccination, during the process of antigen presentation to effector cells such as CD4 and CD8 cytotoxic T cells. Such co-stimulatory molecules (such as CD40, CD80, CD86, MHC class I or MHC class II) can be detected, for example, by using flow cytometry with fluorochrome-conjugated antibodies directed against these molecules along with antibodies that specifically identify APC (such as CD11c for dendritic cells).

ii) Cytotoxic T cells: (also known as Tc, killer T cell, or cytotoxic T-lymphocyte (CTL)) are a sub-group of T cells which induce the death of cells that are infected with viruses (and other pathogens), or expressing tumor antigens. These CTLs directly attack other cells carrying certain foreign or abnormal molecules on their surface. The ability of such cellular cytotoxicity can be detected using in vitro cytolytic assays (chromium release assay). Thus, induction of adaptive cellular immunity can be demonstrated by the presence of such cytotoxic T cells, wherein, when antigen loaded target cells are lysed by specific CTLs that are generated in vivo following vaccination or infection.

Naive cytotoxic T cells are activated when their T cell receptor (TCR) strongly interacts with a peptide-bound MHC class I molecule. This affinity depends on the type and orientation of the antigen/MHC complex, and is what keeps the CTL and infected cell bound together. Once activated the CTL undergoes a process called clonal expansion in which it gains functionality, and divides rapidly, to produce an army of "armed"-effector cells. Activated CTL will then travel throughout the body in search of cells bearing that unique MHC Class I+peptide. This could be used to identify such CTLs in vitro by using peptide-MHC Class I tetramers in flow cytometric assays.

When exposed to these infected or dysfunctional somatic cells, effector CTL release perforin and granulysin: cytotoxins which form pores in the target cell's plasma membrane, allowing ions and water to flow into the infected cell, and causing it to burst or lyse. CTL release granzyme, a serine protease that enters cells via pores to induce apoptosis (cell death). Release of these molecules from CTL can be used as a measure of successful induction of cell-mediated immune response following vaccination. This can be done by enzyme linked immunosorbant assay (ELISA) or enzyme linked immunospot assay (ELISPOT) where CTLs can be quantitatively measured. Since CTLs are also capable of producing important cytokines such as IFN-γ, quantitative measurement of IFN-γ-producing CD8 cells can be achieved by ELISPOT and by flowcytometric measurement of intracellular IFN-γ in these cells.

CD4+ "helper" T cells: CD4+ lymphocytes, or helper T cells, are immune response mediators, and play an important role in establishing and maximizing the capabilities of the adaptive immune response. These cells have no cytotoxic or phagocytic activity; and cannot kill infected cells or clear pathogens, but, in essence "manage" the immune response, by directing other cells to perform these tasks. Two types of effector CD4+ T helper cell responses can be induced by a professional APC, designated Th1 and Th2, each designed to eliminate different types of pathogens.

Helper T cells express T cell receptors (TCR) that recognize antigen bound to Class II MHC molecules. The activation of a naive helper T cell causes it to release cytokines, which influences the activity of many cell types, including the APC that activated it. Helper T cells require a much milder activation stimulus than cytotoxic T cells. Helper T cells can provide extra signals that "help" activate cytotoxic cells. Two types of effector CD4+ T helper cell responses can be induced by a professional APC, designated Th1 and Th2, each designed to eliminate different types of pathogens. The two Th cell populations differ in the pattern of the effector proteins (cytokines) produced. In general, Th1 cells assist the cell-mediated immune response by activation of macrophages and cytotoxic T cells; whereas Th2 cells promote the humoral immune response by stimulation of B cells for conversion into plasma cells and by formation of antibodies. For example, a response regulated by Th1 cells may induce IgG2a and IgG2b in mouse (IgGI and IgG3 in humans) and favor a cell mediated immune response to an antigen. If the IgG response to an antigen is regulated by Th2 type cells, it may predominantly enhance the production of IgGI in mouse (IgG2 in humans). The measure of cytokines associated with Th1 or Th2 responses will give a measure of successful vaccination. This can be achieved by specific ELISA designed for Th1-cytokines such as IFN-γ, IL-2, IL-12, TNF-α and others, or Th2-cytokines such as IL-4, IL-5, IL10 among others.

iii) Measurement of cytokines: released from regional lymph nodes gives a good indication of successful immunization. As a result of antigen presentation and maturation of APC and immune effector cells such as CD4 and CD8 T cells, several cytokines are released by lymph node cells. By culturing these LNC in vitro in the presence of antigen, antigen-specific immune response can be detected by measuring release if certain important cytokines such as IFN-γ, IL-2, IL-12, TNF-α and GM-CSF. This could be done by ELISA using culture supernatants and recombinant cytokines as standards.

Successful immunization may be determined in a number of ways known to the skilled person including, but not limited to, hemagglutination inhibition (HAIJ) and serum neutralization inhibition assays to detect functional antibodies; challenge studies, in which vaccinated subjects are challenged with the associated pathogen to determine the efficacy of the vaccination; and the use of fluorescence activated cell sorting (FACS) to determine the population of cells that express a specific cell surface marker, e.g. in the identification of activated or memory lymphocytes. A skilled person may also determine if immunization with a composition of the invention elicited an antibody and/or cell mediated immune response using other known methods. See, for example, Current Protocols in Immunology Coligan et al., ed. (Wiley Interscience, 2007).

Pharmaceutical Applications

The pharmaceutical and/or vaccine compositions of the invention, which include a lipid A mimic as disclosed herein, may be capable of protecting a subject against a disease, disorder or condition. As used herein, the term "protecting" or "protection of" encompasses "treating" or "preventing" the disease, disorder or condition.

"Treating" or "treatment of", or "preventing" or "prevention of", as used herein, refers to an approach for obtaining beneficial or desired results, including clinical results. Beneficial or desired results can include, but are not limited to, alleviation or amelioration of one or more symptoms or conditions, diminishment of extent of disease, stabilisation of the state of disease, prevention of development of disease, prevention of spread of disease, delay or slowing of disease progression (e.g. suppression), delay or slowing of disease onset, conferring protective immunity against a disease-causing agent and amelioration or palliation of the disease state. "Treating" or "preventing" can also mean prolonging survival of a patient beyond that expected in the absence of treatment and can also mean inhibiting the progression of disease temporarily or preventing the occurrence of disease, such as by preventing infection in a subject. "Treating" or "preventing" may also refer to a reduction in the size of a tumor mass, reduction in tumor aggressiveness, etc.

In some embodiments, the lipid A mimics disclosed herein may be included in a pharmaceutical or vaccine composition to "improve the efficacy" of the composition. This may involve, for example, improving the efficacy of the composition in inducing either or both of a humoral immune response or a cell-mediated immune response. In some embodiments, this may involve accelerating the appearance of an immune response; improving the persistence or strength of an immune response; increasing the number of immune cells at a site of vaccination or at a tumor site; or improving a therapeutic effect provided by the composition, such as by enhancing the prophylactic and/or therapeutic treatment of a disease, disorder or condition and/or alleviating, delaying or inhibiting the progression of disease symptoms. Improving the efficacy of a composition may also be associated with an improved quality of life or a decreased morbidity.

"Improving the efficacy" of a composition may also mean that lower doses of the active ingredients are needed to produce a desired result. This encompasses both embodiments where the dosages themselves are smaller and embodiments where the composition is administered less frequently.

In some embodiments, a composition of the invention, which includes a lipid A mimic as disclosed herein, may be suitable for use in inducing or potentiating an antibody and/or cell-mediated immune response against an antigen in a subject. For example, inclusion of a lipid A mimic as disclosed herein in the composition may enhance the antibody and/or cell-mediated immune response to the antigen, as compared to a composition that does not contain the lipid A mimic (e.g. control composition).

In some embodiments, a composition of the invention, which includes a lipid A mimic as disclosed herein, may be suitable for use in the treatment and/or prevention of a viral infection in a subject in need thereof. The subject may be infected with a virus or may be at risk of developing a viral infection. Viral infections that may be treated and/or prevented by the use or administration of a composition of the invention include, without limitation, Cowpoxvirus, Vaccinia virus, Pseudocowpox virus, Human herpesvirus 1, Human herpesvirus 2, Cytomegalovirus, Human adenovirus A-F, Polyomavirus, Human papillomavirus (HPV), Parvovirus, Hepatitis A virus, Hepatitis B virus, Hepatitis C virus, Human immunodeficiency virus, Orthoreovirus, Rotavirus, Ebola virus, parainfluenza virus, influenza A virus, influenza B virus, influenza C virus, Measles virus, Mumps virus, Rubella virus, Pneumovirus, Human respiratory syncytial virus, Rabies virus, California encephalitis virus, Japanese encephalitis virus, Hantaan virus, Lymphocytic choriomeningitis virus, Coronavirus, Enterovirus, Rhinovirus, Poliovirus, Norovirus, Flavivirus, Dengue virus, West Nile virus, Yellow fever virus and varicella. In a particular embodiment, the viral infection is Human papillomavirus, Ebola virus, Human respiratory syncytial virus or an influenza virus.

In some embodiments, a composition of the invention, which includes a lipid A mimic as disclosed herein, may be suitable for use in the treatment and/or prevention of an infection by a non-viral pathogen (such as a bacterium or protozoan) in a subject in need thereof. The subject may be infected with the pathogen or may be at risk of developing an infection by the pathogen. Without limitation, exemplary bacterial pathogens may include Anthrax (*Bacillus anthracis*), *Brucella, Bordetella pertussis*, Candida, *Chlamydia pneumoniae, Chlamydia psittaci,* Cholera, *Clostridium botulinum, Coccidioides immitis, Cryptococcus, Diphtheria, Escherichia coli* 0157: H7, Enterohemorrhagic *Escherichia coli, Enterotoxigenic Escherichia coli, Haemophilus influenzae, Helicobacter pylori, Legionella, Leptospira, Listeria, Meningococcus, Mycoplasma pneumoniae, Mycobacterium,* Pertussis, Pneumonia, Salmonella, Shigella, *Staphylococcus, Streptococcus pneumoniae* and *Yersinia enterocolitica*. In a particular embodiment, the bacterial infection is Anthrax. Without limitation, exemplary protozoan pathogens may include those of the genus *Plasmodium* (*Plasmodium falciparum, Plasmodium malariae, Plasmodium vivax, Plasmodium ovale* or *Plasmodium knowlesi*), which cause malaria.

In some embodiments, a composition of the invention, which includes a lipid A mimic as disclosed herein, may be suitable for use in the treatment and/or prevention of a neurodegenerative disease in a subject in need thereof, wherein the neurodegenerative disease is associated with the expression of an antigen. The subject may have a neurodegenerative disease or may be at risk of developing a neurodegenerative disease. Neurodegenerative diseases that may be treated and/or prevented by the use or administration of a composition of the invention include, without limitation, Alzheimer's disease, Parkinson's disease, Huntington's disease, and amyotrophic lateral sclerosis (ALS).

In one embodiment, a composition of the invention may be used to treat and/or prevent Alzheimer's disease in a subject in need thereof. Alzheimer's disease is characterized by the association of β-amyloid plaques and/or tau proteins in the brains of patients with Alzheimer's disease (see, for example, Goedert and Spillantini, Science, 314: 777-781, 2006). Herpes simplex virus type 1 has also been proposed to play a causative role in people carrying the susceptible versions of the apoE gene (Itzhaki and Wozniak, J Alzheimers Dis 13: 393-405, 2008).

In some embodiments, a composition of the invention, which includes a lipid A mimic as disclosed herein, may be suitable for use in the treatment and/or prevention of cancer in a subject in need thereof. The subject may have cancer or may be at risk of developing cancer.

As used herein, the terms "cancer", "cancer cells", "tumor" and "tumor cells", (used interchangeably) refer to cells that exhibit abnormal growth, characterized by a significant loss of control of cell proliferation or cells that have been immortalized. The term "cancer" or "tumor" includes metastatic as well as non-metastatic cancer or tumors. A cancer may be diagnosed using criteria generally accepted in the art, including the presence of a malignant tumor.

Without limitation, cancers that may be capable of being treated and/or prevented by the use or administration of a composition of the invention include carcinoma, adenocarcinoma, lymphoma, leukemia, sarcoma, blastoma, myeloma, and germ cell tumors. Without limitation, particularly suitable embodiments may include glioblastoma, multiple myeloma, ovarian cancer, breast cancer, fallopian tube cancer, prostate cancer or peritoneal cancer. In one embodiment, the cancer may be caused by a pathogen, such as a virus. Viruses linked to the development of cancer are known to the skilled person and include, but are not limited to, human papillomaviruses (HPV), John Cunningham virus (JCV), Human herpes virus 8, Epstein Barr Virus (EBV), Merkel cell polyomavirus, Hepatitis C Virus and Human T cell leukaemia virus-1. In another embodiment, the cancer may be one that expresses one or more cancer-specific antigens (e.g. survivin).

A composition of the invention may be useful for either the treatment or prophylaxis of cancer; for example, a reduction of the severity of cancer (e.g. size of the tumor, aggressiveness and/or invasiveness, malignancy, etc) or the prevention of cancer recurrences.

Figure 4:
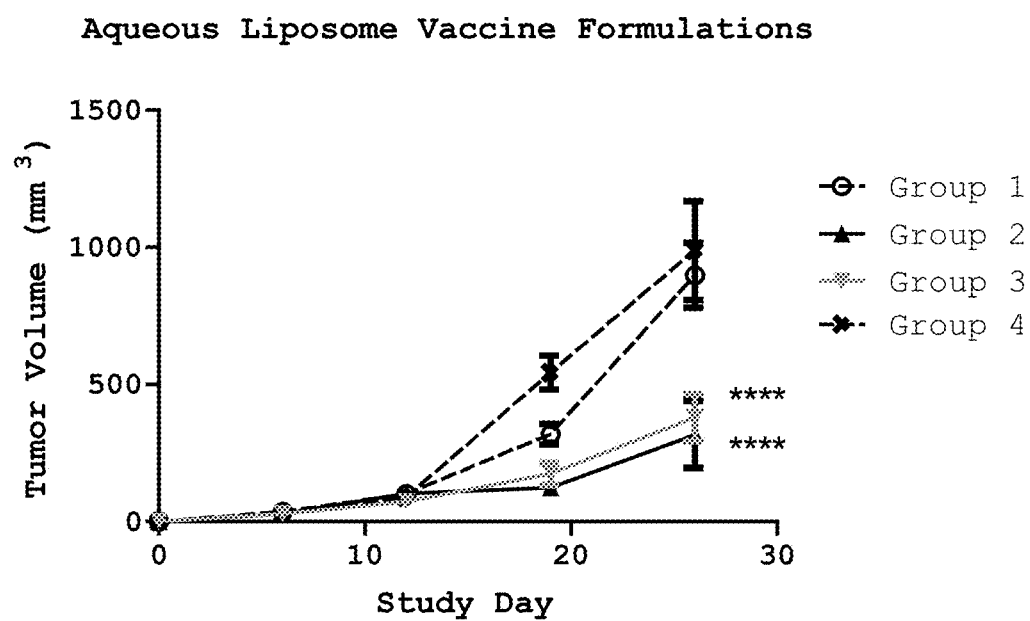
FIG. 4 illustrates the reduction in tumor volume generated by aqueous liposome vaccine compositions of the invention comprising exemplary lipid A mimics JL-265 and JL-266. Mice (C57BL6) were implanted with C3 tumors subcutaneously on day 0. On day 5, groups of mice (n=7) were vaccinated as follows: Mice in Group 1 were vaccinated with FP peptide (10 micrograms) in liposomes containing no adjuvant. Mice in Group 2 were vaccinated with FP peptide (10 micrograms) in liposomes containing JL-265 (10 micrograms). Mice in Group 3 were vaccinated with FP peptide (10 micrograms) in liposomes containing JL-266 (10 micrograms). Mice in Group 4 served as a tumor growth control and were vaccinated with saline containing no antigen or adjuvant. Tumor size was measured weekly with calipers. Significance calculated by 2-way ANOVA with Bonferroni post test comparing each group to Group 4 control: ****, $p<0.0001$.
Figure 5:
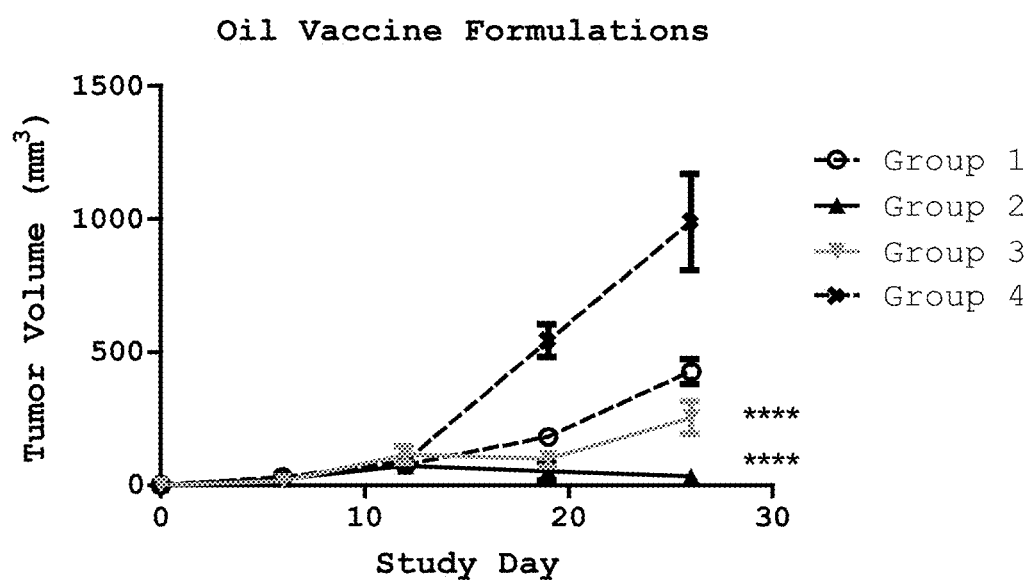
FIG. 5 illustrates the reduction in tumor volume generated by oil-based vaccine compositions of the invention comprising exemplary lipid A mimics JL-265 and JL-266. Mice (C57BL6) were implanted with C3 tumors subcutaneously on day 0. On day 5, groups of mice (n=7) were vaccinated as follows: Mice in Group 1 were vaccinated with FP peptide (10 micrograms) in oil containing no adjuvant. Mice in Group 2 were vaccinated with FP peptide (10 micrograms) in oil containing JL-265 (10 micrograms). Mice in Group 3 were vaccinated with FP peptide (10 micrograms) in oil containing JL-266 (10 micrograms). Mice in Group 4 served as a tumor growth control and were vaccinated with saline containing no antigen or adjuvant. Tumor size was measured weekly with calipers. Significance calculated by 2-way ANOVA with Bonferroni post test comparing each group to Group 4 control: ****, $p<0.0001$.

It has been found that vaccine compositions of the invention that comprise lipid A mimic JL-265 or JL-266 are capable of significantly reducing tumor volumes in mice, as compared a similar composition that does not include a lipid A mimic (Examples 10 and 11; FIGS. 4 and 5). The data described in Example 10 herein is summarized below in Table 1.

TABLE 1

| Group | Composition | Tumor Volume (mm$^3$) |
|---|---|---|
| 1 | HPV Antigen<br>PADRE T helper epitope<br>Liposomes<br>Water Carrier | 898 ± 118 |
| 2 | HPV Antigen<br>PADRE T helper epitope<br>JL-265 Lipid A Mimic<br>Liposomes<br>Water Carrier | 319 ± 122 |
| 3 | HPV Antigen<br>PADRE T helper epitope<br>JL-266 Lipid A Mimic<br>Liposomes<br>Water Carrier | 380 ± 86 |
| 4 | Saline | 989 ± 181 |

It can be seen from the above table (Table 1) that the compositions of the invention (Groups 2 and 3) resulted in tumor volumes in mice that were about 2.8 and 2.4-fold smaller, respectively, than those observed in mice vaccinated with a control composition that did not contain a lipid A mimic (Group 1).

Notably, the results are even more pronounced when the vaccine compositions are suspended in Immunovaccine, Inc's liposome-based vaccine adjuvanting platform DepoVax™, in which a dry mixture of amphipathic compound (liposomes), antigen and lipid A mimic are suspended in a mineral oil-based hydrophobic carrier. As shown in Table 2 below, which summarizes the data described in Example 12 (FIG. 6), the DepoVax™ compositions of the invention (Groups 2 and 3) resulted in tumor volumes in mice that were about 3.1-fold (JL-265) and 6.3-fold (JL-266) smaller, respectively, than those observed in mice vaccinated with a control DepoVax™ composition that does contain a lipid A mimic (i.e. Group 1).

TABLE 2

| Group | Composition | Tumor Volume (mm$^3$) |
|---|---|---|
| 1 | HPV Antigen<br>PADRE T helper epitope<br>DepoVax (liposomes +<br>oil-based carrier) | 1383 ± 280 |
| 2 | HPV Antigen<br>PADRE T helper epitope<br>JL-265 Lipid A Mimic<br>DepoVax (liposomes +<br>oil-based carrier) | 445 ± 395 |
| 3 | HPV Antigen<br>PADRE T helper epitope<br>JL-266 Lipid A Mimic<br>DepoVax (liposomes +<br>oil-based carrier) | 219 ± 139 |
| 4 | Saline | 1690 ± 359 |

It is clear from the collection of examples described above, and further herein, that embodiments of the vaccine compositions of the invention, which comprise lipid A mimic JL-265 or JL-266, are capable of significantly reducing tumorigenicity in mice with implanted tumors (e.g. reducing the growth rate and the overall tumor volume). The examples also show that there is more than one way to make a composition of the invention, and that compositions formulated using DepoVax™ provide an even more pronounced reduction in tumor size.

Similarly, embodiments of the compositions of the invention were found to be immunogenic. Example 14 tested the immunogenicity of vaccines of the invention containing both an MHC Class I epitope (R9F) and an MHC Class II epitope (F21E), together with JL-265 or JL-266 lipid A mimics, formulated in DepoVax™. The IFN-gamma ELISPOT assay can provide information on the relative immunogenicity of different vaccine formulations, but is not always indicative of efficacy in the more relevant tumor challenge assay.

Figure 8:
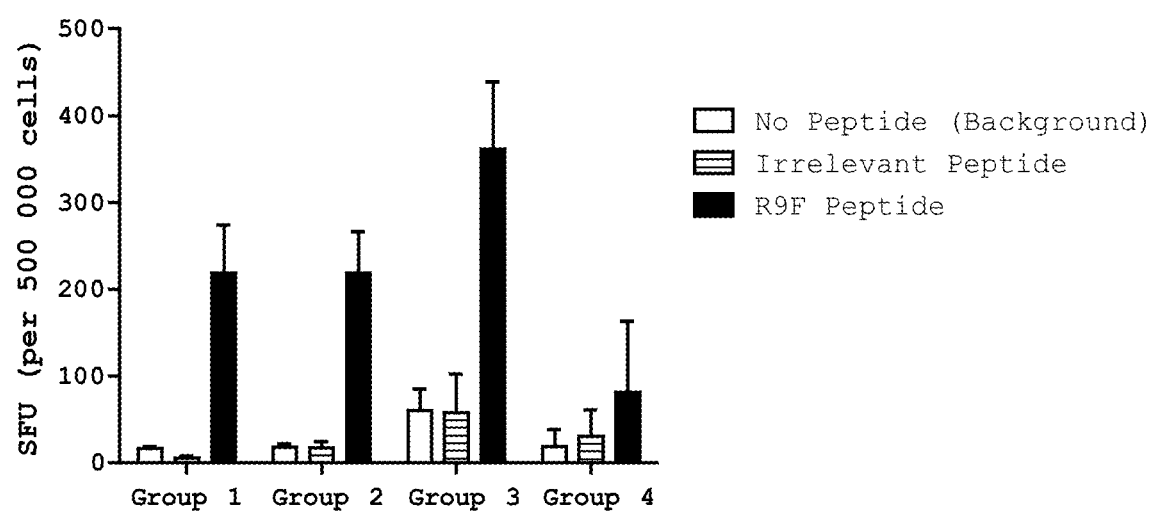
FIG. 8 illustrates the immunogenicity of generated by DepoVax™ (DPX) vaccine compositions of the invention comprising exemplary lipid A mimics JL-265 and JL-266. Groups of mice (C57BL6) were vaccinated as follows: Mice in Group 1 (N=5) were vaccinated with R9F+F21E peptides (5 micrograms each) in DPX containing no adjuvant. Mice in Group 2 (N=5) were vaccinated with R9F+F21E peptides (5 micrograms each) in DPX containing JL-265 (5 micrograms). Mice in Group 3 (N=5) were vaccinated with R9F+F21E peptides (5 micrograms each) in DPX containing JL-266 (5 micrograms). Mice in Group 4 (N=2) were not vaccinated.

In Example 14, although the composition containing the JL-265 lipid A mimic (Group 2) did not enhance the antigen-specific IFN-gamma response to R9F, it was still capable of generating an immune response. More significantly, a composition containing the JL-266 resulted in a nearly 2-fold increase in the immune response (FIG. 8). It is clear from these results that embodiments of the vaccine compositions of the invention, which comprise lipid A mimic JL-265 or JL-266, are immunogenic and in certain embodiments are capable of significantly enhancing the immune response to an antigen.

Pharmaceutical Administration

Generally, the lipid A mimics, pharmaceutical compositions or vaccine compositions may be administered by any means known in the art.

For example, and without limitation, the compositions as described herein may be formulated in a form that is suitable for oral, nasal, rectal or parenteral administration, and if parenteral, either locally or systemically. Parenteral administration includes, without limitation, intravenous, intraperitoneal, intradermal, subcutaneous, intramuscular, intranasal, transdermal, transepithelial, intrapulmonary, intrathecal, and topical or buccal modes of administration. Parenteral administration can be by bolus injection or by gradual perfusion over time. In particular embodiments, the route of administration may be intramuscular, subcutaneous or intradermal to achieve a depot effect when using, for example, a DepoVax™ composition of the invention.

The skilled artisan can determine suitable treatment regimes, routes of administration, dosages, etc., for any particular application. Factors that may be taken into account include, e.g.: the nature of the antigen; the disease state to be prevented or treated; the age, physical condition, body weight, sex and diet of the subject; and other clinical factors. See, for example, "Vaccine Handbook", edited by the Researcher's Associates (Gaku-yuu-kai) of The National Institute of Health (1994); "Manual of Prophylactic Inoculation, 8th edition", edited by Mikio Kimura, Munehiro Hirayama, and Harumi Sakai, Kindai Shuppan (2000); "Minimum Requirements for Biological Products", edited by the Association of Biologicals Manufacturers of Japan (1993).

The optimal amount of lipid A mimics and antigen may depend on a number of factors including, without limitation, the composition, the disease, the subject, and may be readily ascertained by the skilled person using standard studies including, for example, observations of antibody titers, antigen-specific IFN-gamma responses, measurements of tumor volume or other characteristics, and other immunogenic responses in the host.

The compositions as described herein may potentially be effective when administered in a single application.

In some embodiments, the compositions as described herein may be used in combination, before or after, with other therapies.

The subject to be treated with the lipid A mimics, pharmaceutical or vaccine compositions described herein may be any vertebrate, more particularly a mammal. In an embodiment, the subject is a human.

Kits and Reagents

The lipid A mimics or compositions disclosed herein are optionally provided to a user as a kit. For example, a kit of the invention contains one or more components of the compositions of the invention. The kit can further comprise one or more additional reagents, packaging material, containers for holding the components of the kit, and an instruction set or user manual detailing preferred methods of using the kit components.

In a particular embodiment, the vaccine composition of the invention is supplied as a kit containing two containers. Container 1, for example, may comprise the lyophilized amphipathic compound (e.g. liposomes), antigen and lipid A mimic. Container 2, for example, may contain the hydrophobic carrier (e.g. mineral oil-based carrier) alone.

Embodiments of the Invention

Particular embodiments of the invention include, without limitation, the following:

(1) A compound of Formula:

$$A-L_1-D-L_2-E$$

wherein:

A is a cyclic monosaccharide residue with one or more of the hydroxyl groups optionally substituted or absent, or A is a substituted or unsubstituted aromatic group;

$L_1$ and $L_2$ independently are present or absent, and if present is independently a substituted or unsubstituted, branched or linear, saturated or unsaturated, carbon chain optionally comprising one or more of O, S or N;

D is —O—, —S— or —NH—; and

E is a cyclic monosaccharide residue with one or more of the hydroxyl groups optionally substituted or absent, or E is a substituted or unsubstituted aromatic group;

wherein at least one of A or E is a substituted or unsubstituted aromatic group and at least one of A, $L_1$, $L_2$ or E comprises one or more lipid chain substituents;

or a pharmaceutically acceptable salt thereof.

(2) The compound of paragraph (1), or pharmaceutically acceptable salt thereof, wherein at least one of A or E is a substituted or unsubstituted aromatic group having 3 to 26 total ring atoms.

(3) The compound of paragraph (1) or (2), or pharmaceutically acceptable salt thereof, wherein at least one of A or E is an aromatic group selected from:

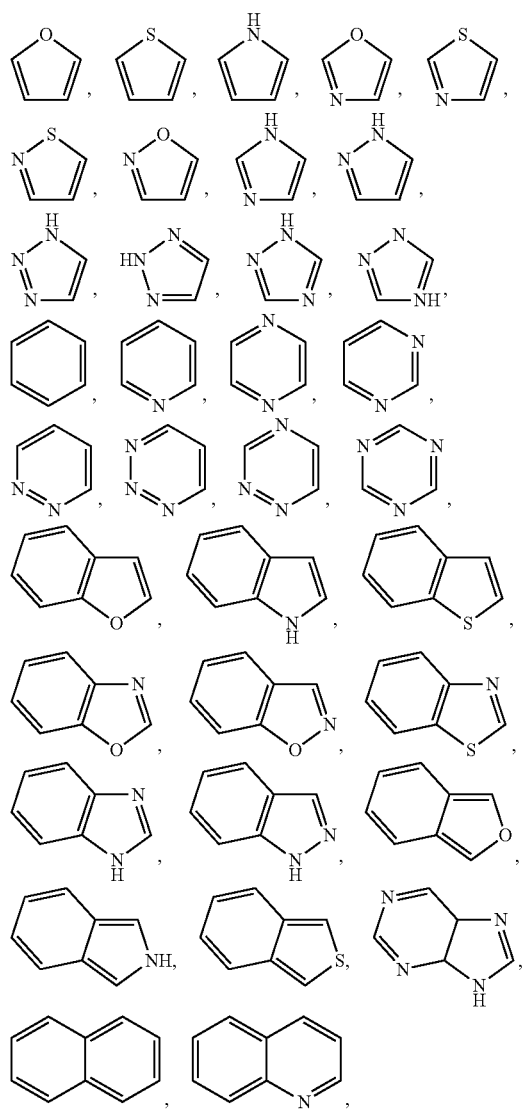

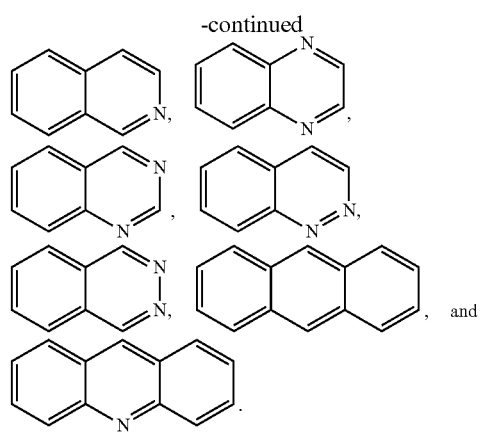

wherein the aromatic group is optionally substituted or unsubstituted.

(4) The compound of any one of paragraphs (1) to (3), or pharmaceutically acceptable salt thereof, wherein at least one of A or E is a carbocyclic aromatic group comprising one, two or three substituted or unsubstituted aromatic rings.

(5) The compound of any one of paragraphs (1) to (3), or pharmaceutically acceptable salt thereof, wherein at least one of A or E is a substituted or unsubstituted monocyclic carbocyclic aromatic group or a substituted or unsubstituted monocyclic heteroaromatic group.

(6) The compound of any one of paragraphs (1) to (5), or pharmaceutically acceptable salt thereof, wherein at least one of A or E is a substituted or unsubstituted benzene ring.

(7) The compound of any one of paragraphs (1) to (6), or pharmaceutically acceptable salt thereof, wherein at least one of A or E is:

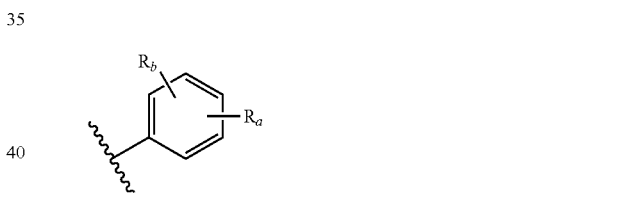

wherein:

$R_a$ is placed at any position on the benzene ring and is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6; and $R_b$ is placed at any remaining position on the benzene ring and is —H, —OH, —NH$_2$, —Cl, —Br, —F, —COOH, —CN, —SO$_3$H, —OCH$_3$, —NO$_2$ or any substituted or unsubstituted C$_{1-6}$ alkyl.

(8) The compound of any one of paragraphs (1) to (7), or pharmaceutically acceptable salt thereof, wherein at least one of A or E is:

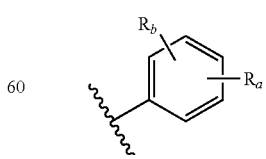

wherein:

$R_a$ is placed at any position on the benzene ring and is —H, —OH or —OP(O)(OH)$_2$; and $R_b$ is —H.

(9) The compound of any one of paragraphs (1) to (8), or pharmaceutically acceptable salt thereof, wherein at least one of A or E is:

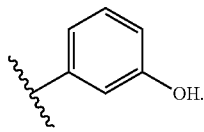 [SMILES: *c1cccc(O)c1]

(10) The compound of any one of paragraphs (1) to (8), or pharmaceutically acceptable salt thereof, wherein at least one of A or E is:

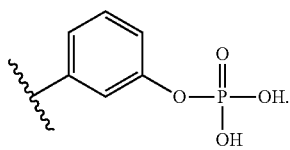 [SMILES: *c1cccc(OP(=O)(O)O)c1]

(11) The compound of any one of paragraphs (1) to (6), or pharmaceutically acceptable salt thereof, wherein at least one of A or E is:

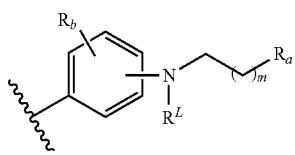

wherein:

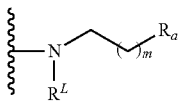

is placed at any position on the benzene ring;
$R_a$ is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6; m is 0-6;
$R^L$ is a lipid chain substituent; and
$R_b$ is placed at any remaining position on the benzene ring and is —H, —OH, —Cl, —Br, —F, —COOH, —CN, —SO$_3$H, —OCH$_3$, —NO$_2$ or any substituted or unsubstituted C$_{1-6}$ alkyl.

(12) The compound of any one of paragraphs (1) to (11), or pharmaceutically acceptable salt thereof, wherein one of A or E is the cyclic monosaccharide residue with one or more of the hydroxyl groups optionally substituted or absent.

(13) The compound of paragraph (12), or pharmaceutically acceptable salt thereof, wherein the cyclic monosaccharide sugar residue is a pyranose sugar residue with one or more of the hydroxyl groups optionally substituted or absent.

(14) The compound of paragraph (13), or pharmaceutically acceptable salt thereof, wherein the pyranose sugar residue comprises a glucopyranose ring or a galactopyranose ring, with one or more of the hydroxyl groups optionally substituted or absent.

(15) The compound of any one of paragraphs (1) to (14), or pharmaceutically acceptable salt thereof, wherein A is:

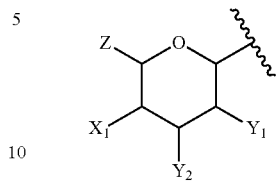

wherein:
Z is —CH$_2$G or —CH$_2$MQ, wherein G is —H, -halogen, —OH, —NH$_2$, —COOH, —OSO$_3$H, —SO$_3$H, —P(O)(OH)$_2$, or —OP(O)(OH)$_2$; M is —O—, —S—, —NH—, —OC(=O)—, —SC(=O)—, —OC(=S)—, or —NHC(=O)—; and Q is —H or a substituted or unsubstituted, branched or linear, saturated or unsaturated C$_{1-20}$ aliphatic hydrocarbon;
$X_1$ is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6; and
$Y_1$ and $Y_2$ are independently —H, —OH, —O—R$^L$, —NH—R$^L$, or —S—R$^L$, wherein R$^L$ is a lipid chain substituent.

(16) The compound of paragraph (15), or pharmaceutically acceptable salt thereof, wherein Z is —CH$_2$OH.

(17) The compound of paragraph (16), or pharmaceutically acceptable salt thereof, wherein the stereochemistry of the substitutions on A are defined by the following formula:

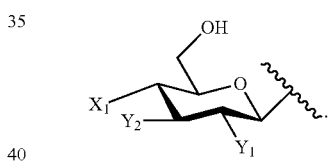

(18) The compound of any one of paragraphs (15) to (17), or pharmaceutically acceptable salt thereof, wherein $X_1$ is —OP(O)(OH)$_2$.

(19) The compound of any one of paragraphs (15) to (18), or pharmaceutically acceptable salt thereof, wherein $Y_1$ is —NH—R$^L$.

(20) The compound of any one of paragraphs (15) to (19), or pharmaceutically acceptable salt thereof, wherein $Y_2$ is —O—R$^L$.

(21) The compound of any one of paragraphs (15) to (20), or pharmaceutically acceptable salt thereof, wherein L is absent.

(22) The compound of any one of paragraphs (15) to (21), or pharmaceutically acceptable salt thereof, wherein $L_2$ is I, incorporated into formula A-L$_1$-D-L$_2$-E as follows:

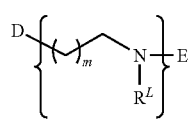

I wherein m is 0-6 and R$^L$ is a lipid chain substituent.

(23) The compound of any one of paragraphs (15) to (21), or pharmaceutically acceptable salt thereof, wherein $L_2$ is absent.

(24) The compound of any one of paragraphs (1) to (14), or pharmaceutically acceptable salt thereof, wherein E is:

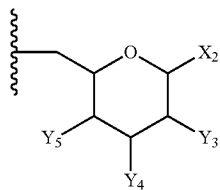

wherein:
$X_2$ is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6; and
$Y_3$, $Y_4$ and $Y_5$ are independently —H, —OH, —O—R$^L$, —NH—R$^L$, or —S—R$^L$, wherein R$^L$ is a lipid chain substituent.

(25) The compound of paragraph (24), or pharmaceutically acceptable salt thereof, wherein the stereochemistry of the substitutions on E are defined by the following formula:

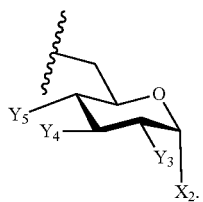

(26) The compound of paragraph (24) or (25), or pharmaceutically acceptable salt thereof, wherein $X_2$ is —OP(O)(OH)$_2$.

(27) The compound of any one of paragraphs (24) to (26), or pharmaceutically acceptable salt thereof, wherein $Y_3$ is —NH—R$^L$.

(28) The compound of any one of paragraphs (24) to (27), or pharmaceutically acceptable salt thereof, wherein $Y_4$ is —O—R$^L$.

(29) The compound of any one of paragraphs (24) to (28), or pharmaceutically acceptable salt thereof, wherein $Y_5$ is —OH.

(30) The compound of any one of paragraphs (24) to (29), or pharmaceutically acceptable salt thereof, wherein $L_2$ is absent.

(31) The compound of any one of paragraphs (24) to (30), or pharmaceutically acceptable salt thereof, wherein $L_1$ is II, incorporated into formula A-$L_1$-D-$L_2$-E as follows:

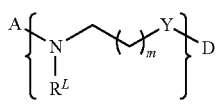

wherein m is 0-6, Y is —(CO)$_f$—, wherein f is 0 or 1, and R$^L$ is a lipid chain substituent.

(32) The compound of any one of paragraphs (24) to (30), or pharmaceutically acceptable salt thereof, wherein L is absent.

(33) The compound of any one of paragraphs (1) to (32), or pharmaceutically acceptable salt thereof, wherein D is —O—.

(34) The compound of any one of paragraphs (1) to (33), or pharmaceutically acceptable salt thereof, which comprises one, two, three, four or five lipid chain substituents.

(35) The compound of any one of paragraphs (1) to (34), or pharmaceutically acceptable salt thereof, wherein at least one of A or $L_1$ comprises one or more lipid chain substituents.

(36) The compound of any one of paragraphs (1) to (35), or pharmaceutically acceptable salt thereof, wherein at least one of E or $L_2$ comprises one or more lipid chain substituents.

(37) The compound of paragraph (1), which is: $P_{GP}$-9$_3$,C1

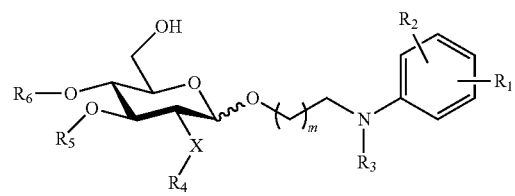

wherein:
the glycosidic linkage is α or β;
X is O or NH;
m is 0-6;
$R_1$ is placed in ortho-, meta-, or para-position to the N-substituent on the benzene ring and is —H, —OH, —OP(O)(OH)$_2$, —COOH, —SO$_3$H, —(O)$_k$(CH$_2$)$_n$COOH or —(O)$_k$(CH$_2$)$_q$OP(O)(OH)$_2$; wherein k is 0 or 1, n is 0-4, and q is 2-6;
$R_2$ is placed at any remaining position of the benzene ring and is —H, —OH, —Cl, —Br, —F, —COOH, —CN, —SO$_3$H, —OCH$_3$, —NO$_2$, or a C1-6 alkyl optionally substituted or unsubstituted;
$R_3$, $R_4$, and $R_5$ are each independently a lipid chain substituent; and
$R_6$ is —H, —P(O)(OH)$_2$, or —CH$_2$COOH,
or a pharmaceutically acceptable salt thereof.

(38) The compound of paragraph (1), which is:

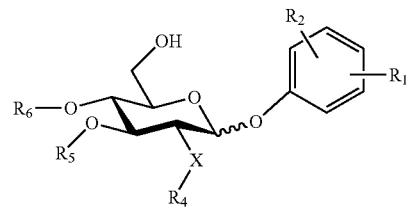

wherein:
the glycosidic linkage is α or β;
X is O or NH;
$R_1$ is placed in ortho-, meta-, or para-position to the N-substituent on the benzene ring and is:

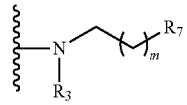

$R_7$ is —H, —OH, —OP(O)(OH)$_2$, —COOH, —SO$_3$H, —(O)$_k$(CH$_2$)$_n$COOH, or —(O)$_k$(CH$_2$)$_q$OP(O)(OH)$_2$; wherein k is 0 or 1, n is 0-4, and q is 2-6;
m is 0-6;

$R_2$ is placed at any remaining position of the benzene ring and is —H, —OH, —Cl, —Br, —F, —COOH, —CN, —SO$_3$H, —OCH$_3$, —NO$_2$, or a C$_{1-6}$ alkyl optionally substituted or unsubstituted;

$R_3$, $R_4$, and $R_5$ are each independently a lipid chain substituent; and $R_6$ is —H, —P(O)(OH)$_2$, or —CH$_2$COOH, or a pharmaceutically acceptable salt thereof.

(39) The compound of paragraph (1), which is:

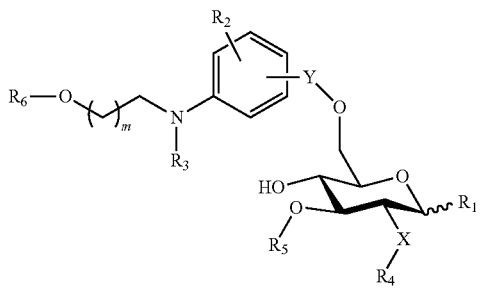

wherein:
the glycosidic linkage is α or β;
X is O or NH;
m is 0-6;
Y is placed in ortho-, meta-, or para-position to the N-substituent on the benzene ring and is —(O)$_g$(CH$_2$)$_h$(CO)$_j$—, wherein g is 0 or 1, h is 0-6, and j is 0 or 1;
$R_2$ is placed at any remaining position of the benzene ring and is —H, —OH, —Cl, —Br, —F, —COOH, —CN, —SO$_3$H, —OCH$_3$, —NO$_2$, or a C1-6 alkyl optionally substituted or unsubstituted;
$R_1$ is —H, —OH, —OP(O)(OH)$_2$, —COOH, —SO$_3$H, —(O)$_k$(CH$_2$)$_n$COOH, or —(O)$_k$(CH$_2$)$_q$OP(O)(OH)$_2$; wherein k is 0 or 1, n is 0-4, and q is 2-6;
$R_3$, $R_4$, and $R_5$ are each independently a lipid chain substituent; and
$R_6$ is —H, —P(O)(OH)$_2$, or —CH$_2$COOH,
or a pharmaceutically acceptable salt thereof.

(40) The compound of paragraph (1), which is:

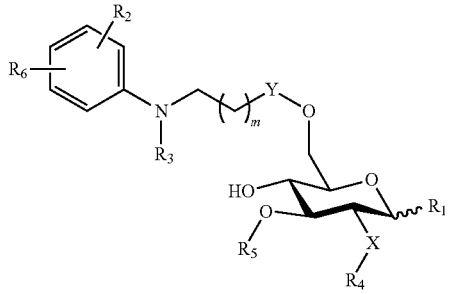

wherein:
the glycosidic linkage is α or β;
X is O or NH;
m is 0-6;
$R_6$ is placed in ortho-, meta-, or para-position to the N-substituent on the benzene ring and is —H, —OH, —OP(O)(OH)$_2$, —COOH, —SO$_3$H, —(O)$_k$(CH$_2$)$_n$COOH, or —(O)$_k$(CH$_2$)$_q$OP(O)(OH)$_2$; wherein k is 0 or 1, n is 0-4, and q is 2-6;
$R_2$ is placed at any remaining position of the benzene ring and is —H, —OH, —Cl, —Br, —F, —COOH, —CN, —SO$_3$H, —OCH$_3$, —NO$_2$, or a C$_{1-6}$ alkyl optionally substituted or unsubstituted;

Y is —(CO)$_f$—, wherein f is 0 or 1;
$R_1$ is —H, —OH, —OP(O)(OH)$_2$, —COOH, —SO$_3$H, —(O)$_k$(CH$_2$)$_n$COOH, or —(O)$_k$(CH$_2$)$_q$OP(O)(OH)$_2$; wherein k is 0 or 1, n is 0-4, and q is 2-6; and
$R_3$, $R_4$, and $R_5$ are each independently a lipid chain substituent,
or a pharmaceutically acceptable salt thereof.

(41) The compound of any one of paragraphs (1) to (40), or pharmaceutically acceptable salt thereof, wherein each lipid chain substituent independently comprises a strongly lipophilic group, which is the same or different than any other lipid chain substituent present in the compound.

(42) The compound of any one of paragraphs (1) to (41), or pharmaceutically acceptable salt thereof, wherein each lipid chain substituent independently comprises one, two or three major carbon chains.

(43) The compound of any one of paragraphs (1) to (42), or pharmaceutically acceptable salt thereof, wherein the lipid chain substituents present in the compound collectively provide two, three, four, five, six, seven, eight, nine or ten major carbon chains.

(44) The compound of paragraph (42) or (43), or pharmaceutically acceptable salt thereof, wherein each major carbon chain is 1-22 carbons.

(45) The compound of paragraph (44), or pharmaceutically acceptable salt thereof, wherein each major carbon chain is 4-18 carbons.

(46) The compound of paragraph (45), or pharmaceutically acceptable salt thereof, wherein each major carbon chain is 14 carbons.

(47) The compound of any one of paragraphs (1) to (46), or pharmaceutically acceptable salt thereof, wherein each lipid chain substituent is independently a C$_{1-66}$ straight chain or branched chain alkyl which optionally comprises at least one element selected from —O—, —S—, —NH—, —C=C—, —C≡C—, —C(=O)— or —C(=S)—, and is optionally substituted with halogen, —OH or —NH$_2$.

(48) The compound of paragraph (47), or pharmaceutically acceptable salt thereof, wherein each lipid chain substituent is independently a C$_{4-42}$ straight chain or branched chain alkyl which optionally comprises at least one element selected from —O—, —S—, —NH—, —C=C—, —C≡C—, —C(=O)— or —C(=S)—, and is optionally substituted with halogen, —OH or —NH$_2$.

(49) The compound of paragraph (48), or pharmaceutically acceptable salt thereof, wherein each lipid chain substituent is independently a C$_{14-28}$ straight chain or branched chain alkyl which optionally comprises at least one element selected from —O—, —S—, —NH—, —C=C—, —C≡C—, —C(=O)— or —C(=S)—, and is optionally substituted with halogen, —OH or —NH$_2$.

(50) The compound of any one of paragraphs (1) to (49), or pharmaceutically acceptable salt thereof, wherein each lipid chain substituent is independently:

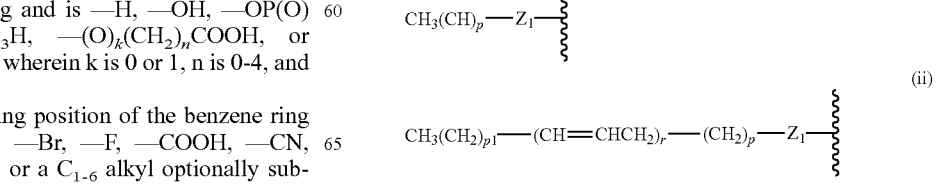

-continued
(iii) 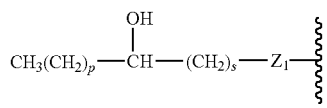
(iv) 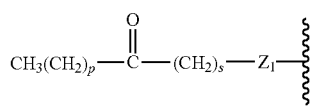
(v) 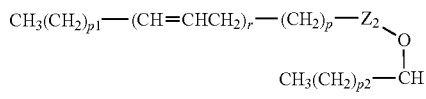
(vi) 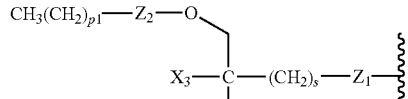
(vii) 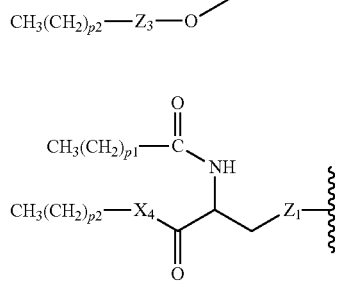
(viii) 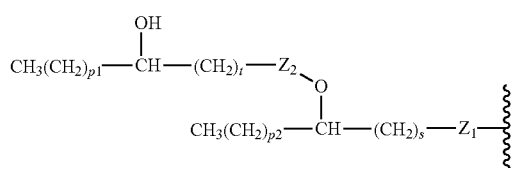
(ix) 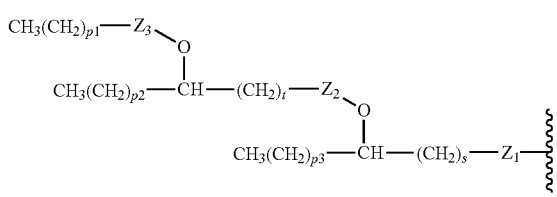
wherein:
$Z_1$, $Z_2$ and $Z_3$ are independently —C(=O)—, or —CH$_2$—;
$X_3$ is —H or —(CH$_2$)$_{p3}$CH$_3$;
$X_4$ is —NH—, —O— or —CH$_2$—;
p, p1, p2 and p3 are independently 0-30; and
r, s and t are independently 0-6.
(51) The compound of any one of paragraphs (1) to (50), or pharmaceutically acceptable salt thereof, wherein each lipid chain substituent is independently:
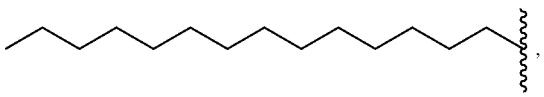,
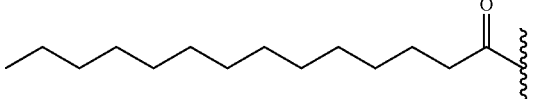,
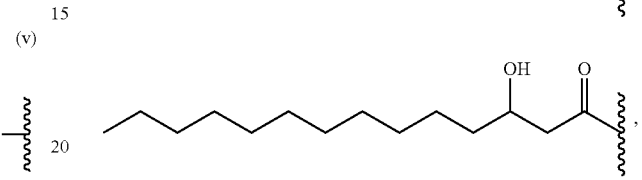,
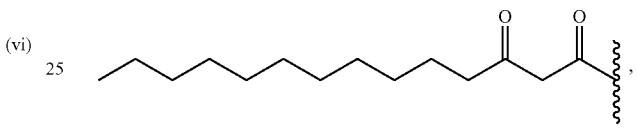,
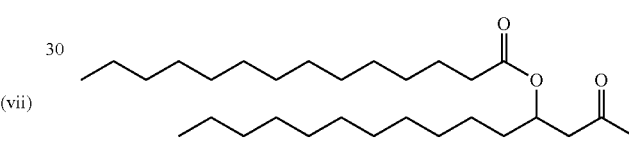,
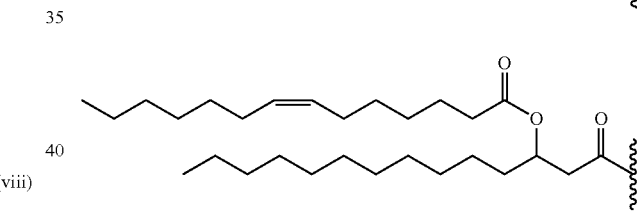,
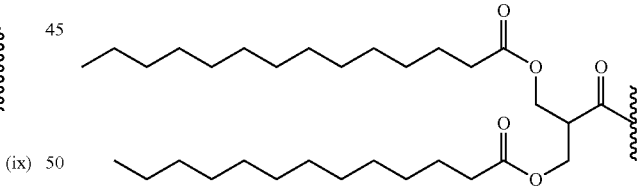,
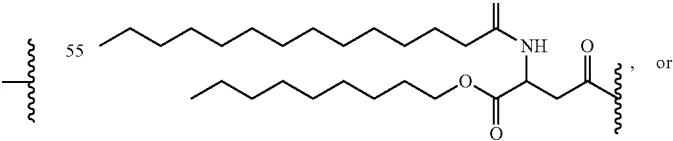, or
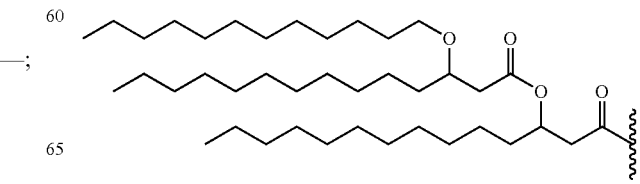.

(52) The compound of paragraph (1), which is:

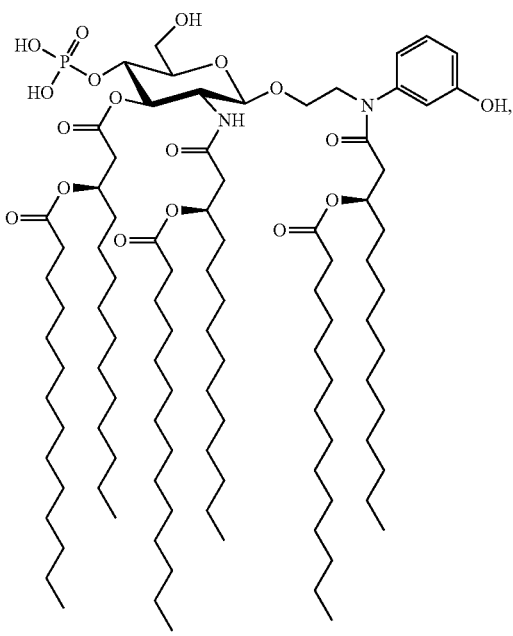

or a pharmaceutically acceptable salt thereof.

(53) The compound of paragraph (1), which is:

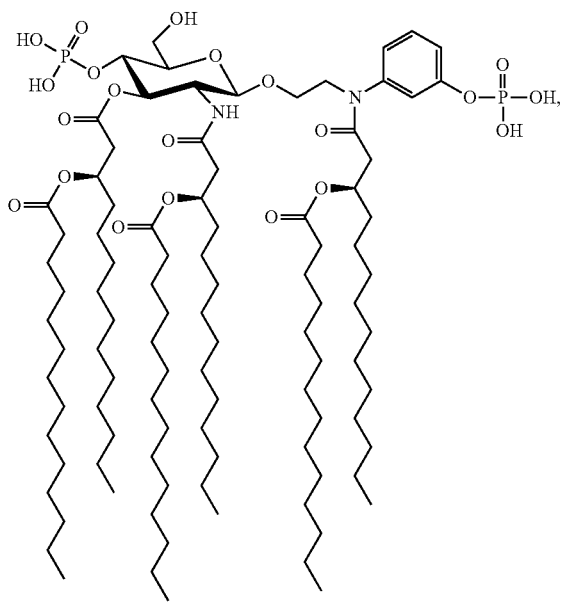

or a pharmaceutically acceptable salt thereof.

(54) The compound of any one of paragraphs (1) to (53), or pharmaceutically acceptable salt thereof, which has lipid A or lipopolysaccharide (LPS) antagonist activity.

(55) The compound of any one of paragraphs (1) to (53), or pharmaceutically acceptable salt thereof, which has immunostimulatory activity.

(56) The compound of any one of paragraphs (1) to (55), or pharmaceutically acceptable salt thereof, which is capable of binding to toll-like receptor 4 (TLR4).

(57) A pharmaceutical composition comprising the compound of any one of paragraphs (1) to (53), or pharmaceutically acceptable salt thereof, and a pharmaceutically acceptable carrier, diluent or excipient.

(58) The pharmaceutical composition of paragraph (57) for use in the treatment or prevention of a lipopolysaccharide (LPS)/lipid A-mediated disease or disorder.

(59) A method for treating or preventing a lipopolysaccharide (LPS)/lipid A-mediated disease or disorder in a subject, said method comprising administering to the subject the composition of paragraph (57).

(60) A vaccine composition comprising the compound of any one of paragraphs (1) to (53), or pharmaceutically acceptable salt thereof, and an antigen.

(61) The vaccine composition of paragraph (60), which further comprises liposomes.

(62) The vaccine composition of paragraph (60) or (61), which further comprises a carrier comprising a continuous phase of a hydrophobic substance.

(63) The vaccine composition of paragraph (62), wherein the carrier comprising a continuous phase of a hydrophobic substance is a mineral oil-based carrier.

(64) The vaccine composition of any one of paragraph (60) to (63), which further comprises a T-helper epitope.

(65) The vaccine composition of any one of paragraph (60) to (64), wherein the antigen is one that is associated with cancer, an infectious disease or an addiction disease.

(66) The vaccine composition of paragraph (65), wherein the antigen is derived from a virus, bacterium or protozoan, such as for example Ebola virus, human papillomavirus (HPV), influenza virus, respiratory syncytial virus, *Bordetella pertussis*, *Bacillus anthracis* or *Plasmodium malariae*.

(67) The vaccine composition of paragraph (65), wherein the antigen is a membrane surface-bound cancer antigen, such as for example a survivin antigen.

(68) The vaccine composition of paragraph (65), wherein the antigen is a toxin, such as for example cocaine.

(69) The vaccine composition of any one of paragraphs (60) to (68), wherein the antigen comprises at least one B cell epitope, at least one CTL epitope or a combination thereof.

(70) The vaccine composition of any one of paragraphs (60) to (69) for use in inducing an antibody response and/or a cell-mediated immune response against the antigen in a subject.

(71) The vaccine composition of any one of paragraphs (60) to (69) for use in the treatment or prevention of cancer; an infectious disease; or an addiction disease.

(72) A method for inducing or potentiating an antibody and/or cell-mediated immune response against an antigen in a subject, said method comprising administering to the subject the vaccine composition of any one of paragraphs (60) to (69).

(73) The method of paragraph (72), wherein the antibody and/or cell-mediated immune response is enhanced by the compound of any one of paragraphs (1) to (53) or pharmaceutically acceptable salt thereof.

(74) A method for treating or preventing cancer; an infectious disease; or an addiction disease, said method comprising administering to the subject the vaccine composition of any one of paragraphs (60) to (69).

(75) The method of paragraph (74), wherein the compound of any one of paragraphs (1) to (53), or pharmaceutically acceptable salt thereof, improves the efficacy of the vaccine composition in treating or preventing the cancer, infectious disease or addiction disease as compared to a control vaccine composition that does not comprise the compound or pharmaceutically acceptable salt thereof.

(76) Use of the pharmaceutical composition of paragraph (57) in the treatment or prevention of a lipopolysaccharide (LPS)/lipid A-mediated disease or disorder in a subject.

(77) Use of the vaccine composition of any one of paragraphs (60) to (69), for inducing or potentiating an antibody and/or cell-mediated immune response against an antigen; or for treating or preventing cancer, an infectious disease, or an addiction disease.

The invention is further illustrated by the following non-limiting examples.

EXAMPLES

Example 1: Preparation of N-(2-hydroxyethyl)-3-aminophenol (4)

To a solution of 3-aminophenol (5.00 g, 45.82 mmol) and sodium bicarbonate (8.85 g, 105.39 mmol) in water (7 mL) heated to 90° C., 2-chloroethanol (3.4 mL, 50.40 mmol) was added dropwise over 5 minutes and the mixture was stirred overnight. Solids were filtered off through a celite pad, and the filtrate concentrated in vacuo. The resulting residue was washed three times with a $CH_2Cl_2$:MeOH solution (9:1, 10 mL), and the combined washes concentrated. Purification via repeated flash chromatography ($CH_2Cl_2$/MeOH, 95:5→90:10) afforded 4 (4.10 g, 58%) as a brown solid. Rf 0.31 ($CH_2Cl_2$/MeOH, 95:5); $[\alpha]_D^{22}$ −0.7 (c 1.0, $CHCl_3$); $^1$H NMR (500 MHz, $CDCl_3$): δ 3.15 (t, 2H, J 5.5 Hz, $NCH_2$), 3.68 (t, 2H, J 5.5 Hz, $OCH_2$), 4.58-4.96 (br s, 3H, NH, OH×2), 6.15-6.19 (m, 3H, Ar—H), 6.93 (dd, 1H, J 8.5, 8.5 Hz, Ar—H); $^{13}$C NMR (125 MHz, $CDCl_3$): δ 45.88 ($\underline{N}CH_2$), 60.30 ($O\underline{C}H_2$), 100.04 ($\underline{C}H$—Ar), 104.58 ($\underline{C}H$—Ar), 105.42 ($\underline{C}H$—Ar), 129.81 ($\underline{C}H$—Ar), 149.96 ($\underline{C}$—Ar), 157.69 ($\underline{C}$—Ar); HRESI-MS (m/z) Calcd for $C_8H_{11}NO_2$ [M+H]$^+$: 154.0868, found: 154.0858.

Example 2: Preparation of N-(2-(tert-butyldiphenylsilyloxy)ethyl)-3-aminophenol (5)

To a cooled solution (ice water bath) of 4 (864 mg, 5.62 mmol) and imidazole (573 mg, 8.43 mmol) in DMF (5.0 mL), tert-butyldiphenylsilyl chloride (1.60 mL, 6.18 mmol) was added dropwise over 2 minutes. The temperature was slowly allowed to rise to room temperature over 2 hours, and the mixture was stirred overnight. The mixture was concentrated, dissolved in EtOAc (60 mL), and washed with water (40 mL). The aqueous layer was further extracted with EtOAc (2×60 mL), with the combined organic layers dried over $Na_2SO_4$ and concentrated. Flash column chromatography purification (hexane/EtOAc, 3:1) afforded 5 (1.86 g, 84%) as a brown solid. Rf 0.38 (hexane/EtOAc, 3:1); $[\alpha]_D^{22}$ +3.4 (c 1.0, $CHCl_3$); $^1$H NMR (500 MHz, $CDCl_3$): δ 1.06 (s, 9H, $C(CH_3)_3$), 3.22 (t, 2H, J 5.5 Hz, $NCH_2$), 3.85 (t, 2H, J 5.5 Hz, $OCH_2$), 4.02-4.18 (br s, 1H, NH), 4.60-4.74 (br s, 2H, OH×2), 6.01 (s, 1H, Ar—H), 6.15-6.18 (m, 2H, Ar—H), 6.99 (dd, 1H, J 8.0, 8.0 Hz, Ar—H), 7.37-7.44 (m, 6H, Ar—H), 7.65-7.67 (m, 4H, Ar—H); $^{13}$C NMR (125 MHz, $CDCl_3$): δ 19.27 ($\underline{C}(CH_3)_3$), 26.92 ($C(\underline{C}H_3)_3$), 45.90 ($N\underline{C}H_2$), 62.28 ($O\underline{C}H_2$), 100.22 ($\underline{C}H$—Ar), 104.85 ($\underline{C}H$—Ar), 106.48 ($\underline{C}H$—Ar), 127.85 ($\underline{C}H$—Ar), 129.86 ($\underline{C}H$—Ar), 130.27 ($\underline{C}H$—Ar), 133.39 ($\underline{C}$—Ar), 135.64 ($\underline{C}H$—Ar), 149.76 ($\underline{C}$—Ar), 156.81 ($\underline{C}$—Ar); HRESI-MS (m/z) Calcd for $C_{24}H_{29}NO_2Si$ [M+H]+: 392.2047, found: 392.2033.

Example 3: Preparation of N-(3-hydroxyphenyl)-N-(2-(tert-butyldiphenylsilyloxy)ethyl)-(R)-3-tetradecanoyloxytetradecanamide (6)

To a solution of dilipid acid 8 (926 mg, 2.04 mmol) in $CH_2Cl_2$ (4 mL) cooled to −20° C., N-methylmorpholine (336 μL, 3.06 mmol) and isobutyl chloroformate (278 μL, 2.14 mmol) were added successively. A solution of 5 (1.6 g. 4.08 mmol) in $CH_2Cl_2$ (4 mL) was then added dropwise over 3 minutes. The mixture was stirred at reduced temperature for 2 hours before being allowed to warm to room temperature. MeOH (2 mL) and water (2 mL) were added and the mixture concentrated. The residue was dissolved in $CH_2Cl_2$ (125 mL) and washed with water (35 mL). The organic layer was dried over $Na_2SO_4$, concentrated, and purified via flash column chromatography (hexane/acetone, 7:1) to afford 6 (1.35 g, 80%) as a colorless syrup. Rf 0.35 (hexane/acetone; 6:1); $[\alpha]_D^{22}$ +15.9 (c 1.0, $CHCl_3$); $^1$H NMR (500 MHz, $CDCl_3$): δ 0.88 (t, 6H, J 6.5 Hz, $CH_3$×2). 1.01 (s, 9H, $C(CH_3)_3$), 1.14-1.36 (br m, 38H, $CH_2$×19), 1.50-1.62 (br m, 4H, H-4$_L$, H-3$_L$), 2.20 (t, 2H, J 7.5 Hz, H-2$_L$), 2.29 (dd, 1H, J 15.5, 6.0 Hz, H-2$^{LB}$), 2.40 (dd, 1H, J 15.5, 7.0 Hz, H-2$_{LA}$), 3.76-3.85 (m, 4H, $NCH_2$, $OCH_2$), 5.16-5.22 (m, 1H, H-3$_L$), 6.38-6.48 (br s, 1H, OH), 6.64 (s, 1H, Ar—H), 6.71 (d, 1H, J 8.0 Hz, Ar—H), 6.83 (d, 1H, J 8.0 Hz, Ar—H), 7.19 (dd, 1H, J 8.0, 8.0 Hz, Ar—H), 7.32-7.41 (m, 6H, Ar—H), 7.58-7.61 (m, 4H, Ar—H); $^{13}$C NMR (125 MHz, $CDCl_3$): δ 14.16 ($CH_3$), 19.19 ($\underline{C}(CH_3)_3$), 22.72 ($CH_2$), 25.02 ($CH_2$), 25.26 ($CH_2$), 26.83 ($\underline{C}(CH_3)_3$), 29.17 ($CH_2$), 29.39 ($CH_2$), 29.40 ($CH_2$), 29.55 ($CH_2$), 29.57 ($CH_2$), 29.60 ($CH_2$), 29.67 ($CH_2$), 29.68 ($CH_2$), 29.69 ($CH_2$), 29.71 ($CH_2$), 29.73 ($CH_2$), 31.95 ($CH_2$), 34.26 ($CH_2$), 34.58 ($CH_2$), 39.08 (C-2$_L$), 51.37 ($N\underline{C}H_2$), 61.07 ($O\underline{C}H_2$), 71.36 (C-3$_L$), 115.29 ($\underline{C}H$—Ar), 115.49 ($\underline{C}H$—Ar), 120.11 ($\underline{C}H$—Ar), 127.70 ($\underline{C}H$—Ar), 129.68 ($\underline{C}H$—Ar), 130.41 ($\underline{C}H$—Ar), 133.51 ($\underline{C}$—Ar), 135.55 ($\underline{C}H$—Ar), 143.56 ($\underline{C}$—Ar), 157.17 ($\underline{C}$—Ar), 170.05 (C=O), 173.55 (C=O); HRESI-MS (m/z) Calcd for $C_{52}H_{81}NO_5Si$ [M+H]+: 828.5963, found: 828.5926.

Example 4: Preparation of N-(3-hydroxyphenyl)-N-(2-hydroxyethyl)-(R)-3-tetradecanoyloxytetradecanamide (7)

To a solution of 6 (993 mg, 1.20 mmol) in $CH_2Cl_2$ (10 mL), HOAc (0.85 mL, 14.49 mmol) and $Bu_4NF$ (1M in THF, 7.24 mL) were added successively. The mixture was stirred at room temperature overnight, and then concentrated. The residue was dissolved in $CH_2Cl_2$ (150 mL) and washed with a saturated sodium bicarbonate solution (40 mL). The organic layer was dried over $Na_2SO_4$, concentrated, and purified via flash column chromatography (hexane/EtOAc/MeOH, 2:1:0.1) to yield 7 (571 mg, 81%) as a colorless syrup. Rf 0.31 (hexane/EtOAc/MeOH, 2:1:0.1); $[\alpha]_D^{22}$ +4.5 (c 1.0, $CHCl_3$); $^1$H NMR (500 MHz, $CDCl_3$): δ 0.88 (t, 6H, J 6.5 Hz, $CH_3$×2), 1.10-1.32 (br m, 38H, $CH_2$×19), 1.44-1.57 (br m, 4H, H-4$_L$, H-3$_L$), 2.27 (t, 2H, J 7.5 Hz, H-2L'), 2.34-2.45 (m, 2H, H-2$_L$), 3.68-3.93 (m, 6H, $NCH_2$, $OCH_2$, OH×2), 5.15-5.24 (m, 1H, H-3$_L$), 6.75 (d, 1H, J 8.0 Hz, Ar—H), 6.85 (s, 1H, Ar—H), 6.89 (d, J 8.0 Hz, Ar—H), 7.27 (dd, 1H, J 8.0, 8.0 Hz, Ar—H); $^{13}$C NMR (125 MHz, $CDCl_3$): δ 14.16 ($CH_3$), 22.72 ($CH_2$), 24.99 ($CH_2$), 25.20 ($CH_2$), 29.17 ($CH_2$), 29.33 ($CH_2$), 29.40 ($CH_2$), 29.53 ($CH_2$), 29.55 ($CH_2$), 29.59 ($CH_2$), 29.68 ($CH_2$), 29.71 ($CH_2$), 29.74 ($CH_2$), 31.95 ($CH_2$), 34.41 ($CH_2$), 34.59 ($CH_2$), 39.36 (C-2$_L$), 52.33 ($N\underline{C}H_2$), 60.54 ($O\underline{C}H_2$), 71.45 (C-3$_L$), 115.48 ($\underline{C}H$—Ar), 115.97 ($\underline{C}H$—Ar), 119.01 ($\underline{C}H$—Ar), 130.86 ($\underline{C}H$—Ar), 143.00 ($\underline{C}$—Ar), 158.02 ($\underline{C}$—Ar), 172.18 (C=O), 174.22 (C=O); HRESI-MS (m/z) Calcd for $C_{36}H_{63}NO_5$[M+H]$^+$: 590.4785, found: 590.4752.

Example 5: Preparation of N-(3-hydroxyphenyl)-N-{2-[6-O-benzyl-2-deoxy-4-O-(di-O-benzylphosphono)-3-O—((R)-3-tetradecanoyloxytetradecanoyl)-2-(2,2,2-trichloroethoxycarbonylamino)-β-D-glucopyranosyloxy]-ethyl}-(R)-3-tetradecanoyloxytetradecanamide (10)

A solution of 7 (565 mg, 0.96 mmol) and imidate 9 (1.23 g, 0.96 mmol) in $CH_2Cl_2$ (8 mL) in the presence of molecular sieves (4 Å, 4.0 g) was stirred under nitrogen at room temperature for 30 min. A solution of TMSOTf (0.02 M in $CH_2Cl_2$, 0.95 mL) was added dropwise in about 3 min. The mixture was stirred at room temperature for 1 h before a saturated sodium bicarbonate solution (15 mL) was added to quench the reaction. Solids were filtered out, and the filtrate was extracted with $CH_2Cl_2$ (3×30 mL). The combined organic phase was dried over $Na_2SO_4$, concentrated, and purified via flash column chromatography (hexane/EtOAC/MeOH, 3:1:0.1) to yield 10 (1.46 g, 89%) as a colorless syrup. Rf 0.36 (hexane/EtOAC/MeOH, 3:1:0.1); $[\alpha]_D^{\ >}$ −10.6 (c 1.0, $CHCl_3$); $^1$H NMR (500 MHz, $CDCl_3$): δ 0.88 (t, 12H, J 6.5 Hz, $CH_3$×4), 1.15-1.38 (br m, 76H, $CH_2$×38), 1.42-1.58 (br m, 8H, H-4$_L$, H-3$_L$), 2.19-2.52 (m, 8H, H-2$_L$, H-2$_L$), 3.54-3.62 (m, 4H, H-5, H-6B, $NCH_2$), 3.66-3.71 (m, 1H, H-2), 3.76-3.81 (m, 1H, H-6A), 3.93-4.06 (m, 2H, $OCH_2$), 4.42-4.53 (m, 3H, H-4, Ph-$CH_2$), 4.59 (d, 1H, J 8.5 Hz, H-1), 4.63 (d, 1H, J 12.0 Hz, Troc-H$_B$), 4.71 (d, 1H, J 12.0 Hz, Troc-H$_A$), 4.87-4.94 (m, 4H, (PhCH$_2$O)$_2$P), 5.11-5.22 (m, 2H, H-3$_L$), 5.27 (dd, 1H, J 10.0, 10.0 Hz, H-3), 5.82 (d, 1H, J 8.0 Hz, NH), 6.00 (br s, 1H, OH), 6.65 (d, 1H, J 7.5 Hz, Ar—H), 6.83 (d, 1H, J 8.0 Hz, Ar—H), 6.95 (s, 1H, Ar—H), 7.17-7.35 (m, 16H, Ar—H); $^{13}$C NMR (125 MHz, $CDCl_3$): δ 14.16 ($CH_3$), 22.72 ($CH_2$), 25.01 ($CH_2$), 25.05 ($CH_2$), 25.12 ($CH_2$), 25.19 ($CH_2$), 29.19 ($CH_2$), 29.36 ($CH_2$), 29.40 ($CH_2$), 29.57 ($CH_2$), 29.60 ($CH_2$), 29.62 ($CH_2$), 29.69 ($CH_2$), 29.71 ($CH_2$), 29.73 ($CH_2$), 31.95 ($CH_2$), 34.18 ($CH_2$), 34.35 ($CH_2$), 34.45 ($CH_2$), 34.61 ($CH_2$), 39.01 (C-2$_L$), 39.20 (C-2$_L$), 49.61 ($NCH_2$), 56.38 (C-2), 66.58 (O$CH_2$), 68.28 (C-6), 69.70-69.86 (m, (Ph$CH_2$O)$_2$P), 69.90 (C-3$_L$), 71.33 (C-3$_L$), 72.80 (C-3), 73.45 (Ph-$CH_2$), 73.88 (d, J 5.5 Hz, C-4), 73.93 (C-5), 74.71 (Troc-$CH_2$), 95.22 (Troc-$CCl_3$), 100.01 (C-1), 115.42 (CH—Ar), 115.87 (CH—Ar), 119.22 (CH—Ar), 127.73 (CH—Ar), 128.04 (CH—Ar), 128.14 (CH—Ar), 128.39 (CH—Ar), 128.62 (CH—Ar), 128.70 (CH—Ar), 135.41 (C—Ar), 135.44 (C—Ar), 137.74 (C—Ar), 143.52 (C—Ar), 155.09 (C═O, Troc), 157.67 (C—Ar), 170.32 (C═O), 170.38 (C═O), 173.59 (C═O); MALDI-MS (m/z) Calcd for $C_{94}H_{146}Cl_3N_2O_{17}P$ [M+Na]+: 1733.9325, found: 1733.9720.

Example 6: Preparation of N-(3-hydroxyphenyl)-N-{2-[6-O-benzyl-2-deoxy-4-O-(di-O-benzylphosphono)-3-O—((R)-3-tetradecanoyloxytetradecanoyl)-2-((R)-3-tetradecanoyloxytetradecanamido)-β-D-glucopyranosyloxy]-ethyl}-(R)-3-tetradecanoyloxytetradecanamide (11)

To a solution of 10 (550 mg, 0.32 mmol) in glacial acetic acid (20 mL) and EtOAc (5 mL), zinc powder (3.0 g) was added and the mixture was stirred at room temperature for 45 min. The mixture was then filtered, the solids were washed with an acetic acid/EtOAc solution (9:1, 40 mL), and the filtrate was concentrated. The residue was dissolved in $CH_2Cl_2$ (100 mL), washed with a saturated sodium bicarbonate solution (40 mL) and the aqueous layer was extracted with $CH_2Cl_2$ (2×40 mL). The combined organic phase was dried over $Na_2SO_4$ and concentrated to give the crude amine (455 mg) as a colorless syrup.

To a solution of dilipid acid 8 (182 mg, 0.40 mmol) in $CH_2Cl_2$ (2 mL), DIC (125 μL, 0.80 mmol) was added and the mixture was stirred at room temperature for 10 minutes. To this mixture, a solution of the crude amine (450 mg) in $CH_2Cl_2$ was added, and the resulting mixture was stirred at room temperature overnight. Water (0.5 mL) was added, and the mixture was then dried over $Na_2SO_4$. Solids were filtered off, and the filtrate was concentrated. The residue was purified via flash column chromatography (hexane/EtOAC/MeOH, 3:1:0.1) to afford 11 (430 mg, 68%) as a colorless syrup. Rf 0.37 (hexane/EtOAC/MeOH, 2:1:0.1); $[\alpha]_D^{22}$ −3.9 (c 1.0, $CHC_3$); $^1$H NMR (500 MHz, $CDCl_3$):): δ 0.88 (t, 18H, J 6.5 Hz, $CH_3$×6), 1.17-1.40 (br m, 114H, $CH_2$×57), 1.40-1.63 (br m, 12H, H-4$_L$, H-3$_L$), 2.18-2.52 (m, 12H, H-2$_L$, H-2L'), 3.55-3.63 (m, 4H, H-5, H-6B, $NCH_2$), 3.76-3.80 (m, 3H, H-6A, $OCH_2$), 4.20-4.27 (m, 1H, H-2), 4.40 (d, 1H, J 8.0 Hz, H-1), 4.43-4.52 (m, 3H, H-4, Ph-$CH_2$), 4.87-4.96 (m, 5H, (Ph$CH_2$O)$_2$P, H-3$_L$), 5.09-5.14 (m, 2H, H-3, H-3$_L$), 5.22-5.28 (m, 1H, H-3$_L$), 6.50 (d, 1H, J 9.5 Hz, NH), 6.61 (d, 1H, J 8.0 Hz, Ar—H), 6.82 (d, 1H, J 8.0 Hz, Ar—H), 7.01 (s, 1H, Ar—H), 7.16 (dd, 1H, J 8.0, 8.0 Hz, Ar—H), 7.23-7.32 (m, 15H, Ar—H), 8.66 (br s, 1H, OH); $^{13}$C NMR (125 MHz, $CDCl_3$): δ 14.15 ($CH_3$), 22.72 ($CH_2$), 24.96 ($CH_2$), 25.00 ($CH_2$), 25.09 ($CH_2$), 25.12 ($CH_2$), 25.24 ($CH_2$), 29.21 ($CH_2$), 29.25 ($CH_2$), 29.40 ($CH_2$), 29.47 ($CH_2$), 29.49 ($CH_2$), 29.57 ($CH_2$), 29.61 ($CH_2$), 29.65 ($CH_2$), 29.69 ($CH_2$), 29.71 ($CH_2$), 29.73 ($CH_2$), 29.75 ($CH_2$), 31.96 ($CH_2$), 34.13 ($CH_2$), 34.25 ($CH_2$), 34.40 ($CH_2$), 34.41 ($CH_2$), 34.50 ($CH_2$), 34.61 ($CH_2$), 38.87 (C-2$_L$), 38.97 (C-2$_L$), 41.84 (C-2$_L$), 50.69 ($NCH_2$), 53.78 (C-2), 67.00 ($OCH_2$), 68.29 (C-6), 69.68-69.73 (m, (Ph$CH_2$O)$_2$P), 69.79 (C-3$_L$), 70.88 (C-3$_L$), 71.45 (C-3$_L$), 72.85 (C-3), 73.53 (Ph-$CH_2$), 73.84 (d, J 5.5 Hz, C-4), 74.31 (C-5), 100.88 (C-1), 115.25 (CH—Ar), 115.57 (CH—Ar), 118.48 (CH—Ar), 127.66 (CH—Ar), 127.69 (CH—Ar), 128.04 (CH—Ar), 128.13 (CH—Ar), 128.41 (CH—Ar), 128.60 (CH—Ar), 128.61 (CH—Ar), 128.67 (CH—Ar), 135.48 (C—Ar), 135.53 (C—Ar), 137.86 (C—Ar), 144.12 (C—Ar), 158.41 (C—Ar), 170.04 (C═O), 170.98 (C═O), 171.92 (C═O), 173.16 (C═O), 173.43 (C═O), 173.73 (C═O); MALDI-MS (m/z) Calcd for $C_{119}H_{197}N_2O_{18}P$ [M+Na]+: 1996.4199, found: 1996.4117.

Example 7: Preparation of N-(3-(di-O-benzylphosphono)-phenyl)-N-{2-[6-O-benzyl-2-deoxy-4-O-(di-O-benzylphosphono)-3-O—((R)-3-tetradecanoyloxytetradecanoyl)-2-((R)-3-tetradecanoyloxytetradecanamido)-β-D-glucopyranosyloxy]-ethyl}-(R)-3-tetradecanoyloxytetradecanamide (12)

To a solution of 11 (122 mg, 0.062 mmol) in $CH_2Cl_2$ (3 mL), 5-phenyltetrazole (27 mg, 0.18 mmol) and N,N-diisopropylphosphoramidite (42 μL, 0.124 mmol) were added. The mixture was stirred at room temperature for 1 h and then cooled to 0° C. before the addition of m-chloroperbenzoic acid (46 mg, 77%, 0.186 mmol). The mixture was stirred at the reduced temperature for 1 h before being allowed to warm to room temperature.

An aqueous $NaHSO_3$ solution (10%, 15 mL) was added and the mixture was stirred at room temperature for 20 minutes. The mixture was then extracted with $CH_2Cl_2$ (3×15 mL), and the combined organic phase was washed with a saturated sodium bicarbonate solution (15 mL). The organic phase was dried over $Na_2SO_4$, concentrated, and purified by flash column chromatography (hexane/acetone, 4:1) to give 12 (129 mg, 93%) as a colorless syrup. Rf 0.28 (hexane/acetone, 4:1); $[\alpha]_D^{22}$ −2.6 (c 1.0, CHCl$_3$); $^1$H NMR (500 MHz, CDCl$_3$): δ 0.88 (t, 18H, J 6.5 Hz, CH$_3$×6), 1.15-1.37 (br m, 114H, CH$_2$×57), 1.41-1.64 (br m, 12H, H-4$_L$, H-3$_L'$), 2.14-2.48 (m, 12H, H-2$_L$, H-2L'), 3.47-3.53 (m, 1H, H-2), 3.56-3.69 (m, 4H, H-5, H-6B, NCH$_2$), 3.75-3.77 (m, 1H, H-6A), 3.82-3.91 (m, 2H, OCH$_2$), 4.39-4.49 (m, 3H, H-4, Ph-CH$_2$), 4.85-4.92 (m, 5H, H-1, (PhCH$_2$O)$_2$P), 5.11-5.19 (m, 7H, (PhCH$_2$O)$_2$P, H-3$_L$×3), 5.49 (dd, 1H, J 10.0, 10.0 Hz, H-3), 6.70 (d, 1H, J 7.5 Hz, NH), 7.02-7.10 (m, 3H, Ar—H), 7.19-7.34 (m, 26H, Ar—H); $^{13}$C NMR (125 MHz, CDCl$_3$): δ 14.16 (CH$_3$), 22.72 (CH$_2$), 25.03 (CH$_2$), 25.05 (CH$_2$), 25.14 (CH$_2$), 25.28 (CH$_2$), 25.32 (CH$_2$), 29.23 (CH$_2$), 29.31 (CH$_2$), 29.40 (CH$_2$), 29.43 (CH$_2$), 29.48 (CH$_2$), 29.60 (CH$_2$), 29.62 (CH$_2$), 29.64 (CH$_2$), 29.72 (CH$_2$), 29.74 (CH$_2$), 29.76 (CH$_2$), 31.96 (CH$_2$), 31.98 (CH$_2$), 34.26 (CH$_2$), 34.34 (CH$_2$), 34.44 (CH$_2$), 34.54 (CH$_2$), 38.99 (C-2$_L$), 39.18 (C-2$_L$), 40.98 (C-2$_L$), 49.12 (NCH$_2$), 55.43 (C-2), 66.10 (OCH$_2$), 68.55 (C-6), 69.45-69.64 (m, (PhCH$_2$O)$_2$P), 69.90 (C-3$_L$), 70.20-70.32 (m, (Ph CH$_2$O)$_2$P), 70.49 (C-3$_L$), 70.98 (C-3$_L$), 72.71 (C-3), 73.30 (Ph-CH$_2$), 73.97 (d, J 5.5 Hz, H-4), 74.30 (C-5), 99.35 (C-1), 119.74 (CH—Ar), 120.50 (CH—Ar), 125.53 (CH—Ar), 127.50 (CH—Ar), 127.55 (CH—Ar), 127.97 (CH—Ar), 128.08 (CH—Ar), 128.12 (CH—Ar), 128.30 (CH—Ar), 128.54 (CH—Ar), 128.70 (CH—Ar), 128.73 (CH—Ar), 128.87 (CH—Ar), 130.60 (CH—Ar), 135.16 (C—Ar), 135.21 (C—Ar), 135.60 (C—Ar), 135.65 (C—Ar), 138.14 (C—Ar), 143.82 (C—Ar), 151.02 (d, J 5.5 Hz, C—Ar), 169.65 (C=O), 170.06 (C=O), 170.17 (C=O), 173.15 (C=O), 173.19 (C=O), 173.35 (C=O); MALDI-MS (m/z) Calcd for $C_{133}H_{210}N_2O_{21}P_2$[M+Na]$^+$: 2256.4801, found: 2256.5198.

Example 8: Preparation of N-(3-hydroxyphenyl)-N-{2-deoxy-4-O-phosphono-3-O—((R)-3-tetradecanoyloxytetradecanoyl)-2-((R)-3-tetradecanoyloxytetradecanamido)-β-D-glucopyranosyloxy]-ethyl}-(R)-3-tetradecanoyloxytetradecanamide (2)

To a solution of 11 (146 mg, 0.074 mmol) in freshly distilled THF (70 mL), palladium on charcoal (5%, 45 mg) was added and the mixture was stirred at room temperature under a hydrogen atmosphere for 24 h. The mixture was filtered, and the filtrate concentrated. The residue was purified by flash column chromatography (CHCl$_3$/MeOH, 9:1→CHCl$_3$/MeOH/H$_2$O, 4:1:0.1) to afford JL-265 (2) (111 mg, 88%) as white fluffy solid after being freeze dried from a dioxane-CHCl$_3$ mixture (95:5). Rf 0.57 (CHCl$_3$/MeOH/H$_2$O, 4:1:0.1); $[\alpha]_D^{22}$−0.6 (c 0.5, CHCl$_3$); $^1$H NMR (500 MHz, CDCl$_3$): δ 0.89 (t, 18H, J 6.5 Hz, CH$_3$×6), 1.12-1.39 (br m, 114H, CH$_2$×57), 1.43-1.66 (br m, 12H, H-4$_L$, H-3$_L'$), 2.20-2.47 (m, 10H, H-2$_L$×4, H-2$_L'$), 2.55-2.72 (m, 2H, H-2$_L$×2), 3.61-3.74 (m, 4H, H-5, H-6B, NCH$_2$), 3.83-3.94 (m, 3H, H-2, OCH$_2$), 4.01-4.03 (m, 1H, H-6A), 4.20-4.25 (m, 1H, H-4), 4.48 (d, 1H, J 8.0 Hz, H-1), 5.10-5.26 (m, 4H, H-3, H-3$_L$), 6.65 (d. 1H, J 8.0 Hz, Ar—H), 6.81-6.87 (m, 2H, Ar—H), 7.25 (dd, 1H, J 8.0, 8.0 Hz, Ar—H); MALDI-MS (m/z) Calcd for $C_{98}H_{179}N_2O_{18}P$ [M+Na]$^+$: 1726.2790, found: 1726.2794.

Example 9: Preparation of N-(3-phosphonoxyphenyl)-N-{2-deoxy-4-O-phosphono-3-O—((R)-3-tetradecanoyloxytetradecanoyl)-2-((R)-3-tetradecanoyloxytetradecanamido)-β-D-glucopyranosyloxy]-ethyl}-(R)-3-tetradecanoyloxytetradecanamide (3)

In a similar manner as described for the global deprotection of 11, a solution of 12 (203 mg, 0.091 mmol) and palladium on charcoal (5%, 45 mg) in freshly distilled THF (75 mL) was stirred under a hydrogen atmosphere at room temperature for 24 h. The mixture was filtered, the filtrate concentrated, and the resulting residue was purified by flash column chromatography (CHCl3/MeOH, 9:1→CHCl$_3$/MeOH/H$_2$O, 2:1:0.2) to yield JL-266 (3) (145 mg, 89%) as a white fluffy solid after being freeze dried from a dioxane-CHCl$_3$ mixture (95:5). Rf 0.51 (CHCl$_3$/MeOH/H$_2$O/NH$_4$OH, 2:1:0.2:0.1); $[\alpha]_D^{22}$ −0.4 (c 0.5, CHCl$_3$); $^1$H NMR (500 MHz, CDCl$_3$): δ 0.89 (t, 18H, J 6.5 Hz, CH$_3$×6), 1.18-1.39 (br m, 114H, CH$_2$×57), 1.49-1.68 (br m, 12H, H-4$_L$, H-3$_L'$), 2.20-2.47 (m, 10H, H-2$_L$×4, H-2L'), 2.55-2.72 (m, 2H, H-2$_L$×2), 3.51-3.80 (br m, H-2, H-5, H-6B, NCH$_2$), 3.85-3.99 (br m, 3H, H-6A, OCH$_2$), 4.21-4.28 (br m, 1H, H-4), 4.56 (d, 1H, J 8.0 Hz, H-1), 5.11-5.27 (m, 4H, H-3, H-3$_L$), 6.88 (d, 1H, J 8.0 Hz, Ar—H), 7.20-7.28 (br m, 2H, Ar—H), 7.35 (dd, 1H, J 8.0, 8.0 Hz, Ar—H); MALDI-MS (m/z) Calcd for $C_{98}H_{180}N_2O_{21}P_2$[M+Na]$^+$: 1806.2458, found: 1806.2502.

Example 10

Pathogen-free, female C57BL6 mice, 6-8 weeks of age were purchased from Charles River Laboratories (St. Constant, Quebec, Canada) and were housed according to institutional guidelines with water and food ad libitum under filter controlled air circulation.

The C3 tumor cell line used in this study is a well-described mouse model for pre-clinical cervical cancer research. HPV16-expressing C3 cells are derived from B6 mouse embryo cells transformed with the complete HPV16 genome under its own promoter and an activated-ras oncogene. The C3 cell line develops tumors when injected subcutaneously and has been used in cancer challenge studies to examine the efficacy of vaccine administered before or after C3 tumor cell implantation. The C3 cell line was maintained in Iscove Modified Dulbecco's Medium (IMDM; Sigma, St. Louis, Mo.) supplemented with 10% heat-inactivated fetal calf serum (Hyclone), 2 mM 1-glutamine, 50 mM 2-mercaptoethanol, penicillin and streptomycin. Cells were incubated at 37° C./5% CO$_2$.

The HPV16E7 (H-2Db) peptide 49-67, RAHYNIVTF (SEQ ID NO: 1), containing a CTL epitope was fused to PADRE containing a CD4+ T helper epitope by Polypeptide Group (San Diego, Calif., USA). This peptide is hereafter designated as FP.

To formulate the vaccines herein, 160 micrograms of FP was mixed with a DOPC/cholesterol mixture (10:1, w/w, Lipoid GmbH, Germany) dissolved in tert-butanol. When lipid A mimics were included, 160 micrograms of JL-265 or JL-266 were added to the FP/DOPC/chol mixture. The mixture was lyophilized and then reconstituted in reconstituted in 700 microlitres of sterile water to formulate liposomes containing antigen with or without lipid A mimic. Each vaccine dose was 50 microlitres and contained 10 micrograms of FP peptide with or without 10 micrograms of lipid A mimic (JL-265 or JL-266).

To test the efficacy of these liposome-based vaccine formulations, groups of mice (7 mice per group) were implanted subcutaneously in the left flank with 5×10E5 C3 cells suspended in 100 microlitres of HBSS media. Five days later, mice were vaccinated subcutaneously in the right flank with 50 microlitres of vaccine. Mice in Group 1 were vaccinated with FP peptide (10 micrograms) in liposomes containing no lipid A mimic. Mice in Group 2 were vaccinated with FP peptide (10 micrograms) in liposomes containing JL-265 (10 micrograms). Mice in Group 3 were vaccinated with FP peptide (10 micrograms) in liposomes containing JL-266 (10 micrograms). Mice in Group 4 served as a tumor growth control and were vaccinated with saline containing no antigen or lipid A mimic.

As shown in FIG. 4, mice in Groups 2 and 3 which were immunized with vaccine containing either JL-265 or JL-266 lipid A mimic had significantly smaller tumor volumes at 28 days compared the mice in the control groups.

Example 11

Pathogen-free, female C57BL6 mice, 6-8 weeks of age were purchased from Charles River Laboratories (St. Constant, Quebec, Canada) and were housed according to institutional guidelines with water and food ad libitum under filter controlled air circulation.

The C3 tumor cell line used in this study is a well-described mouse model for pre-clinical cervical cancer research. HPV16-expressing C3 cells are derived from B6 mouse embryo cells transformed with the complete HPV16 genome under its own promoter and an activated-ras oncogene. The C3 cell line develops tumors when injected subcutaneously and has been used in cancer challenge studies to examine the efficacy of vaccine administered before or after C3 tumor cell implantation. The C3 cell line was maintained in Iscove Modified Dulbecco's Medium (IMDM; Sigma, St. Louis, Mo.) supplemented with 10% heat-inactivated fetal calf serum (Hyclone), 2 mM 1-glutamine, 50 mM 2-mercaptoethanol, penicillin and streptomycin. Cells were incubated at 37° C./5% $CO_2$.

The HPV16E7 (H-2Db) peptide 49-67, RAHYNIVTF (SEQ ID NO: 1), containing a CTL epitope was fused to PADRE containing a CD4+ T helper epitope by Polypeptide Group (San Diego, Calif., USA). This peptide is hereafter designated as FP.

To formulate the vaccine herein, FP peptide was solubilized in dimethyl sulfoxide and mixed with Incomplete Freund's adjuvant (IFA). The lipid A mimics JL-265 and JL-266 were also solubilized in dimethyl sulfoxide and, where indicated, added to the FP/IFA mixture. Each vaccine dose was 50 microliters and contained 10 micrograms of FP antigen; lipid A mimic dose was 10 micrograms.

To test the efficacy of these oil-based vaccine formulations, groups of mice (7 mice per group) were implanted subcutaneously in the left flank with 5×10E5 C3 cells suspended in 100 microlitres of HBSS media. Five days later, mice were vaccinated subcutaneously in the right flank with 50 microlitres of vaccine. Mice in Group 1 were vaccinated with FP peptide (10 micrograms) in oil containing no lipid A mimic. Mice in Group 2 were vaccinated with FP peptide (10 micrograms) in oil containing JL-265 (10 micrograms). Mice in Group 3 were vaccinated with FP peptide (10 micrograms) in oil containing JL-266 (10 micrograms). Mice in Group 4 served as a tumor growth control and were vaccinated with saline containing no antigen or lipid A mimic.

As shown in FIG. 5, mice in Groups 2 and 3 which were immunized with vaccine containing either JL-265 or JL-266 lipid A mimic had significantly smaller tumor volumes at 28 days compared the mice in the control groups.

Example 12

Pathogen-free, female C57BL6 mice, 6-8 weeks of age were purchased from Charles River Laboratories (St. Constant, Quebec, Canada) and were housed according to institutional guidelines with water and food ad libitum under filter controlled air circulation.

The C3 tumor cell line used in this study is a well-described mouse model for pre-clinical cervical cancer research. HPV16-expressing C3 cells are derived from B6 mouse embryo cells transformed with the complete HPV16 genome under its own promoter and an activated-ras oncogene. The C3 cell line develops tumors when injected subcutaneously and has been used in cancer challenge studies to examine the efficacy of vaccine administered before or after C3 tumor cell implantation. The C3 cell line was maintained in Iscove Modified Dulbecco's Medium (IMDM; Sigma, St. Louis, Mo.) supplemented with 10% heat-inactivated fetal calf serum (Hyclone), 2 mM 1-glutamine, 50 mM 2-mercaptoethanol, penicillin and streptomycin. Cells were incubated at 37° C./5% $CO_2$.

The HPV16E7 (H-2Db) peptide 49-67, RAHYNIVTF (SEQ ID NO: 1), containing a CTL epitope was fused to PADRE containing a CD4+ T helper epitope by Polypeptide Group (San Diego, Calif., USA). This peptide is hereafter designated as FP.

To formulate vaccines described herein, a 10:1 mixture of dioleoyl phosphatidylcholine (DOPC) (120 milligrams/mL) and cholesterol (12 milligrams/mL) was solubilized in tert-butanol. FP antigen was first solubilized in dimethyl sulfoxide, although a water suspension of FP can also be used, and then added to the DOPC/cholesterol/tert-butanol mixture. The lipid A mimics JL-265 and JL-266 were first solubilized in dimethyl sulfoxide. Where indicated, JL-265 or JL-266 were also added to the FP/DOPC/tert-butanol mixture. A dry homogeneous mixture of antigen with or without lipid A mimic was prepared by removing the solvent and water present in the formulation by lyophilization. The dry mixture was then suspended in Incomplete Freund's adjuvant, a mineral oil-based model hydrophobic carrier. This formulation is henceforth referred to as DepoVax (DPX).

To test the efficacy of these oil-based vaccine formulations, groups of mice (8 mice per group) were implanted subcutaneously in the left flank with 5×10E5 C3 cells suspended in 100 microlitres of HBSS media. Five days later, mice were vaccinated subcutaneously in the right flank with 50 microlitres of vaccine. Mice in Group 1 were vaccinated with FP peptide (10 micrograms) in DPX containing no lipid A mimic. Mice in Group 2 were vaccinated with FP peptide (10 micrograms) in DPX containing JL-265 (10 micrograms). Mice in Group 3 were vaccinated with FP peptide (10 micrograms) in DPX containing JL-266 (10 micrograms). Mice in Group 4 served as a tumor growth control and were vaccinated with saline containing no antigen or lipid A mimic.

Figure 6:
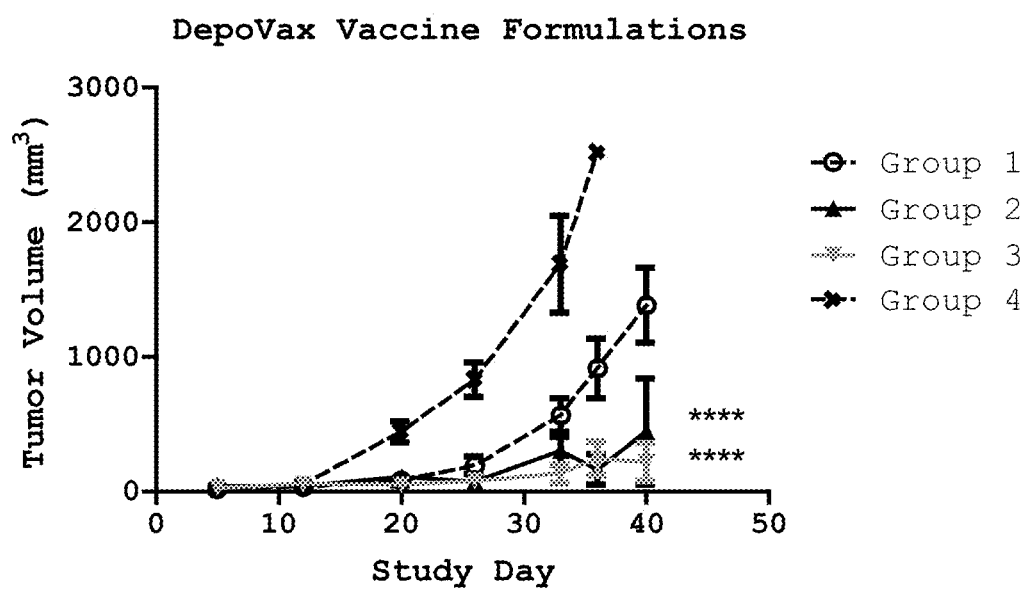
FIG. 6 illustrates the reduction in tumor volume generated by DepoVax™ (DPX) vaccine compositions of the invention comprising exemplary lipid A mimics JL-265 and JL-266. Mice (C57BL6) were implanted with C3 tumors subcutaneously on day 0. On day 5, groups of mice (n=8) were vaccinated as follows: Mice in Group 1 were vaccinated with FP peptide (10 micrograms) in DPX containing no adjuvant. Mice in Group 2 were vaccinated with FP peptide (10 micrograms) in DPX containing JL-265 (10 micrograms). Mice in Group 3 were vaccinated with FP peptide (10 micrograms) in DPX containing JL-266 (10 micrograms). Mice in Group 4 served as a tumor growth control and were vaccinated with saline containing no antigen or adjuvant. Tumor size was measured weekly with calipers. Significance calculated by 2-way ANOVA with Bonferroni post test comparing each group to Group 4 control: ****, $p<0.0001$.

As shown in FIG. 6, mice in Groups 2 and 3 which were immunized with vaccine containing either JL-265 or JL-266 lipid A mimic had significantly smaller tumor volumes at 40 days compared the mice in the control groups.

Example 13

Pathogen-free, female C3H/HeOuJ (wild-type) mice and C3H/HeJ (TLR4 mutant) mice, 6-8 weeks of age were purchased from the Jackson Laboratory (Bar Harbor, Me., USA) and were housed according to institutional guidelines with water and food ad libitum under filter controlled air circulation.

Dendritic cells were prepared from bone marrow of either wild-type or TLR4 mutant mice as follows. Femurs and tibia bones were isolated from naïve mice and flushed under sterile conditions with phosphate buffered saline. Red blood cells were lysed using ammonium chloride potassium lysing solution. Cells were counted and resuspended in complete RMPI 1640 media containing 10% fetal bovine serum (Hyclone, Nepean, ON, Canada), 1% penicillin-streptomycin (Gibco, Burlington, ON, Canada), 2 millimolar L-glutamine (Gibco), 1% HEPES buffer (Gibco) and 5.5 millimolar beta-mercaptoethanol (Sigma-Aldrich, Oakville, ON, Canada) at a concentration of 1.2×10E6 cells/millitre. Cells were cultured in a 6-well plate supplemented with 10 nanograms/milliliter of GM-CSF (Peprotech, Rocky Hill, N.J., USA) for 8 days, additional media was added on day 3 and day 6. On day 7, cells were stimulated with JL-265 or JL-266 prepared in DMSO, or DMSO vehicle control, or poly I:C (Thermo-Fisher), or lipopolysaccharide (LPS; Sigma-Aldrich). Non-adherent cells were collected on day 8 and stained with fluorochrome-conjugated antibodies specific for CD11c (clone), CD40 (clone) or CD86 (Clone). Cells were analyzed by flow cytometry using a FACSCalibur (BD Bioscience, Mississauga ON, Canada) and Win List 3D 7.0 software (Verity Software House, Topsham, Me., USA).

Results were analysed by gating first on CD11c positive cells (dendritic cell marker), then determining the percent that were double positive for CD40 or CD86. Results are shown in FIG. 7. In wild-type dendritic cells, Poly I:C (TLR3 agonist) and LPS (TLR4 agonist) stimulated an increase in expression of both CD40 and CD86 on the dendritic cells after overnight stimulation. The novel lipid A mimics JL-265 and JL-266 also induced increased expression of both CD40 and CD86 in wild-type dendritic cells. TLR4 mutant dendritic cells responded to poly I:C stimulation comparably to wild-type dendritic cells, but response to the LPS as well as the novel lipid A mimics was significantly reduced. These results indicate that the novel lipid A mimics described in this invention signal through TLR4.

Example 14

Pathogen-free, female C57BL6 mice, 6-8 weeks of age were purchased from Charles River Laboratories (St. Constant, Quebec, Canada) and were housed according to institutional guidelines with water and food ad libitum under filter controlled air circulation.

The peptides used in this example were synthesized by Polypeptide Group (San Diego, Calif., USA). Vaccines contained the MHC class I epitope HPV16E7 (H-2Db) 49-67 (RAHYNIVTF, R9F; SEQ ID NO: 1) and the MHC class II epitope tetanus toxin 830-843 (FNNFTVSFWLRVPKVSASHLE, F21E; SEQ ID NO: 23).

To formulate vaccines described herein, a 10:1 mixture of dioleoyl phosphatidylcholine (DOPC) (120 milligrams/mL) and cholesterol (12 milligrams/mL) was solubilized in tert-butanol. R9F and F21E peptide antigens were first solubilized in dimethyl sulfoxide and then added to the DOPC/cholesterol/tert-butanol mixture. The lipid A mimics JL-265 and JL-266 were first solubilized in dimethyl sulfoxide. Where indicated, JL-265 or JL-266 were also added to the FP/DOPC/tert-butanol mixture. A dry homogeneous mixture of antigen with or without lipid A mimic was prepared by removing the solvent and water present in the formulation by lyophilization. The dry mixture was then suspended in Incomplete Freund's adjuvant, a mineral oil-based model hydrophobic carrier. This formulation is henceforth referred to as DepoVax (DPX).

To test the immunogenicity of the vaccine, naïve mice (n=5) were immunized subcutaneously with 50 microlitres of DPX vaccine containing R9F and F21E with no lipid A mimic (Group 1), 5 micrograms of JL-265 (Group 2) or 5 micrograms of JL-266 (Group 3). Mice in Group 4 (n=2) were not immunized and served as the naïve control. Eight days after vaccination, mice in all groups were terminated and spleens collected. A single cell suspension of splenocytes was prepared at a concentration of 5×10E6 cells per milliliter and 100 microlitres added to wells of a 96-well ELISPOT plate pre-coated with anti-IFN-gamma (BD Bioscience). In duplicate, 100 microlitres of media containing 20 micrograms per milliliter of an irrelevant peptide antigen or R9F was added to the splenocytes, or media containing no peptide as a background control. The plate was incubated overnight at 37° C. and developed next day following manufacturers instructions using AEC chromogen (Sigma-Aldrich). Spots were quantified using ELISPOT plate reader (C.T.L., Shaker Heights).

As shown in FIG. 8, JL-265 lipid A mimic (Group 2) did not enhance antigen-specific IFN-gamma response to the R9F peptide, but JL-266 (Group 3) lipid A mimic did.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the scope of the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to encompass the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items.

As used herein, whether in the specification or the appended claims, the transitional terms "comprising", "including", "carrying", "having", "containing", "involving", and the like are to be understood as being inclusive or open-ended (i.e., to mean including but not limited to), and they do not exclude unrecited elements, materials or method steps. Only the transitional phrases "consisting of" and "consisting essentially of", respectively, are closed or semi-closed transitional phrases with respect to claims and exemplary embodiment paragraphs herein. The transitional phrase "consisting of" excludes any element, step, or ingredient which is not specifically recited. The transitional phrase "consisting essentially of" limits the scope to the specified elements, materials or steps and to those that do not materially affect the basic characteristic(s) of the invention disclosed and/or claimed herein.

The invention claimed is:

1. A compound of formula:

wherein:
one of A or E is a cyclic monosaccharide residue with one or more of the hydroxyl groups optionally substituted or absent, and one of A or E is a substituted or unsubstituted aromatic group;
$L_1$ and $L_2$ independently are present or absent, and if present is independently a substituted or unsubstituted, branched or linear, saturated or unsaturated, carbon chain optionally comprising one or more of O, S or N; and
D is —O—, —S— or —NH—;
wherein at least one of A or $L_1$ comprises one or more lipid chain substituents, and at least one of E or $L_2$ comprises one or more lipid chain substituents;
wherein each lipid chain substituent comprises at least one major carbon chain; and
wherein when $L_1$ or $L_2$ comprise a lipid chain substituent, the lipid chain substituent is a substituent group of $L_1$ or $L_2$;
or a pharmaceutically acceptable salt thereof.

2. The compound of claim 1, or pharmaceutically acceptable salt thereof, wherein the aromatic group is:

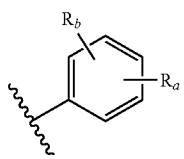

wherein:
$R_a$ is placed at any position on the benzene ring and is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6; and
$R_b$ is placed at any remaining position on the benzene ring and is —H, —OH, —NH$_2$, —Cl, —Br, —F, —COOH, —CN, —SO$_3$H, —OCH$_3$, —NO$_2$ or any substituted or unsubstituted C$_{1-6}$ alkyl.

3. The compound of claim 1, or pharmaceutically acceptable salt thereof, wherein the aromatic group is:

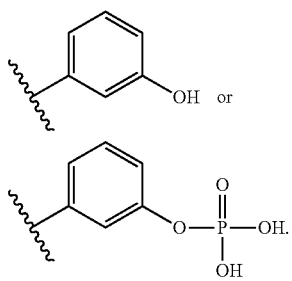

4. The compound of claim 1, or pharmaceutically acceptable salt thereof, wherein the aromatic group is:

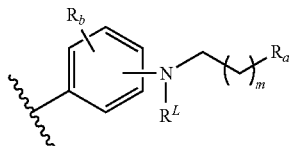

wherein:

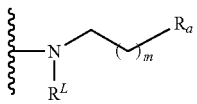

is placed at any position on the benzene ring;
$R_a$ is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6;
m is 0-6;
$R^L$ is a lipid chain substituent; and
$R_b$ is placed at any remaining position on the benzene ring and is —H, —OH, —Cl, —Br, —F, —COOH, —CN, —SO$_3$H, —OCH$_3$, —NO$_2$ or any substituted or unsubstituted C$_{1-6}$ alkyl.

5. The compound of claim 1, or pharmaceutically acceptable salt thereof, wherein A is:

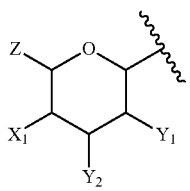

wherein:
Z is —CH$_2$G or —CH$_2$MQ, wherein G is —H, -halogen, —OH, —NH$_2$, —COOH, —OSO$_3$H, —SO$_3$H, —P(O)(OH)$_2$, or —OP(O)(OH)$_2$; M is —O—, —S—, —NH—, —OC(=O)—, —SC(=O)—, —OC(=S)—, or —NHC(=O)—; and Q is —H or a substituted or unsubstituted, branched or linear, saturated or unsaturated C$_{1-20}$ aliphatic hydrocarbon;
$X_1$ is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6; and
$Y_1$ and $Y_2$ are independently —H, —OH, —O—R$^L$, —NH—R$^L$, or —S—R$^L$, wherein R$^L$ is a lipid chain substituent.

6. The compound of claim 5, or pharmaceutically acceptable salt thereof, wherein Z is —CH$_2$OH and the stereochemistry of the substitutions on A are defined by the following formula:

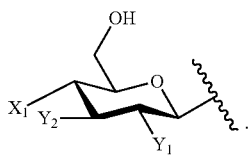

7. The compound of claim 6, or pharmaceutically acceptable salt thereof, wherein $X_1$ is —OP(O)(OH)$_2$; $Y_1$ is —NH—R$^L$; and $Y_2$ is —O—R$^L$.

8. The compound of claim 7, or pharmaceutically acceptable salt thereof, wherein $L_1$ is absent and $L_2$ is I, incorporated into the formula A-L$_1$-D-L$_2$-E as follows:

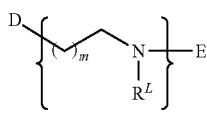

I wherein m is 0-6 and R$^L$ is a lipid chain substituent.

9. The compound of claim 1, or pharmaceutically acceptable salt thereof, wherein E is:

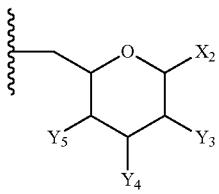

wherein:
$X_2$ is —H, —OH, —OP(O)(OH)$_2$, —P(O)(OH)$_2$, —COOH, —SO$_3$H, —OSO$_3$H, —CH(COOH)$_2$, —(O)$_k$(CH$_2$)$_n$COOH, —(O)$_k$(CH$_2$)$_q$OP(O)(OH)$_2$ or —OP(O)(OH)(OCH$_2$CH$_2$NH$_2$), wherein k is 0 or 1, n is 0-6 and q is 1-6; and $Y_3$, $Y_4$ and $Y_5$ are independently —H, —OH, —O—R$^L$, —NH—R$^L$, or —S—R$^L$, wherein R$^L$ is a lipid chain substituent.

10. The compound of claim 9, or pharmaceutically acceptable salt thereof, wherein the stereochemistry of the substitutions on E are defined by the following formula:

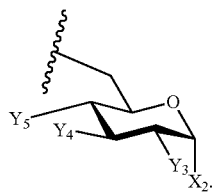

11. The compound of claim 10, or pharmaceutically acceptable salt thereof, wherein $X_2$ is —OP(O)(OH)$_2$; $Y_3$ is —NH—R$^L$; $Y_4$ is —O—R$^L$, and $Y_5$ is —OH.

12. The compound of claim 11, or pharmaceutically acceptable salt thereof, wherein $L_2$ is absent and $L_1$ is II, incorporated into the formula A-L$_1$-D-L$_2$-E as follows:

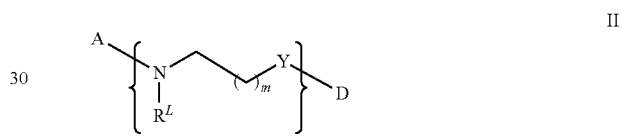

II wherein m is 0-6, Y is —(CO)$_f$—, wherein f is 0 or 1, and R$^L$ is a lipid chain substituent.

13. The compound of claim 1, or pharmaceutically acceptable salt thereof, wherein D is —O—.

14. The compound of claim 1, or pharmaceutically acceptable salt thereof, wherein each lipid chain substituent is independently:

(i)

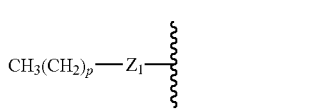

(ii)

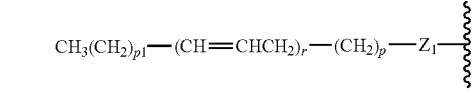

(iii)

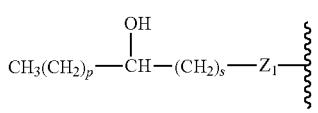

(iv)

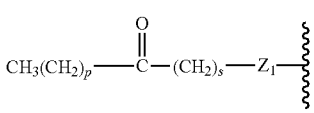

(v)

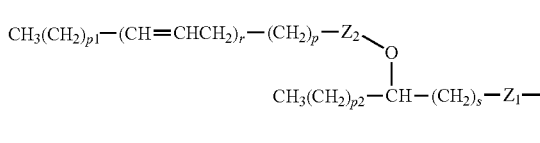

(vi)

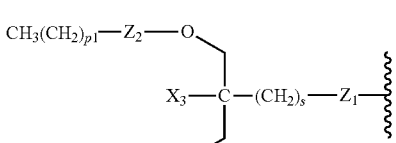

(vii)

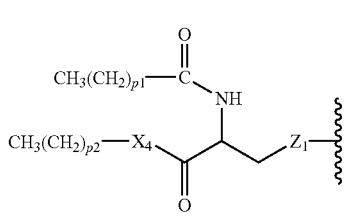

(viii)

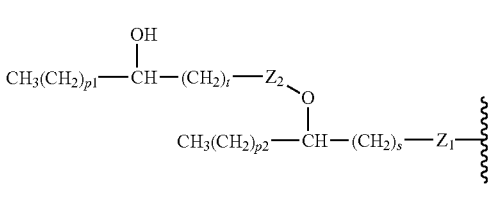

-continued (ix)

wherein:
$Z_1$, $Z_2$ and $Z_3$ are independently —C(=O)—, or —CH$_2$—;
$X_3$ is —H or —(CH$_2$)$_{p3}$CH$_3$;
$X_4$ is —NH—, —O— or —CH$_2$—;
p, p1, p2 and p3 are independently 0-30; and
r, s and t are independently 0-6.

15. The compound of claim 1, or pharmaceutically acceptable salt thereof, wherein each lipid chain substituent is independently:

16. The compound of claim 1, or pharmaceutically acceptable salt thereof, which:
has lipid A or lipopolysaccharide (LPS) antagonist activity;
has immunostimulatory activity; and/or
is capable of binding to toll-like receptor 4 (TLR4).

17. A pharmaceutical composition comprising the compound of claim 1, or pharmaceutically acceptable salt thereof, and a pharmaceutically acceptable carrier, diluent or excipient.

18. A vaccine composition comprising the compound of claim 1, or pharmaceutically acceptable salt thereof, and an antigen.

19. The vaccine composition of claim 18, which further comprises reconstituted liposomes; a carrier comprising a continuous phase of a hydrophobic substance; and a T-helper epitope.

20. The vaccine composition of claim 19, wherein the antigen is: (i) derived from a virus, bacterium or protozoan; (ii) a membrane surface-bound cancer antigen; or (iii) a toxin.

21. The vaccine composition of claim 20, wherein the antigen is derived from Ebola virus, human papillomavirus (HPV), influenza virus, respiratory syncytial virus, *Bordetella pertussis*, *Bacillus anthracis* or *Plasmodium malariae*; or the antigen is a survivin antigen.

22. The vaccine composition of claim 19, wherein the carrier is a mannide oleate in mineral oil solution.

* * * * *